United States Patent
Sum et al.

(10) Patent No.: US 8,101,590 B2
(45) Date of Patent: Jan. 24, 2012

(54) 9-AMINOCARBONYLSUBSTITUTED DERIVATIVES OF GLYCYLCYCLINES

(75) Inventors: Phaik-Eng Sum, Pomona, NY (US); Tarek Suhayl Mansour, New City, NY (US); David Brian How, Nyack, NY (US); Darrin William Hopper, New York, NY (US); Matthew Douglas Vera, Royersford, PA (US); Joshua James Sabatini, White Plains, NY (US); Jaechul Shim, Oakland, NJ (US)

(73) Assignee: Wyeth LLC, Madison, NJ (US)

( * ) Notice: Subject to any disclaimer, the term of this patent is extended or adjusted under 35 U.S.C. 154(b) by 930 days.

(21) Appl. No.: 11/513,972

(22) Filed: Aug. 31, 2006

(65) Prior Publication Data
US 2007/0049564 A1   Mar. 1, 2007

Related U.S. Application Data

(60) Provisional application No. 60/713,112, filed on Aug. 31, 2005.

(51) Int. Cl.
*A61K 31/65* (2006.01)
*C07C 237/26* (2006.01)

(52) U.S. Cl. ........................ 514/152; 552/203
(58) Field of Classification Search ............... 514/152; 552/203
See application file for complete search history.

(56) References Cited

U.S. PATENT DOCUMENTS

| | | | |
|---|---|---|---|
| 2,482,055 | A | 9/1949 | Duggar |
| 3,007,965 | A | 11/1961 | Growich, Jr. et al. |
| 3,043,875 | A | 7/1962 | Beereboom et al. |
| 3,148,212 | A | 9/1964 | Boothe et al. |
| 3,200,149 | A | 8/1965 | Blackwood et al. |
| 3,226,436 | A | 12/1965 | Petisi et al. |
| RE26,253 | E | 8/1967 | Petisi et al. |
| 3,338,963 | A | 8/1967 | Petisi et al. |
| 3,341,585 | A | 9/1967 | Bitha et al. |
| 3,360,557 | A | 12/1967 | Shu |
| 3,360,561 | A | 12/1967 | Zambrano |
| 3,518,306 | A | 6/1970 | Martell et al. |
| 5,021,407 | A | 6/1991 | Levy |
| 5,442,059 | A | 8/1995 | Sum et al. |
| 5,494,903 | A | 2/1996 | Hlavka et al. |
| 5,607,691 | A | 3/1997 | Hale et al. |
| 5,639,742 | A | 6/1997 | Lee et al. |

FOREIGN PATENT DOCUMENTS

| | | |
|---|---|---|
| WO | WO 01/74761 A1 | 10/2001 |
| WO | WO 02/072031 A2 | 9/2002 |
| WO | WO 2004/064728 * | 8/2004 |

OTHER PUBLICATIONS

Phaik-Eng Sum, et al.; J. Med. Chem.; vol. 37; pp. 184-188; 1994.
Fumio Sakamoto, et al., Chem. Pharm. Bull,; vol. 32(6); pp. 2241-2248; 1984.
I. Chopra; Handbook of Experimental Pharmacology; vol. 78; pp. 317-392; 1985.
Stuart B. Levy, et al.; Antimicrobial Agents and Chemotherapy; vol. 33,. No. 8; pp. 1373-1374; 1989.
Richard C. Larock, Comprehensive Organic Transformations, VCH Publishers, pp. 411-415, 1989.
Michael Folkmann and Frantz J. Lund; Synthesis; pp. 1159-1166; 1990.
A.A. Salyers, et al.; Molecular Microbiology; vol. 4(1); pp. 151-156; 1990.
NCCLS, 2000 Methods for Dilution Antimicrobial Susceptibility Tests for Bacteria That Grow Aerobically; Approved Standard—Fifth Edition: M7-A5, vol. 20, No. 2, National Committee for Clinical Laboratory Standards, Wayne, PA.

* cited by examiner

*Primary Examiner* — Barbara P Badio
(74) *Attorney, Agent, or Firm* — Ram W. Sabnis

(57) ABSTRACT

This invention provides compounds of Formula I having the structure

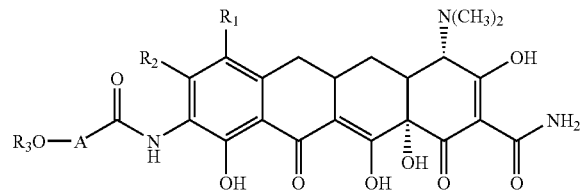

where $R_1$, $R_2$, $R_3$ and A are defined in the specification or a pharmaceutically acceptable salt thereof useful as antibacterial agents. Compounds according to Formula (II):

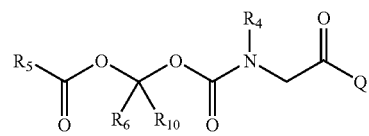

where Q, $R_4$, $R_5$, $R_6$ and $R_{10}$ and A are defined in the specification are useful as chemical intermediates.

17 Claims, No Drawings

9-AMINOCARBONYLSUBSTITUTED DERIVATIVES OF GLYCYLCYCLINES

This application claims priority from provisional Application Ser. No. 60/713,112, filed on Aug. 31, 2005, the entire disclosure of which is hereby incorporated by reference.

FIELD OF THE INVENTION

The present invention relates to 9-aminocarbonylsubstituted derivatives of glycylcyclines which are useful as antibiotic agents and exhibit antibacterial activity against a wide spectrum of organisms including organisms which are resistant to tetracyclines and other antibiotics.

BACKGROUND OF THE INVENTION

Since 1947 a variety of tetracycline antibiotics have been synthesized and described for the treatment of infectious diseases in man and animals. Tetracyclines inhibit protein synthesis by binding to the 30S subunit of the bacterial ribosome preventing binding of aminoacyl RNA (Chopra, Handbook of Experimental Pharmacology, Vol. 78, 317-392, Springer-Verlag, 1985). Resistance to tetracyclines has emerged among many clinically important microorganisms which limit the utility of these antibiotics. There are two major mechanisms of bacterial resistance to tetracyclines: a) energy-dependent efflux of the antibiotic mediated by proteins located in the cytoplasmic membrane which prevents intracellular accumulation of tetracycline (S. B. Levy, et al., Antimicrob. Agents Chemotherapy 33, 1373-1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, Mol. Microbiol, 4:151-156, 1990). The efflux mechanism of resistance is encoded by resistance determinants designated tetA-tetL. They are common in many Gram-negative bacteria (resistance genes Class A-E), such as Enterobacteriaceae, *Pseudomonas, Haemophilus* and *Aeromonas*, and in Gram-positive bacteria (resistance genes Class K and L), such as *Staphylococcus, Bacillus* and *Streptococcus*. The ribosomal protection mechanism of resistance is encoded by resistance determinants designated TetM, N and O, and is common in *Staphylococcus, Streptococcus, Campylobacter, Gardnerella, Haemophilus* and *Mycoplasma* (A. A. Salyers, B. S. Speers and N. B. Shoemaker, Mol. Microbiol, 4:151-156 1990).

A particularly useful tetracycline compound is 7-(dimethylamino)-6-demethyl-6-deoxytetracycline, known as minocycline (see U.S. Pat. No. 3,148,212, U.S. Pat. No. RE 26,253 and U.S. Pat. No. 3,226,436 discussed below). However, strains harboring the tetB (efflux in gram-negative bacteria) mechanism, but not tetK (efflux in *Staphylococcus*) are resistant to minocycline. Also, strains carrying tetM (ribosomal protection) are resistant to minocycline.

Duggar, U.S. Pat. No. 2,482,055, discloses the preparation of Aureomycin® by fermentation which have antibacterial activity. Growich et al., U.S. Pat. No. 3,007,965, disclose improvements to the fermentation preparation. Beereboom et al., U.S. Pat. No. 3,043,875 discloses tetracycline derivatives Boothe et al., U.S. Pat. No. 3,148,212, reissued as U.S. Pat. No. RE 26,253, and Petisi et al., U.S. Pat. No. 3,226,436, discloses tetracycline derivatives which are useful for treating bacterial infections. Blackwood et al., U.S. Pat. No. 3,200,149 discloses tetracycline derivatives which possess microbiological activity. Petisi et al., U.S. Pat. No. 3,338,963 discloses tetracycline compounds which have broad-spectrum antibacterial activity. Bitha et al., U.S. Pat. No. 3,341,585 discloses tetracycline compounds which have broad-spectrum antibacterial activity. Shu, U.S. Pat. No. 3,360,557 discloses 9-hydroxytetracyclines which have been found to possess antibacterial activity. Zambrano, U.S. Pat. No. 3,360,561 discloses a process for preparing 9-nitrotetracyclines. Martell et al., U.S. Pat. No. 3,518,306 discloses tetracyclines which possess in vivo antibacterial activity.

In U.S. Pat. No. 5,021,407 a method of overcoming the resistance of tetracycline resistant bacteria is disclosed. The method involves utilizing a blocking agent compound in conjunction with a tetracycline type antibiotic. This patent does not disclose novel tetracycline compounds which themselves have activity against resistant organisms. Described in U.S. Pat. No. 5,494,903 are 7-substituted-9-substituted amino-6-demethyl-6-deoxytetracyclines which have broad spectrum antibacterial activity.

Despite the advances being made to overcome the resistance of tetracycline resistant bacteria, there remains a need for newer and better antibiotics to overcome the increasing incidence of resistance. The present invention provides such antibiotics.

In summary, none of the above patents teach or suggest the novel derivatives of glycylcyclines of this application.

SUMMARY OF THE INVENTION

This invention is concerned with 9-aminocarbonylsubstituted derivatives of glycylcyclines represented by Formula I which have antibacterial activity; with methods of treating infectious diseases in humans and other animals when administering these new compounds; with pharmaceutical preparations containing these compounds; and with novel processes for the production of compounds of Formula I.

In accordance with the present invention, there is provided compounds represented by Formula (I);

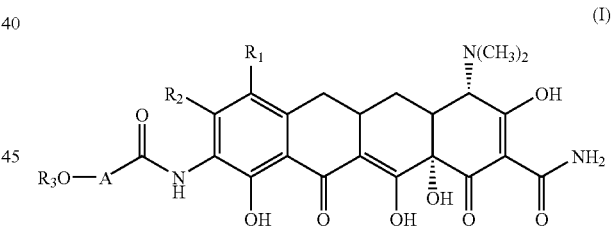

wherein:
A is a moiety

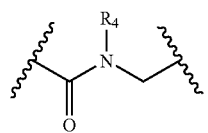

or is absent;
$R_1$ is selected from hydrogen, —OH, amino, —$NR_7R_8$, halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_2$ is selected from hydrogen, halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_3$ is the moiety $R_9$, $R_4$ is selected from hydrogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkynyl of 2 to 12 carbon atoms optionally substituted with 1 to 3 substituents independently selected from the group halogen, amino, cyano, alkyl, hydroxyl, and alkoxy, aryl of 6, 10 or 14 carbon atoms said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, N-(alkyl of 1 to 12 carbon atoms)-aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl of 7 to 13 carbon atoms optionally substituted, $SR^3$, heteroaryl optionally substituted and heteroarylcarbonyl optionally substituted;

$R_5$ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, 10 or 14 carbon atoms, aryloxy and N-(alkyl of 1 to 12 carbon atoms)-aryl, wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl, —$CH_2(CO)OCH_2$aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, alkenyl of 2 to 12 carbon atoms optionally substituted, heteroaryl optionally substituted, aryl of 6, 10 or 14 carbon atoms optionally substituted, alkynyl of 2 to 12 carbon atoms optionally substituted, cycloalkyl 3 to 6 ring atoms, aryl-CH═CH—, cycloalkyl-alkyl; and adamantyl;

$R_6$ is selected from hydrogen, alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and cycloalkyl of 3 to 6 carbon atoms;

$R_7$ and $R_8$ are each independently H or alkyl of 1 to 12 carbon atoms or $R_7$ and $R_8$ when optionally taken together with the nitrogen atom to which each is attached form a 3 to 8 membered heterocyclyl ring;

$R_9$ is aralkyl of 7 to 16 carbon atoms optionally substituted or alkyl of 1 to 12 carbon atoms;

$R_{10}$ is H or alkyl of 1 to 12 carbon atoms;

or a pharmaceutically acceptable salt thereof.

An embodiment of this invention provides compounds of Formula I wherein $R_1$ is —$NR_7R_8$, $R_7$ is hydrogen, $R_8$ is methyl, ethyl, n-propyl, n-butyl, 1-methylethyl, 1-methylpropyl, 2-methylpropyl or 1,1-dimethylethyl or a pharmaceutically acceptable salt thereof.

Another embodiment of this invention provides compounds of Formula I wherein $R_1$ is —$NR_7R_8$, $R_7$ is methyl or ethyl, $R_8$ is methyl, ethyl, n-propyl, 1-methylethyl, n-propyl, 1-methylpropyl, or 2-methylpropyl or a pharmaceutically acceptable salt thereof.

A further embodiment of this invention provides compounds of Formula I wherein $R_1$ is —$NR_7R_8$, $R_7$ and $R_8$ are taken together with the nitrogen atom to which each is attached form a 3 to 8 membered heterocyclyl ring or a pharmaceutically acceptable salt thereof.

Another embodiment of this invention provides compounds of Formula I wherein $R_2$ is H or a pharmaceutically acceptable salt thereof.

Another embodiment of this invention provides compounds of Formula I wherein A is a moiety

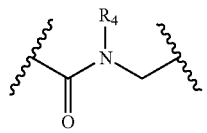

or a pharmaceutically acceptable salt thereof.

A further embodiment of this invention provides compounds of Formula I wherein A is absent or a pharmaceutically acceptable salt thereof.

A further embodiment of this invention provides compounds of Formula I wherein $R_3$ is a moiety

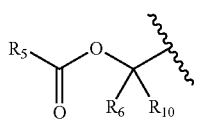

or a pharmaceutically acceptable salt thereof.

A further additional embodiment of this invention provides compounds of Formula I wherein $R_3$ is a moiety

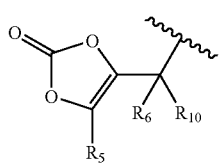

or a pharmaceutically acceptable salt thereof.

An embodiment of this invention provides compounds of Formula I wherein $R_3$ is a moiety

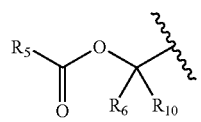

and $R_6$ and $R_{10}$ are H or a pharmaceutically acceptable salt thereof.

An additional embodiment of this invention provides compounds of Formula I wherein $R_3$ is a moiety

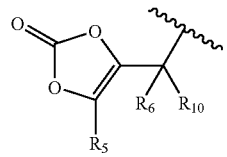

and $R_6$ and $R_{10}$ are H or a pharmaceutically acceptable salt thereof.

A further embodiment of this invention provides compounds of Formula I wherein $R_3$ is $R_9$ or a pharmaceutically acceptable salt thereof.

An additional embodiment of this invention provides compounds of Formula I wherein A is the moiety,

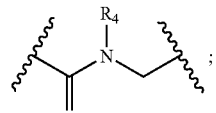

$R_3$ is the moiety

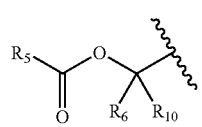 and $R_5$ is aryl of 6 carbon atoms or a pharmaceutically acceptable salt thereof.

A further embodiment of this invention provides compounds of Formula I wherein A is the moiety

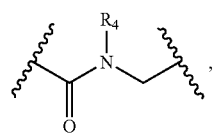

$R_3$ is the moiety,

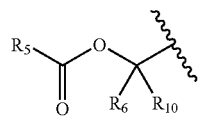

$R_4$ is 1,1-dimethylethyl and
$R_5$ is aryl of 6 carbon atoms or a pharmaceutically acceptable salt thereof.

An additional embodiment of this invention provides compounds of Formula I
wherein:
A is a moiety

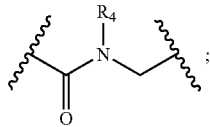

R₁ is —NR₇R₈;
R₂ is hydrogen;
R₃ is the moiety

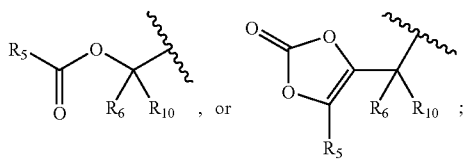

R₄ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, and aryloxy wherein said aryl and aryloxy is optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl;
R₅ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, 10 or 14 carbon atoms, and aryloxy wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, CH₃—C(O)—NH—, aralkyl, aryloxy, heterocyclyl and phenyl, aralkyl of 7 to 16 carbon atoms optionally substituted, aroyl, —CH₂(CO)OCH₂aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, heteroaryl optionally substituted, aryl of 6, 10 or 14 carbon atoms optionally substituted, cycloalkyl 3 to 6 ring atoms, aryl-CH═CH—, cycloalkyl-alkyl; and adamantyl;
R₆ is hydrogen;
R₇ and R₈ are each independently H or alkyl of 1 to 12 carbon atoms;
R₉ is aralkyl of 7 to 16 carbon atoms optionally substituted or alkyl of 1 to 12 carbon atoms;
R₁₀ is H;
or a pharmaceutically acceptable salt thereof.
Further embodiments of the invention are the following specifically preferred compounds of Formula I or pharmaceutically acceptable salts thereof:

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 2-methylpropanoate,
({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methoxybenzoate,
({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methylbenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-fluorobenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methylbenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methoxybenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclobutanecarboxylate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-fluorobenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl pivalate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-methylpropanoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl phenylacetate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl phenylacetate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl pivalate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl heptanoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl cyclobutanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl heptanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-tert-butylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 1,1'-biphenyl-4-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 3,5-dimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 1,1'-biphenyl-4-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 3,5-dimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-tert-butylbenzoate, 1-({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)ethyl acetate, ({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclohexanecarboxylate, ({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl cyclohexanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 3,3-dimethylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 3,3-dimethylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2,2-dimethylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl cyclopentylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl adamantane-1-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclopentylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl adamantane-1-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,3-dimethylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-tert-butylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,2-dimethylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-methylpropanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopentanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-methylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl heptanoate, and ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-methoxybenzoate.

Further embodiments of the invention are the following specifically preferred compounds of Formula I or pharmaceutically acceptable salts thereof:

benzyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate, ethyl 2-{[(5aR,6aS,7S,10aS)-9-(aminocarbonyl)-4,7-bis(dimethylamino)-1,8,10a,11-tetrahydroxy-10,12-dioxo-5, 5a,6,6a,7,10,10a,12-octahydrotetracen-2-yl]amino}-2-oxoethyl(propyl)carbamate, and isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate.

Additional further embodiments of the invention are the following specifically preferred compounds of Formula I or pharmaceutically acceptable salts thereof:

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-3-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-3-carboxylate, ({[(2-{[(5aR,6aS,7S,10aS)-9-(aminocarbonyl)-4,7-bis(dimethylamino)-1,8,10a,1-tetrahydroxy-10,12-dioxo-5,5a,6,6a,7,10,10a,12-octahydrotetracen-2-yl]amino}-2-oxoethyl)(butyl)amino]carbonyl}oxy)methyl 2-furoate, and ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-furoate.

Further embodiments of the invention are the following specifically preferred compounds of Formula I or pharmaceutically acceptable salts thereof:

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl propionate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclohexanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,5-dimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-fluorobenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methylbutanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopentylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(trifluoromethyl)benzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopropanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl adamantane-1-carboxylate, butyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate, isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate, methyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl pentanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclobutanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-cyclohexylpropanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl (4-fluorophenoxy)acetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclohexylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,6-dimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl phenylacetate, ({[(2-{[(5aR,6aS,7S,10aS)-9-(aminocarbonyl)-4,7-bis(dimethylamino)-1,8,10a,11-tetrahydroxy-10,12-dioxo-5,5a, 6,6a,7,10,10a,12-octahydrotetracen-2-yl]amino}-2-oxo-
ethyl)(tert-butyl)amino]carbonyl}oxy)methyl pivalate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 1,1'-
biphenyl-4-carboxylate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
1-naphthoate,
({[(2-{[(5aR,6aS,7S,10aS)-9-(aminocarbonyl)-4,7-bis(dim-
ethylamino)-1,8,10a,1-tetrahydroxy-10,12-dioxo-5,5a,6,
6a,7,10,10a,12-octahydrotetracen-2-yl]amino}-2-oxoet-
hyl)(tert-butyl)amino]carbonyl}oxy)methyl 2-naphthoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 2,6-
difluorobenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
2-fluorobenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
2-(trifluoromethyl)benzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 1,1'-
biphenyl-2-carboxylate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 2,4,6-
trimethylbenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
4-isopropoxybenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 3,4,5-
trimethoxybenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 3,5-
dimethoxybenzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl (2E)-3-
phenylprop-2-enoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl[3,5-bis
(trifluoromethyl)phenyl]acetate, ({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
4-(heptyloxy)benzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl 2-(2-
phenylethyl)benzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
4-(dodecyloxy)benzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
4-(acetylamino)benzoate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl anthracene-
9-carboxylate,
({[(2-{[(5aR,6aS,7S,10aS)-9-(aminocarbonyl)-4,7-bis(dim-
ethylamino)-1,8,10a,11-tetrahydroxy-10,12-dioxo-5,5a,
6,6a,7,10,10a,12-octahydrotetracen-2-yl]amino}-2-oxo-
ethyl)(tert-butyl)amino]carbonyl}oxy)methyl
4-benzoylbenzoate, and
({([(2-{[(5aR,6aS,7S,10aS)-9-(aminocarbonyl)-4,7-bis
(dimethylamino)-1,8,10a,11-tetrahydroxy-10,12-dioxo-5,
5a,6,6a,7,10,10a,12-octahydrotetracen-2-yl]amino}-2-
oxoethyl)(tert-butyl)amino]carbonyl}oxy)methyl
diphenylacetate.

Additional further embodiments of the invention are the
following specifically preferred compounds of Formula I or
pharmaceutically acceptable salts thereof:

[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl 4-fluorobenzoate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl 3,5-dimethylbenzoate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl pivalate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl 3,3-dimethylbutanoate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl 2,2-dimethylbutanoate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl 2-ethylbutanoate,
[({[(5aR,6aS,7S,10aS)-9-(aminocarbonyl)-4,7-bis(dimethy-
lamino)-1,8,10a,11-tetrahydroxy-10,12-dioxo-5,5a,6,6a,
7,10,10a,12-octahydrotetracen-2-yl]amino}carbonyl)
oxy]methyl thiophene-2-carboxylate,

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl cyclopentylacetate, and
[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 4-tert-butylbenzoate.

Further embodiments of the invention are the following specifically preferred compounds of Formula I or pharmaceutically acceptable salts thereof:
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1H-indole-2-carboxylate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl nicotinate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl isonicotinate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-pyrrolidin-1-ylbenzoate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methyl-1-benzofuran-2-carboxylate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-methyl-1H-indole-3-carboxylate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl quinoline-2-carboxylate,
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-benzofuran-2-carboxylate, and
({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl-1-methyl-1H-pyrrole-2-carboxylate.

Further embodiments of the invention are the following specifically preferred compounds of Formula I or pharmaceutically acceptable salts thereof:
(5-methyl-2-oxo-1,3-dioxol-4-yl)methyl 2-{[(7S,10aR)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate,
(5-methyl-2-oxo-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate,
(2-oxo-5-phenyl-1,3-dioxol-4-yl)methyl 2-{[(7R,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate,
[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate,
(2-oxo-5-phenyl-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate and
[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate.

An additional embodiment of this invention are compounds represented by Formula (II):

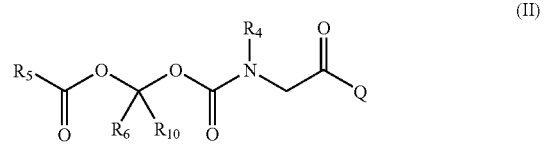

wherein:
$R_4$ is selected from hydrogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkynyl of 2 to 12 carbon atoms optionally substituted with 1 to 3 substituents independently selected from the group halogen, amino, cyano, alkyl, hydroxyl, and alkoxy, aryl of 6, 10 or 14 carbon atoms said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, N-(alkyl of 1 to 12 carbon atoms)-aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl of 7 to 13 carbon atoms optionally substituted, $SR^3$, heteroaryl optionally substituted and heteroarylcarbonyl optionally substituted;
$R_5$ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, 10 or 14 carbon atoms, aryloxy and N-(alkyl of 1 to 12 carbon atoms)-aryl, wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl, —$CH_2$(CO)$OCH_2$aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, alkenyl of 2 to 12 carbon atoms optionally substituted, heteroaryl optionally substituted, aryl of 6, 10 or 14 carbon atoms optionally substituted, alkynyl of 2 to 12 carbon atoms optionally substituted, cycloalkyl 3 to 6 ring atoms, aryl-CH═CH—, cycloalkyl-alkyl; and adamantyl;

$R_6$ is selected from hydrogen, alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and cycloalkyl of 3 to 6 carbon atoms;

$R_{10}$ is H or alkyl of 1 to 12 carbon atoms;

Q is —$OR_{11}$, Cl, Br or I;

$R_{11}$ is H, benzyl optionally substituted with nitro or a moiety of the formula

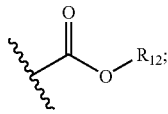

$R_{12}$ is alkyl of 1 to 6 carbon atoms.

The compounds having Formula II are useful as chemical intermediates for making the compounds having formula I and the pharmaceutically acceptable salt thereof wherein: A is a moiety

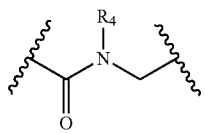

and $R_3$ is the moiety

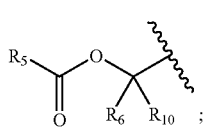

where $R_4$ and $R_5$ are as defined above.

An embodiment of the invention provides compounds of Formula II wherein $R_4$ is t-butyl, $R_5$ is alkyl of 1 to 6 carbon atoms, and $R_{11}$ is benzyl optionally substituted with nitro.

Another embodiment of the invention provides compounds of Formula II wherein $R_4$ is alkyl of 1 to 6 carbon atoms, $R_5$ is phenyl optionally substituted and $R_{11}$ is benzyl optionally substituted with nitro.

An embodiment of the invention provides compounds of Formula II wherein $R_5$ is alkyl of 1 to 6 carbon atoms, $R_4$ is t-butyl and $R_{11}$ is H.

A further embodiment of the invention provides compounds of Formula II wherein $R_5$ is alkyl of 1 to 6 carbon atoms, $R_4$ is t-butyl, Q is —$OR_{11}$, $R_{11}$ is

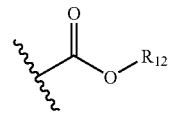

and $R_{12}$ is alkyl of 1 to 6 carbon atoms.

Another embodiment of the invention provides compounds of Formula II wherein $R_6$ and $R_{10}$ are H.

Further embodiments of the invention provides the following specifically preferred compounds of Formula II or pharmaceutically acceptable salts thereof.

({[[2-(benzyloxy)-2-oxoethyl](tert-butyl)amino] carbonyl}oxy)methyl 4-tert-butylbenzoate,
({[[2-(benzyloxy)-2-oxoethyl](tert-butyl)amino] carbonyl}oxy)methyl 2,2-dimethylbutanoate,
({[[2-(benzyloxy)-2-oxoethyl](tert-butyl)amino] carbonyl}oxy)methyl 2-methylpropanoate,
({[[2-(benzyloxy)-2-oxoethyl](tert-butyl)amino] carbonyl}oxy)methyl cyclopentanecarboxylate,
({[[2-(benzyloxy)-2-oxoethyl](tert-butyl)amino] carbonyl}oxy)methyl 4-methylbenzoate,
({[[2-(benzyloxy)-2-oxoethyl](tert-butyl)amino] carbonyl}oxy)methyl heptanoate,
({[[2-(benzyloxy)-2-oxoethyl](tert-butyl)amino] carbonyl}oxy)methyl propionate,
({[[2-(benzyloxy)-2-oxoethyl](tert-butyl)amino] carbonyl}oxy)methyl cyclohexanecarboxylate,
({[[2-(benzyloxy)-2-oxoethyl](tert-butyl)amino] carbonyl}oxy)methyl 3,5-dimethylbenzoate,
({[[2-(benzyloxy)-2-oxoethyl](tert-butyl)amino] carbonyl}oxy)methyl 4-fluorobenzoate,
({[[2-(benzyloxy)-2-oxoethyl](tert-butyl)amino] carbonyl}oxy)methyl 3-methylbutanoate,
benzyl N-(tert-butyl)-N-({[(cyclopentylacetyl)oxy] methoxy}carbonyl)glycinate,
({[[2-(benzyloxy)-2-oxoethyl](tert-butyl)amino] carbonyl}oxy)methyl 4-(trifluoromethyl)benzoate,
({[[2-(benzyloxy)-2-oxoethyl](tert-butyl)amino] carbonyl}oxy)methyl cyclopropanecarboxylate, ({[[2-(benzyloxy)-2-oxoethyl](tert-butyl)amino]carbonyl}oxy) methyl adamantane-1-carboxylate,
({[[2-(benzyloxy)-2-oxoethyl](tert-butyl)amino] carbonyl}oxy)methyl pentanoate,
({[[2-(benzyloxy)-2-oxoethyl](tert-butyl)amino] carbonyl}oxy)methyl cyclobutanecarboxylate,
({[[2-(benzyloxy)-2-oxoethyl](tert-butyl)amino] carbonyl}oxy)methyl 3-cyclohexylpropanoate,
benzyl N-(tert-butyl)-N-[({[(4-fluorophenoxy)acetyl] oxy}methoxy)carbonyl]glycinate, benzyl N-(tert-butyl)-N-({[(cyclohexylacetyl)oxy]methoxy}carbonyl)glycinate, ({[[2-(benzyloxy)-2-oxoethyl](tert-butyl)amino]
carbonyl}oxy)methyl 2,6-dimethylbenzoate,
benzyl N-(tert-butyl)-N-({[(phenylacetyl)oxy]
methoxy}carbonyl)glycinate,
({[[2-(benzyloxy)-2-oxoethyl](tert-butyl)amino]
carbonyl}oxy)methyl pivalate,
({[[2-(benzyloxy)-2-oxoethyl](tert-butyl)amino]
carbonyl}oxy)methyl 1-benzofuran-2-carboxylate,
({[[2-(benzyloxy)-2-oxoethyl](tert-butyl)amino]
carbonyl}oxy)methyl 1-methyl-1H-pyrrole-2-carboxylate,
({[[2-(benzyloxy)-2-oxoethyl](tert-butyl)amino]
carbonyl}oxy)methyl 1,1'-biphenyl-4-carboxylate,
({[[2-(benzyloxy)-2-oxoethyl](tert-butyl)amino]
carbonyl}oxy)methyl 4-methoxybenzoate,
({[[2-(benzyloxy)-2-oxoethyl](tert-butyl)amino]
carbonyl}oxy)methyl 1H-indole-2-carboxylate,
benzyl N-(tert-butyl)-N-({[(diphenylacetyl)oxy]
methoxy}carbonyl)glycinate,
({[[2-(benzyloxy)-2-oxoethyl](tert-butyl)amino]
carbonyl}oxy)methyl 1-naphthoate,
({[[2-(benzyloxy)-2-oxoethyl](tert-butyl)amino]
carbonyl}oxy)methyl 2-naphthoate,
({[[2-(benzyloxy)-2-oxoethyl](tert-butyl)amino]
carbonyl}oxy)methyl 1-methyl-1H-indole-3-carboxylate,
({[[2-(benzyloxy)-2-oxoethyl](tert-butyl)amino]
carbonyl}oxy)methyl quinoline-2-carboxylate,
({[[2-(benzyloxy)-2-oxoethyl](tert-butyl)amino]
carbonyl}oxy)methyl nicotinate,
({[[2-(benzyloxy)-2-oxoethyl](tert-butyl)amino]
carbonyl}oxy)methyl isonicotinate,
({[[2-(benzyloxy)-2-oxoethyl](tert-butyl)amino]
carbonyl}oxy)methyl 2,6-difluorobenzoate,
({[[2-(benzyloxy)-2-oxoethyl](tert-butyl)amino]
carbonyl}oxy)methyl 2-fluorobenzoate,
({[[2-(benzyloxy)-2-oxoethyl](tert-butyl)amino]
carbonyl}oxy)methyl 2-(trifluoromethyl)benzoate,
({[[2-(benzyloxy)-2-oxoethyl](tert-butyl)amino]
carbonyl}oxy)methyl 4-(1H-pyrrol-1-yl)benzoate,
({[[2-(benzyloxy)-2-oxoethyl](tert-butyl)amino]
carbonyl}oxy)methyl 1,1'-biphenyl-2-carboxylate,
({[[2-(benzyloxy)-2-oxoethyl](tert-butyl)amino]
carbonyl}oxy)methyl 2,4,6-trimethylbenzoate,
({[[2-(benzyloxy)-2-oxoethyl](tert-butyl)amino]
carbonyl}oxy)methyl 4-isopropoxybenzoate,
({[[2-(benzyloxy)-2-oxoethyl](tert-butyl)amino]
carbonyl}oxy)methyl 3,4,5-trimethoxybenzoate,
({[[2-(benzyloxy)-2-oxoethyl](tert-butyl)amino]
carbonyl}oxy)methyl 3,5-dimethoxybenzoate,
3-phenyl-acrylic acid (benzyloxycarbonylmethyl-tert-butyl-carbamoyloxy)-methyl ester,
({[[2-(benzyloxy)-2-oxoethyl](tert-butyl)amino]
carbonyl}oxy)methyl 3-methyl-1-benzofuran-2-carboxylate,
benzyl N-{([({[3,5-bis(trifluoromethyl)phenyl]acetyl}oxy)
methoxy]carbonyl}-N-(tert-butyl)glycinate,
({[[2-(benzyloxy)-2-oxoethyl](tert-butyl)amino]
carbonyl}oxy)methyl 4-(heptyloxy)benzoate,
({[[2-(benzyloxy)-2-oxoethyl](tert-butyl)amino]
carbonyl}oxy)methyl 2-(2-phenylethyl)benzoate,
({[[2-(benzyloxy)-2-oxoethyl](tert-butyl)amino]
carbonyl}oxy)methyl 4-(dodecyloxy)benzoate,
({[[2-(benzyloxy)-2-oxoethyl](tert-butyl)amino]
carbonyl}oxy)methyl 4-(acetylamino)benzoate,
({[[2-(benzyloxy)-2-oxoethyl](tert-butyl)amino]
carbonyl}oxy)methyl anthracene-9-carboxylate and
({[[2-(benzyloxy)-2-oxoethyl](tert-butyl)amino]
carbonyl}oxy)methyl 4-benzoylbenzoate.

Additional embodiments of the invention are the following specifically preferred compounds of Formula II or pharmaceutically acceptable salts thereof.
N-(tert-butyl)-N-({[(4-tert-butylbenzoyl)oxy]
methoxy}carbonyl)glycine,
N-(tert-butyl)-N-{[(isobutyryloxy)methoxy]
carbonyl}glycine,
N-(tert-butyl)-N-({[(cyclopentylcarbonyl)oxy]
methoxy}carbonyl)glycine,
N-(tert-butyl)-N-({[(4-methylbenzoyl)oxy]
methoxy}carbonyl)glycine,
N-(tert-butyl)-N-{[(heptanoyloxy)methoxy]
carbonyl}glycine,
N-(tert-butyl)-N-{[(propionyloxy)methoxy]
carbonyl}glycine,
N-(tert-butyl)-N-({[(cyclohexylcarbonyl)oxy]
methoxy}carbonyl)glycine,
N-(tert-butyl)-N-({[(3,5-dimethylbenzoyl)oxy]
methoxy}carbonyl)glycine,
N-(tert-butyl)-N-({[(4-fluorobenzoyl)oxy]
methoxy}carbonyl)glycine,
N-(tert-butyl)-N-({[(3-methylbutanoyl)oxy]
methoxy}carbonyl)glycine,
N-(tert-butyl)-N-({[(cyclopentylacetyl)oxy]
methoxy}carbonyl)glycine,
N-(tert-butyl)-N-[({[4-(trifluoromethyl)benzoyl]
oxy}methoxy)carbonyl]glycine,
N-(tert-butyl)-N-({[(cyclopropylcarbonyl)oxy]
methoxy}carbonyl)glycine,
N-({[(1-adamantylcarbonyl)oxy]methoxy}carbonyl)-N-(tert-butyl)glycine,
N-(tert-butyl)-N-{[(pentanoyloxy)methoxy]
carbonyl}glycine,
N-(tert-butyl)-N-({[(cyclobutylcarbonyl)oxy]
methoxy}carbonyl)glycine,
N-(tert-butyl)-N-({[(3-cyclohexylpropanoyl)oxy]
methoxy}carbonyl)glycine,
N-(tert-butyl)-N-[({[(4-fluorophenoxy)acetyl]
oxy}methoxy)carbonyl]glycine
N-(tert-butyl)-N-({[(cyclohexylacetyl)oxy]
methoxy}carbonyl)glycine,
N-(tert-butyl)-N-({[(2,6-dimethylbenzoyl)oxy]
methoxy}carbonyl)glycine,
N-(tert-butyl)-N-({[(phenylacetyl)oxy]methoxy}carbonyl)
glycine,
N-(tert-butyl)-N-({[(2,2-dimethylpropanoyl)oxy]
methoxy}carbonyl)glycine,
N-({[(1-benzofuran-2-ylcarbonyl)oxy]methoxy}carbonyl)-
N-(tert-butyl)glycine,
N-(tert-butyl)-N-[({[(1-methyl-1H-pyrrol-2-yl)carbonyl]
oxy}methoxy)carbonyl]glycine,
N-({[(1,1'-biphenyl-4-ylcarbonyl)oxy]methoxy}carbonyl)-
N-(tert-butyl)glycine,
N-(tert-butyl)-N-({[(4-methoxybenzoyl)oxy]
methoxy}carbonyl)glycine,
N-(tert-butyl)-N-({[(1H-indol-2-ylcarbonyl)oxy]
methoxy}carbonyl)glycine,
N-(tert-butyl)-N-({[(diphenylacetyl)oxy]
methoxy}carbonyl)glycine,
N-(tert-butyl)-N-{[(1-naphthoyloxy)methoxy]
carbonyl}glycine,
N-(tert-butyl)-N-{[(2-naphthoyloxy)methoxy]
carbonyl}glycine,
N-(tert-butyl)-N-[({[(1-methyl-1H-indol-3-yl)carbonyl]
oxy}methoxy)carbonyl]glycine,
N-(tert-butyl)-N-({[(quinolin-2-ylcarbonyl)oxy]
methoxy}carbonyl)glycine, N-(tert-butyl)-N-({[(pyridin-3-ylcarbonyl)oxy]
methoxy}carbonyl)glycine,
N-(tert-butyl)-N-{[(isonicotinoyloxy)methoxy]
carbonyl}glycine,
N-(tert-butyl)-N-({[(2,6-difluorobenzoyl)oxy]
methoxy}carbonyl)glycine,
N-(tert-butyl)-N-({[(2-fluorobenzoyl)oxy]
methoxy}carbonyl)glycine,
N-(tert-butyl)-N-[({[2-(trifluoromethyl)benzoyl]
oxy}methoxy)carbonyl]glycine,
N-(tert-butyl)-N-({[(4-pyrrolidin-1-ylbenzoyl)oxy]
methoxy}carbonyl)glycine,
N-({[(1,1'-biphenyl-2-ylcarbonyl)oxy]methoxy}carbonyl)-
N-(tert-butyl)glycine,
N-(tert-butyl)-N-({[(mesitylcarbonyl)oxy]
methoxy}carbonyl)glycine,
N-(tert-butyl)-N-({[(4-isopropoxybenzoyl)oxy]
methoxy}carbonyl)glycine,
N-(tert-butyl)-N-({[(3,4,5-trimethoxybenzoyl)oxy]
methoxy}carbonyl)glycine,
N-(tert-butyl)-N-({[(3,5-dimethoxybenzoyl)oxy]
methoxy}carbonyl)glycine,
N-(tert-butyl)-N-[({[(2E)-3-phenylprop-2-enoyl]
oxy}methoxy)carbonyl]glycine,
N-(tert-butyl)-N-[({[(3-methyl-1-benzofuran-2-yl)carbonyl]
oxy}methoxy)carbonyl]glycine,
N-{[({[3,5-bis(trifluoromethyl)phenyl]acetyl}oxy)meth-
oxy]carbonyl}-N-(tert-butyl)glycine,
N-(tert-butyl)-N-[({[4-(heptyloxy)benzoyl]oxy}methoxy)
carbonyl]glycine,
N-(tert-butyl)-N-[({[2-(2-phenylethyl)benzoyl]
oxy}methoxy)carbonyl]glycine,
N-(tert-butyl)-N-[({[4-(dodecyloxy)benzoyl]oxy}methoxy)
carbonyl]glycine,
N-[({[4-(acetylamino)benzoyl]oxy}methoxy)carbonyl]-N-
(tert-butyl)glycine,
N-({[(9-anthrylcarbonyl)oxy]methoxy}carbonyl)-N-(tert-
butyl)glycine and
N-({[(4-benzoylbenzoyl)oxy]methoxy}carbonyl)-N-(tert-
butyl)glycine A further embodiment of the invention is the following specifically preferred compound of Formula II or pharmaceutically acceptable salts thereof.

3,3-Dimethyl-butyric acid [tert-butyl-(2-isobutoxycarbonyloxy-2-oxo-ethyl)-carbamoyloxy)-methyl ester.

DEFINITIONS

For the compounds of the invention defined above and referred to herein, unless otherwise noted, the following terms are defined:

The term alkyl means a straight or branched alkyl moiety of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl. In some embodiments of the invention alkyl is a moiety of 1 to 6 carbon atoms. In other embodiments of the invention alkyl is a moiety of 1 to 3 carbon atoms. In other embodiments of the invention alkyl is 1,1-dimethylethyl also termed t-butyl. In some embodiments of the invention when alkyl is a methyl group wherein optional substitution is two independent phenyl rings. Non-limiting examples of alkyl are methyl, ethyl, n-propyl, 1-methylethyl, n-butyl, 1-methylpropyl, 2-methylpropyl and 1,1-dimethylethyl.

The term alkenyl means a straight or branched carbon chain of 2 to 12 carbon atoms having at least one site of unsaturation optionally independently substituted with 1 to 3 substituents selected from the group optionally independently substituted with 1 to 3 substituents selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl. In some embodiments of the invention alkenyl is a vinyl moiety $CH_2$=CH—.

As used herein the term alkoxy refers to alkyl-O— wherein alkyl is hereinbefore defined. Non limiting examples include: methoxy and ethoxy.

As used herein the term aryl means an aromatic moiety having 6, 10 or 14 carbon atoms preferably 6 to 10 carbon atoms, optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl. In particular, aryl is phenyl or naphthyl optionally substituted with 1 to 3 substituents.

The term aralkyl as used herein of 7 to 16 carbon atoms means an alkyl substituted with an aryl group in which the aryl and alkyl group are as defined herein. Non-limiting exemplary aralkyl groups include benzyl and phenethyl and the like.

Perhaloalkyl as used herein means an alkyl moiety of 1 to 6 carbon atoms in which each hydrogen atom is substituted with a halogen atom, an exemplary example is trifluoromethyl.

Phenyl as used herein refers to a 6-membered carbon aromatic ring.

As used herein the term alkynyl includes both straight chain and branched moieties containing 2 to 12 carbon atoms having at least one carbon to carbon triple bond optionally substituted with 1 to 3 substituents independently selected from the group halogen, amino, cyano, alkyl of 1 to 12 carbon atoms, hydroxyl, and alkoxy of 1 to 12 carbon atoms.

As used herein the term halogen or halo means F, Cl, Br or I.

As used herein the term cycloalkyl means a saturated monocyclic ring having from 3 to 6 carbon atoms. Exemplary cycloalkyl rings include but are not limited to cyclopropyl, cyclobutyl, cyclopentyl, and cyclohexyl. In an embodiment of the invention cycloalkyl is a moiety of 5 or 6 carbon atoms.

The term aroyl means an aryl-C(O)— group in which the aryl group is as previously defined. Non-limiting examples include benzoyl and naphthoyl.

The term heteroaryl means an aromatic heterocyclic, monocyclic ring of 5 or 6 ring atoms containing 1 to 4 heteroatoms independently selected from O, N and S or bicyclic aromatic rings of 8 to 20 ring atoms containing 1 to 4 heteroatoms independently selected from O, N and S. Heteroaryl rings may optionally be substituted with 1 to 3 substitutents independently selected from the group alkyl, halogen, cyano, nitro, hydroxy, amino, alkylamino, dialkylamino, alkoxy, aryloxy, —$CH_2OCOCH_3$ and carboxy. Non-limiting heteroaryl moieties optionally substituted include: furanyl, benzofuranyl, benzothienyl, thienyl, pyridinyl, quinolinyl, tetrazolyl, imidazo, thiazolyl and the like.

Where terms are used in combination, the definition for each individual part of the combination applies unless defined otherwise. For instance, aralkyl refers to an aryl group, and alkyl refers to the alkyl group as defined above. Also, aryloxy refers to a arylO— group.

The term heteroarylcarbonyl means a heteroaryl-C(O)— group in which the heteroaryl group is as previously defined.

The term heterocyclyl as used herein represents a saturated ring of 3 to 8 ring atoms containing 1 to 3 heteroatoms selected from nitrogen, oxygen and sulfur. In some embodiments of the invention a saturated ring of 5 or 6 ring atoms is preferred. Representative examples are pyrrolidyl, piperidyl, piperazinyl, morpholinyl, thiomorpholinyl, aziridinyl, tetrahydrofuranyl and the like.

The term alkylheterocyclyl means an alkyl-heterocyclyl group in which the alkyl and heterocyclyl group are independently previously defined. Non-limiting exemplary alkylheterocyclyl groups include moieties of the formulae:

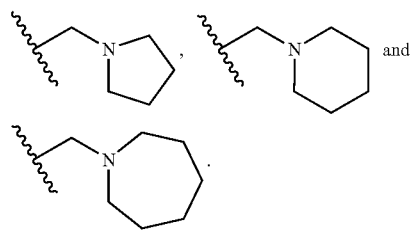

Some of the compounds of Formula (I) may also exist in their tautomeric forms. Such forms although not explicitly indicated in the above formula are intended to be included within the scope of the present invention. For instance, compounds of Formula (I) which exist as tautomers are depicted below:

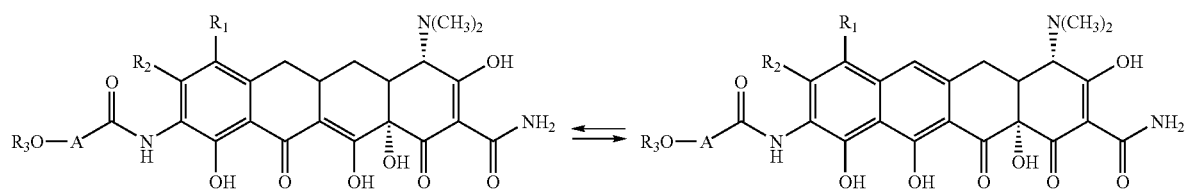

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

Proton sponge is [1,8-bis(dimethylamino)naphthalene, N,N,N',N'-tetramethyl-1,8-naphthalenediamine].

Alkali metal carbonate includes lithium, potassium and sodium carbonate.

DMPU is 1,3-dimethyl-3,4,5,6-tetrahydro-2(1H)-pyrimidinone.

N-butyl-glycylcycline (N-bu-glycyl) is

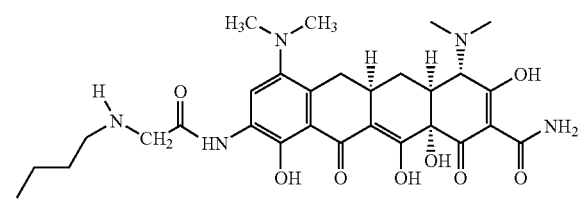

N-propyl-glycylcycline (N-prop-glycyl) is

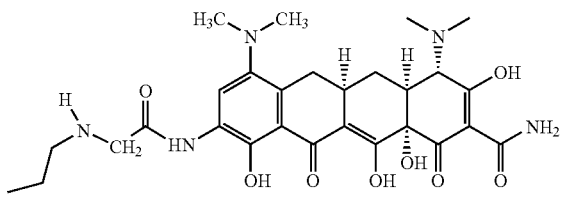

DESCRIPTION OF THE PREFERRED EMBODIMENTS

The compounds of this invention may be prepared according to the following schemes: (1) from commercially available starting materials or: (2) from known starting materials which can be prepared as described in literature procedures or: (3) from new intermediates described in the schemes and experimental procedures.

The synthesis of acyloxy intermediate 8 is shown in Scheme 1. Reaction of amine $R_4NH_2$, preferably t-butylamine, with ester 1 provides the substituted amino ester 2. Preparation of the intermediate 4 is accomplished by using Proton Sponge as base to effect the acylation of substituted amino ester 2 with chloromethyl chloroformate 3. Treatment of intermediate 4 with the tetrabutylammonium salt 5 of carboxylic acids gives the benzyl protected acyloxy intermediate 6. The benzyl protecting group is removed by catalytic reduction to give carboxylic acid 7 which is activated to a mixed anhydride with chloroformate $ClCO_2R_{12}$ where $R_{12}$ is alkyl of 1 to 6 carbon atoms, for example iso-butyl chloroformate to give acyloxycarbamate intermediate 8. In an alternate route, silyl esters may optionally be used in place of the benzyl ester of intermediate 4, treating with the appropriate carboxylic acid followed by deblocking the silyl ester with tetrabutylammonium fluoride or magnesium bromide to afford carboxylic acid 7. Optionally, carboxylic acid 7 may be activated through the use of coupling agents not limited to di-t-butyl dicarbonate ($Boc_2O$); e.g., benzotriazole-1-yl-oxy-tris-(dimethylamino)-phosphonium hexafluorophosphate (also known asBop); benzotriazole-1-yl-oxy-tris-pyrrolidino-phosphonium hexafluorophosphate (also known as PyBop); O-benzotriazole-N,N,N',N'-tetramethyl-uronium-hexafluoro-phosphate (HBTU); Bromotris-pyrrolidino-phosphonium hexafluorophosphate; 2-Chloro-N-methylpyridinium iodide (CMPI); dicyclohexylcarbodiimide (DCC); 1,3-diisopropylcarbodiimide (DIC); 1-(3-dimethylaminopropyl)-3-ethyl-carbodiimide hydrochloride (EDC); or Carbonyl diimidazole.

SCHEME 1

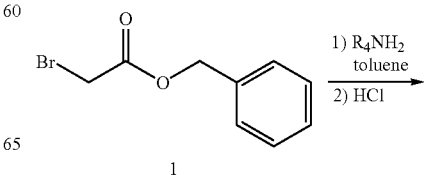

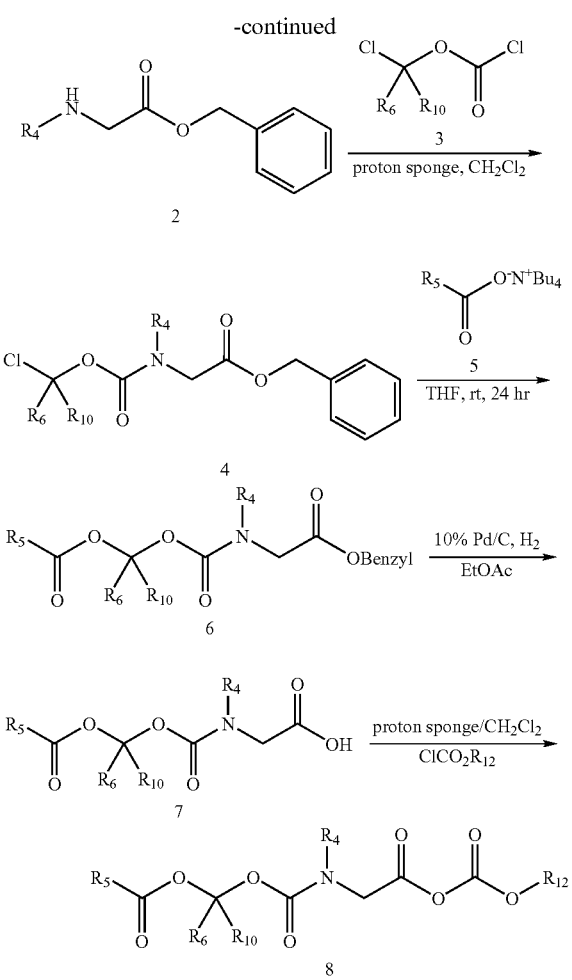

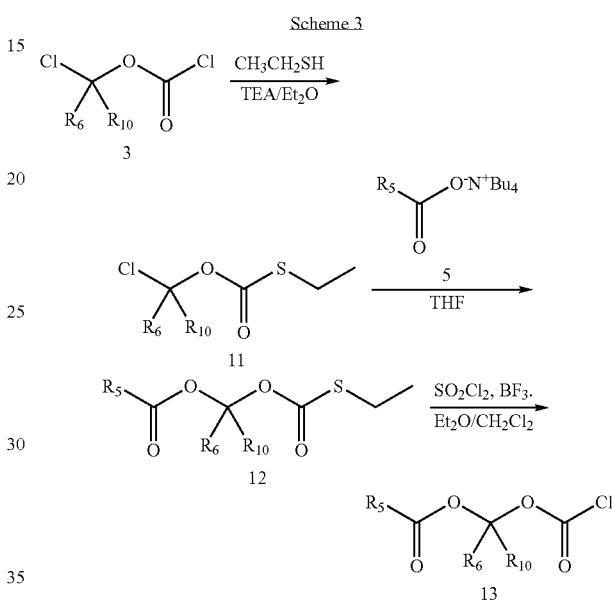

Additional acyloxy carbamate compounds may be synthesized via routes as shown in Schemes 3 and 4. Treatment of chloromethyl chloroformate 3 with ethanethiol in the presence of triethylamine (TEA) gives carbonothioate 11. Compound 12 is prepared by reacting carbonothioate 11 with carboxylic acid tetrabutylammonium salt 5 in tetrahydrofuran. Chlorination of compound 12 with sulfuryl chloride in the presence of catalytic amount of boron trifluoroetherate affords chloro intermediate 13 (using the methods described in M. Folkmann and F. J. Lund, Synthesis, December 1990, 1159-1166).

As shown in Scheme 2, reaction of activated acyloxycarbamate intermediate 8 with 7,8-disubstituted-9-aminotetracycline 9 in the presence of triethylamine and DMPU gives acyloxycarbamate 10.

As further seen in Scheme 4 acyloxycarbamates 16 and 17 where $R_4$ is preferably n-butyl or n-propyl are synthesized by treatment of either 14 or 15 where $R_4$ is preferably n-butyl or n-propyl with the chloro intermediate 13 to give acyloxycarbamates 16 and 17 respectively.

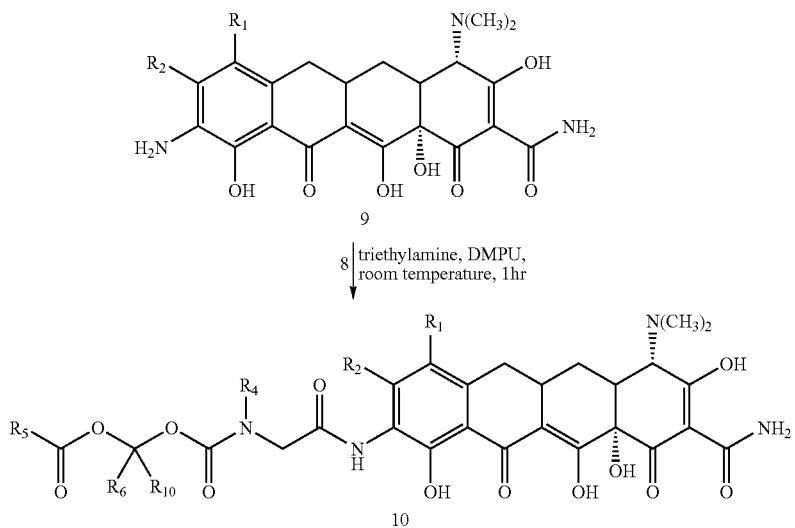

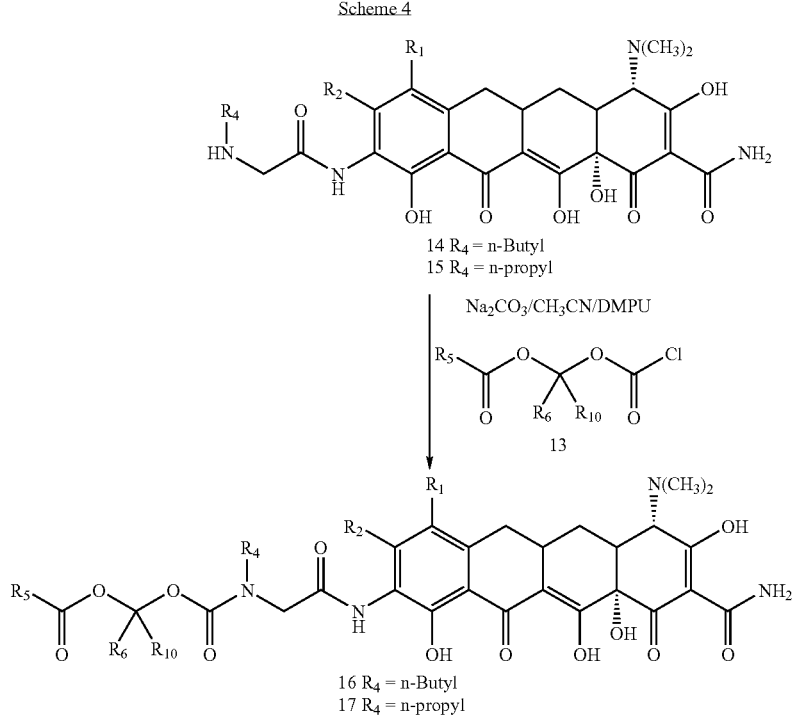

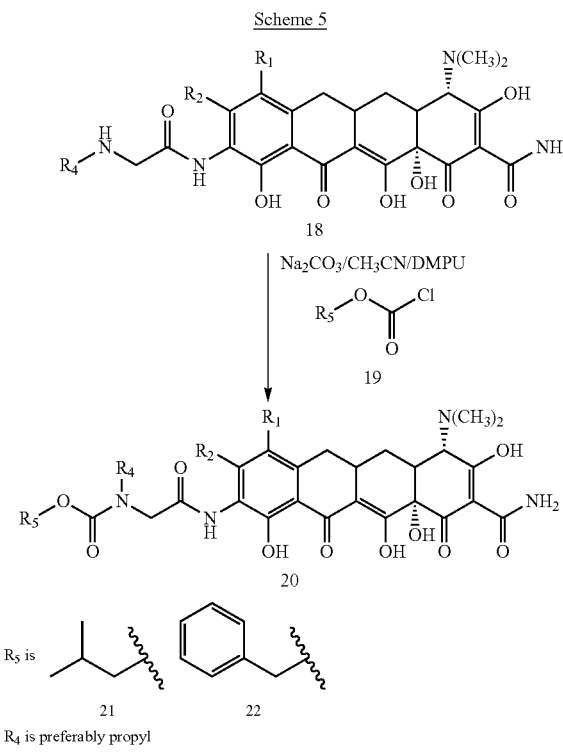

As shown in Scheme 5, carbamates of glycylcycline where $R_4$ is preferably propyl 18 may also be prepared by reaction with chloro intermediate 19 in the presence of an alkali metal carbonate preferably sodium carbonate, and DMPU in acetonitrile to afford preferred compounds (21 and 22).

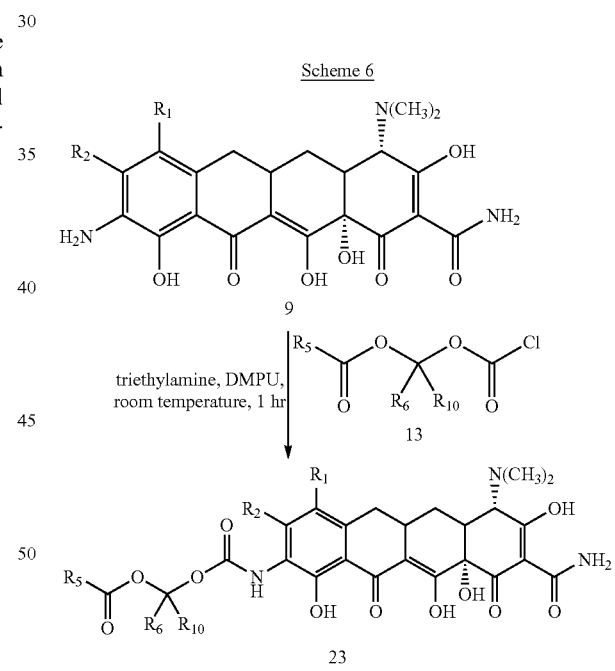

As shown in Scheme 6, reaction of chloro intermediate 13 with 7,8-disubstituted-9-aminotetracycline 9 in the presence of triethylamine and DMPU gives carbamate 23.

As further shown in Scheme 7, compounds of Formula I may generally be prepared by removal of the benzyl protecting group from benzyl protected acyloxy intermediate 24 to give carboxylic acid 25 which is activated to a mixed anhydride with a chloroformate $ClCO_2R_{12}$ where $R_{12}$ is alkyl of 1 to 6 carbon atoms, for example iso-butyl chloroformate to give acyloxycarbamate intermediate 26. Further reaction of 7,8-disubstituted-9-aminotetracycline 9 with acyloxycarbamate mixed anhydride intermediate 26 in the presence of triethylamine and DMPU affords compounds of Formula (I).

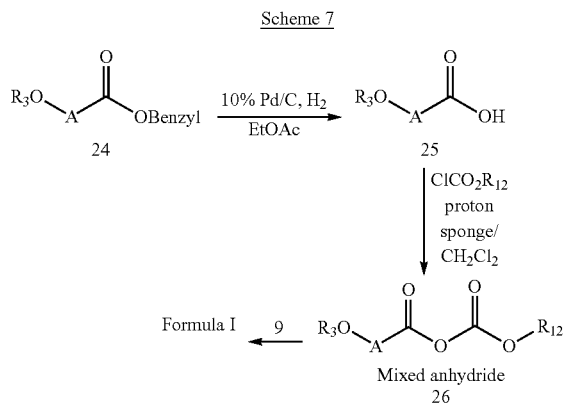

Scheme 7

Mixed anhydride 26

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have center of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

The compounds of the invention may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411-415, 1989). Preferably, the compounds of the invention are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate alkylsulfonate or arylsulfonate. In all cases, the salt formation occurs with the C(4)-dimethylamino group. The salts are preferred for oral and parenteral administration.

Standard Pharmacological Test Procedures
Methods for In Vitro Antibacterial Evaluation
The Minimum Inhibitory Concentration (MIC)

Antimicrobial susceptibility testing. The in vitro activities of the antibiotics are determined by the broth microdilution method as recommended by the National Committee for Clinical Laboratory Standards (NCCLS) (1). Mueller-Hinton II broth (MHBII)(BBL Cockeysville, Md.) is the medium employed in the testing procedures. Microtiter plates containing serial dilutions of each antimicrobial agent are inoculated with each organism to yield the appropriate density ($10^5$ CFU/ml) in a 100 μl final volume. The plates are incubated for 18-22 hours at 35° C. in ambient air. The minimal inhibitory concentration for all isolates is defined as the lowest concentration of antimicrobial agent that completely inhibits the growth of the organism as detected by the unaided eye.

1. NCCLS. 2000. Methods for Dilution Antimicrobial Susceptibility Tests for Bacteria That Grow Aerobically; Approved Standards: M7-A5, vol. 20. National Committe for Clinical Laboratory Standards, Wayne, Pa.

Standard Pharmacological Test Procedures

Presented in Tables I-XIII are representative compounds of Formula I which were evaluated against a panel of 40 selected gram-positive and gram-negative bacteria strains by pre-incubation in water, mouse serum or human serum. Representative compounds were first incubated in mouse serum for an hour prior to the in vitro testing against a panel of selected gram-positive and gram-negative bacteria strains. All compounds were also pre-incubated in water for an hour prior to testing as control. Representative compounds of Formula I were incubated in human serum prior to MIC determination. Representative compounds of Formula I which demonstrated in vivo activity were further subjected to various stability tests. A summary of the in vitro testing data of representative examples of Formula I are shown in Table 1. Expanded in vitro data of selected examples (87 and 27) are shown in Table 2 and 5 respectively. MICs of representative examples of Formula I are further shown in Tables 3 and 4. Table 6 presents in vitro and in vivo activity of representative examples of compounds of Formula I against *Staph. aureus* Smith in mice. Table 7 presents in vivo (oral, iv) and in vitro (MIC) activity of representative examples of compounds of Formula I against *E. coli* in mice. Table 8 presents in vivo (oral, iv) and in vitro (MIC) activity of representative examples of compounds of Formula I, against *Staph aureus* Smith in mice. Table 9 presents in vitro (MIC) activity of representative examples of compounds of Formula I against *E. Coli* in human serum and water and also against *Staph* in human serum and water. Table 10 presents in vivo single oral dose (SOD) and single intravenous dose (SIV) $ED_{50}$ data for representative examples of compounds of Formula I against *Staph*. Smith and *E. Coli* #311 in mammals.

TABLE I

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 1 | Water Example 1 | Mouse Serum Example 2 | Water Example 2 | Mouse Serum Example 3 | Water Example 3 | Mouse Serum Example 4 | Water Example 4 |
|---|---|---|---|---|---|---|---|---|
| E. coli GC 2236 | 1 | 16 | 4 | 32 | 1 | >64 | 1 | 64 |
| E. coli GC 2231 | 1 | 64 | 4 | 64 | 2 | >64 | 1 | 64 |
| E. coli GC 2235 | 0.50 | 16 | 2 | 64 | 1 | >64 | 1 | 64 |

TABLE I-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 1 | Water Example 1 | Mouse Serum Example 2 | Water Example 2 | Mouse Serum Example 3 | Water Example 3 | Mouse Serum Example 4 | Water Example 4 |
|---|---|---|---|---|---|---|---|---|
| E. coli GC 2232 | 0.50 | 16 | 2 | 64 | 2 | >64 | 1 | 64 |
| E. coli GC 2233 | 1 | 16 | 1 | 64 | 1 | >64 | 1 | 64 |
| E. coli GC 2234 | 0.50 | 16 | 1 | 64 | 1 | >64 | 1 | 64 |
| E. coli GC 2270 | 0.50 | 16 | 1 | 64 | 1 | >64 | 1 | 64 |
| E. coli GC 2271 | 0.50 | 16 | 1 | 64 | 1 | >64 | 0.50 | 64 |
| E. coli GC 2272 | 1 | 16 | 1 | 64 | 1 | >64 | 1 | 64 |
| E. coli GC 4559 | 1 | 32 | 1 | 64 | 2 | >64 | 2 | >64 |
| E. coli GC 4560 | 0.50 | 2 | 0.25 | 4 | 0.50 | 32 | 0.25 | 8 |
| E. coli GC 6465 | 8 | >64 | 8 | 64 | 8 | >64 | 4 | >64 |
| E. coli GC 3226 | 1 | 32 | 4 | 64 | 2 | >64 | 2 | 64 |
| E. coli GC 2203 | 0.50 | 16 | 2 | 64 | 1 | >64 | 1 | 64 |
| E. coli GC 1073 | 1 | 32 | 4 | 64 | 2 | >64 | 1 | >64 |
| Salmonella spp. GC 235 | 1 | 64 | 8 | >64 | 2 | >64 | 2 | >64 |
| Salmonella spp. GC 566 | 2 | 64 | 8 | >64 | 4 | >64 | 4 | >64 |
| S. cholerasius GC 1355 | 8 | >64 | >64 | >64 | 16 | >64 | 8 | >64 |
| S. typhimurium GC 2172 | 4 | >64 | >64 | >64 | 8 | >64 | 4 | >64 |
| P. aeruginosa GC 2214 | 32 | >64 | >64 | >64 | 32 | >64 | 32 | >64 |
| S. aureus GC 1131 | 1 | 4 | 2 | 4 | 2 | 4 | 1 | 4 |
| S. aureus GC 6466 | 1 | 1 | 1 | 2 | 1 | 4 | 0.50 | 2 |
| S. aureus GC 6467 | 4 | 4 | 4 | 8 | 4 | 32 | 2 | 8 |
| S. aureus GC 1079 | 2 | 4 | 8 | 8 | 2 | 32 | 1 | 4 |
| S. aureus GC 4536 | 2 | 4 | 2 | 4 | 2 | 4 | 1 | 4 |
| S. aureus GC 2216 | 1 | 4 | 2 | 4 | 1 | 4 | 0.50 | 4 |
| S. aureus GC 6335 | 2 | 4 | 8 | 8 | 2 | 8 | 1 | 4 |
| S. aureus GC 6469 | 2 | 8 | 2 | 4 | 4 | 32 | 2 | 16 |
| S. epidermidis GC 4935 | 2 | 8 | 8 | 8 | 4 | 8 | 2 | 4 |
| E. faecalis GC 4555 | 1 | 4 | 2 | 4 | 1 | 8 | 1 | 8 |
| E. faecalis GC 2265 | 1 | 4 | 4 | 8 | 2 | 32 | 2 | 8 |
| E. faecalis GC 2267 | 2 | 8 | 4 | 4 | 2 | 32 | 1 | 8 |
| E. faecalis GC 2242 | 1 | 4 | 4 | 4 | 2 | 16 | 1 | 4 |
| E. faecium GC 4556 | 1 | 4 | 4 | 8 | 2 | 16 | 1 | 4 |
| E. faecium GC 2243 | 1 | 2 | 1 | 4 | 1 | 4 | 0.50 | 2 |
| S. pneumoniae* GC 4465 | 0.50 | 0.25 | 0.50 | 0.25 | 0.12 | 0.25 | <0.06 | 0.12 |
| S. pneumoniae+ GC 4465 | 2 | 2 | 2 | 4 | 1 | 2 | 2 | 4 |
| S. pyogenes GC 4563 | 0.25 | 0.50 | 0.25 | 0.25 | 0.12 | 0.25 | 0.12 | 0.25 |
| S. agalactiae GC 4564 | 0.50 | 1 | 2 | 2 | 1 | 2 | 0.25 | 0.50 |
| c. albicans GC 3066 | >64 | >64 | >64 | >64 | >64 | >64 | >64 | >64 |

TABLE II

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 5 | Water Example 5 | Mouse Serum Example 6 | Water Example 6 | Mouse Serum Example 7 | Water Example 7 | Mouse Serum Example 8 | Water Example 8 |
|---|---|---|---|---|---|---|---|---|
| E. coli GC 2236 | 2 | 16 | 2 | 8 | 0.25 | 2 | 1 | 32 |
| E. coli GC 2231 | 2 | 64 | 2 | 64 | 2 | 16 | 2 | >64 |
| E. coli GC 2235 | 1 | 16 | 1 | 8 | 0.50 | 4 | 1 | 16 |
| E. coli GC 2232 | 2 | 32 | 2 | 32 | 0.50 | 4 | 1 | 32 |
| E. coli GC 2233 | 2 | 32 | 2 | 16 | 0.50 | 4 | 1 | 32 |
| E. coli GC 2234 | 1 | 32 | 1 | 16 | 1 | 4 | 1 | 32 |
| E. coli GC 2270 | 1 | 16 | 1 | 8 | 0.50 | 4 | 1 | 64 |
| E. coli GC 2271 | 1 | 16 | 1 | 8 | 0.50 | 4 | 1 | 32 |
| E. coli GC 2272 | 1 | 32 | 1 | 16 | 0.50 | 4 | 1 | 32 |
| E. coli GC 4559 | 2 | 32 | 2 | 16 | 1 | 8 | 1 | 64 |
| E. coli GC 4560 | 0.50 | 4 | 0.25 | 2 | 0.25 | 0.50 | 0.50 | 4 |
| E. coli GC 6465 | 8 | >64 | 4 | >64 | 16 | >64 | 8 | >64 |
| E. coli GC 3226 | 2 | 32 | 2 | 16 | 0.50 | 8 | 2 | 64 |
| E. coli GC 2203 | 1 | 32 | 2 | 16 | 0.50 | 4 | 1 | 32 |
| E. coli GC 1073 | 2 | 32 | 2 | 16 | 0.50 | 8 | 1 | 32 |
| Salmonella spp. GC 235 | 2 | 32 | 2 | 16 | 2 | 8 | 4 | 64 |
| Salmonella spp. GC 566 | 4 | 64 | 4 | 64 | 1 | 16 | 4 | >64 |

TABLE II-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

| | Mouse Serum Example 5 | Water Example 5 | Mouse Serum Example 6 | Water Example 6 | Mouse Serum Example 7 | Water Example 7 | Mouse Serum Example 8 | Water Example 8 |
|---|---|---|---|---|---|---|---|---|
| S. cholerasius GC 1355 | 16 | >64 | 16 | >64 | 16 | >64 | 32 | >64 |
| S. typhimurium GC 2172 | 8 | >64 | 8 | >64 | 4 | >64 | 8 | >64 |
| P. aeruginosa GC 2214 | 32 | >64 | 32 | >64 | 16 | >64 | 32 | >64 |
| S. aureus GC 1131 | 0.50 | 1 | 0.50 | 1 | 1 | 1 | 1 | 2 |
| S. aureus GC 6466 | 0.25 | 0.50 | 0.25 | 1 | 0.50 | 0.50 | 0.50 | 1 |
| S. aureus GC 6467 | 2 | 4 | 2 | 4 | 4 | 4 | 4 | 8 |
| S. aureus GC 1079 | 2 | 2 | 2 | 4 | 1 | 4 | 2 | 4 |
| S. aureus GC 4536 | 1 | 1 | 0.50 | 2 | 1 | 1 | 0.50 | 2 |
| S. aureus GC 2216 | 0.50 | 2 | 0.50 | 2 | 0.50 | 0.50 | 0.50 | 4 |
| S. aureus GC 6335 | 0.50 | 1 | 0.50 | 2 | 1 | 1 | 1 | 4 |
| S. aureus GC 6469 | 2 | 4 | 2 | 4 | 2 | 4 | 2 | 8 |
| S. epidermidis GC 4935 | 1 | 2 | 1 | 4 | 2 | 2 | 2 | 8 |
| E. faecalis GC 4555 | 1 | 4 | 1 | 4 | 0.50 | 1 | 0.50 | 8 |
| E. faecalis GC 2265 | 2 | 4 | 2 | 4 | 1 | 2 | 2 | 8 |
| E. faecalis GC 2267 | 2 | 4 | 1 | 4 | 1 | 2 | 2 | 8 |
| E. faecalis GC 2242 | 1 | 2 | 1 | 2 | 1 | 1 | 1 | 4 |
| E. faecium GC 4556 | 1 | 2 | 1 | 2 | 0.50 | 1 | 1 | 4 |
| E. faecium GC 2243 | 0.50 | 1 | 0.50 | 2 | 0.25 | 0.12 | 0.25 | 2 |
| S. pneumoniae* GC 4465 | <0.06 | 0.12 | 0.12 | 0.25 | 0.25 | 0.12 | <0.06 | 0.25 |
| S. pneumoniae+ GC 4465 | 2 | 4 | 2 | 2 | 4 | 2 | 1 | 4 |
| S. pyogenes GC 4563 | 0.12 | 0.25 | 0.25 | 0.25 | 0.25 | 0.25 | 0.12 | 0.50 |
| S. agalactiae GC 4564 | 0.50 | 0.50 | 0.50 | 0.50 | 0.25 | 0.50 | 0.25 | 0.50 |
| c. albicans GC 3066 | >64 | >64 | >64 | >64 | >64 | >64 | >64 | >64 |

TABLE III

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

| | Mouse Serum Example 9 | Water Example 9 | Mouse Serum Example 10 | Water Example 10 | Mouse Serum Example 11 | Water Example 11 | Mouse Serum Example 12 | Water Example 12 |
|---|---|---|---|---|---|---|---|---|
| E. coli GC 2236 | 1 | 8 | 0.50 | 8 | 0.50 | 8 | 1 | 16 |
| E. coli GC 2231 | 2 | 64 | 2 | 32 | 2 | 64 | 2 | 64 |
| E. coli GC 2235 | 0.50 | 4 | 0.25 | 4 | 0.25 | 4 | 1 | 16 |
| E. coli GC 2232 | 1 | 8 | 0.50 | 8 | 1 | 16 | 0.50 | 32 |
| E. coli GC 2233 | 0.50 | 4 | 0.50 | 8 | 0.25 | 8 | 1 | 32 |
| E. coli GC 2234 | 0.50 | 8 | 0.50 | 8 | 0.50 | 16 | 1 | 16 |
| E. coli GC 2270 | 0.50 | 4 | 0.50 | 8 | 0.50 | 8 | 0.50 | 32 |
| E. coli GC 2271 | 0.50 | 8 | 0.25 | 8 | 0.25 | 4 | 0.50 | 16 |
| E. coli GC 2272 | 0.50 | 8 | 0.50 | 8 | 0.25 | 4 | 1 | 16 |
| E. coli GC 4559 | 1 | 8 | 0.50 | 16 | 0.50 | 32 | 1 | 64 |
| E. coli GC 4560 | 0.25 | 1 | 0.12 | 0.12 | 0.12 | 0.12 | 0.25 | 1 |
| E. coli GC 6465 | 4 | >64 | 8 | >64 | 8 | >64 | 8 | >64 |
| E. coli GC 3226 | 2 | 16 | 0.50 | 16 | 0.50 | >64 | 2 | 64 |
| E. coli GC 2203 | 0.50 | 4 | 0.50 | 8 | 0.25 | 16 | 1 | 32 |
| E. coli GC 1073 | 1 | 8 | 0.50 | 16 | 0.50 | 16 | 1 | 64 |
| Salmonella spp. GC 235 | 1 | 8 | 0.50 | 32 | 0.50 | 64 | 1 | 64 |
| Salmonella spp. GC 566 | 2 | 64 | 2 | >64 | 2 | >64 | 4 | >64 |
| S. cholerasius GC 1355 | 64 | >64 | 16 | >64 | 32 | >64 | 16 | >64 |
| S. typhimurium GC 2172 | 8 | >64 | 4 | >64 | 4 | >64 | 4 | >64 |
| P. aeruginosa GC 2214 | 16 | >64 | 16 | >64 | 16 | >64 | 32 | >64 |
| S. aureus GC 1131 | <0.06 | 0.25 | 0.12 | 0.12 | 0.25 | 0.25 | 1 | 2 |
| S. aureus GC 6466 | 0.12 | 0.12 | 0.12 | 0.12 | 0.25 | 0.25 | 0.50 | 1 |
| S. aureus GC 6467 | 1 | 2 | 2 | 2 | 4 | 4 | 4 | 16 |
| S. aureus GC 1079 | 2 | 1 | 0.50 | 1 | 2 | 4 | 2 | 8 |
| S. aureus GC 4536 | 0.50 | 0.50 | 0.25 | 0.50 | 0.50 | 0.50 | 1 | 2 |
| S. aureus GC 2216 | 0.25 | 0.50 | 0.25 | 0.50 | 0.50 | 0.50 | 1 | 4 |
| S. aureus GC 6335 | 0.25 | 0.50 | 0.25 | 0.50 | 1 | 1 | 1 | 2 |
| S. aureus GC 6469 | 1 | 2 | 1 | 2 | 4 | 4 | 4 | 16 |

TABLE III-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 9 | Water Example 9 | Mouse Serum Example 10 | Water Example 10 | Mouse Serum Example 11 | Water Example 11 | Mouse Serum Example 12 | Water Example 12 |
|---|---|---|---|---|---|---|---|---|
| S. epidermidis GC 4935 | 0.25 | 1 | 0.50 | 1 | 1 | 2 | 4 | 8 |
| E. faecalis GC 4555 | 0.50 | 2 | 0.50 | 1 | 0.50 | 1 | 0.50 | 4 |
| E. faecalis GC 2265 | 1 | 2 | 1 | 1 | 2 | 4 | 2 | 8 |
| E. faecalis GC 2267 | 1 | 2 | 1 | 2 | 2 | 2 | 2 | 8 |
| E. faecalis GC 2242 | 0.50 | 1 | 0.25 | 0.50 | 0.25 | 0.50 | 2 | 4 |
| E. faecium GC 4556 | 0.25 | 0.50 | 0.25 | 0.50 | 0.25 | 0.50 | 1 | 4 |
| E. faecium GC 2243 | 0.25 | 0.50 | <0.06 | 0.12 | 0.12 | 0.25 | 0.50 | 4 |
| S. pneumoniae* GC 4465 | <0.06 | <0.06 | <0.06 | <0.06 | <0.06 | <0.06 | <0.06 | 0.12 |
| S. pneumoniae+ GC 4465 | 2 | 2 | 1 | 1 | 2 | 2 | 4 | 8 |
| S. pyogenes GC 4563 | <0.06 | <0.06 | <0.06 | <0.06 | <0.06 | <0.06 | 0.12 | 0.25 |
| S. agalactiae GC 4564 | 0.12 | 0.25 | <0.06 | 0.12 | <0.06 | <0.06 | 0.25 | 0.25 |
| c. albicans GC 3066 | >64 | >64 | >64 | >64 | >64 | >64 | >64 | >64 |

TABLE IV

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 13 | Water Example 13 | Mouse Serum Example 14 | Water Example 14 | Mouse Serum Example 15 | Water Example 15 | Mouse Serum Example 16 | Water Example 16 |
|---|---|---|---|---|---|---|---|---|
| E. coli GC 2236 | 2 | 8 | >64 | >64 | >64 | 64 | 64 | >64 |
| E. coli GC 2231 | 2 | 16 | >64 | >64 | >64 | >64 | >64 | >64 |
| E. coli GC 2235 | 2 | 8 | 32 | 64 | 32 | 32 | 16 | 64 |
| E. coli GC 2232 | 2 | 8 | >64 | >64 | >64 | >64 | >64 | >64 |
| E. coli GC 2233 | 2 | 8 | >64 | >64 | >64 | >64 | >64 | >64 |
| E. coli GC 2234 | 1 | 8 | >64 | >64 | >64 | >64 | >64 | >64 |
| E. coli GC 2270 | 1 | 8 | >64 | >64 | 64 | 64 | >64 | >64 |
| E. coli GC 2271 | 2 | 8 | >64 | >64 | 64 | 64 | >64 | >64 |
| E. coli GC 2272 | 2 | 8 | >64 | >64 | >64 | >64 | >64 | >64 |
| E. coli GC 4559 | 4 | 16 | >64 | >64 | >64 | >64 | >64 | >64 |
| E. coli GC 4560 | 1 | 4 | 4 | 4 | 1 | 1 | 2 | 4 |
| E. coli GC 6465 | 8 | >64 | >64 | >64 | >64 | >64 | >64 | >64 |
| E. coli GC 3226 | 2 | 16 | >64 | >64 | >64 | >64 | 64 | >64 |
| E. coli GC 2203 | 2 | 8 | 32 | 64 | 32 | 64 | 16 | 64 |
| E. coli GC 1073 | 2 | 16 | >64 | >64 | >64 | >64 | >64 | >64 |
| Salmonella spp. GC 235 | 2 | 16 | >64 | >64 | >64 | >64 | >64 | >64 |
| Salmonella spp. GC 566 | 8 | 64 | >64 | >64 | >64 | >64 | >64 | >64 |
| S. cholerasius GC 1355 | 16 | >64 | >64 | >64 | >64 | >64 | >64 | >64 |
| S. typhimurium GC 2172 | 8 | 64 | >64 | >64 | >64 | >64 | >64 | >64 |
| P. aeruginosa GC 2214 | 32 | >64 | >64 | >64 | >64 | >64 | >64 | >64 |
| S. aureus GC 1131 | 2 | 2 | 1 | 2 | 2 | 4 | 2 | 4 |
| S. aureus GC 6466 | 1 | 2 | 2 | 8 | 2 | 4 | 4 | 8 |
| S. aureus GC 6467 | 4 | 8 | 2 | 4 | 16 | 16 | 8 | 8 |
| S. aureus GC 1079 | 4 | 4 | 1 | 2 | 2 | 4 | 2 | 4 |
| S. aureus GC 4536 | 1 | 2 | 2 | 2 | 2 | 4 | 2 | 4 |
| S. aureus GC 2216 | 2 | 4 | 2 | 4 | 2 | 4 | 2 | 4 |
| S. aureus GC 6335 | 2 | 4 | 1 | 4 | 4 | 4 | 4 | 4 |
| S. aureus GC 6469 | 4 | 8 | 2 | 4 | 4 | 8 | 4 | 8 |
| S. epidermidis GC 4935 | 4 | 8 | 8 | 8 | 16 | 16 | 8 | 8 |
| E. faecalis GC 4555 | 2 | 4 | 2 | 8 | 4 | 8 | 4 | 8 |
| E. faecalis GC 2265 | 4 | 8 | 2 | 8 | 8 | 8 | 4 | 8 |

TABLE IV-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 13 | Water Example 13 | Mouse Serum Example 14 | Water Example 14 | Mouse Serum Example 15 | Water Example 15 | Mouse Serum Example 16 | Water Example 16 |
|---|---|---|---|---|---|---|---|---|
| E. faecalis GC 2267 | 4 | 8 | 2 | 8 | 8 | 8 | 4 | 8 |
| E. faecalis GC 2242 | 4 | 8 | 2 | 8 | 8 | 8 | 8 | 8 |
| E. faecium GC 4556 | 2 | 8 | 4 | 8 | 8 | 8 | 4 | 8 |
| E. faecium GC 2243 | 2 | 4 | 2 | 4 | 8 | 8 | 4 | 8 |
| S. pneumoniae* GC 4465 | 0.50 | 0.50 | 2 | 4 | 2 | 2 | 4 | 4 |
| S. pneumoniae+ GC 4465 | 8 | 8 | 4 | 4 | 4 | 4 | 8 | 8 |
| S. pyogenes GC 4563 | 0.50 | 1 | 2 | 4 | 2 | 2 | 4 | 8 |
| S. agalactiae GC 4564 | 1 | 2 | 16 | 16 | 8 | 8 | 16 | 16 |
| c. albicans GC 3066 | >64 | >64 | >64 | >64 | >64 | >64 | >64 | >64 |

TABLE V

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 21 | Water Example 21 | Mouse Serum Example 22 | Water Example 22 | Mouse Serum Example 23 | Water Example 23 | Mouse Serum Example 24 | Water Example 24 |
|---|---|---|---|---|---|---|---|---|
| E. coli GC 2236 | 1 | >64 | 2 | >64 | 2 | >64 | 1 | >64 |
| E. coli GC 2231 | 1 | >64 | 2 | >64 | 2 | >64 | 2 | >64 |
| E. coli GC 2235 | 0.50 | >64 | 1 | >64 | 1 | >64 | 0.50 | >64 |
| E. coli GC 2232 | 1 | >64 | 2 | >64 | 1 | >64 | 0.50 | >64 |
| E. coli GC 2233 | 1 | >64 | 2 | >64 | 2 | >64 | 1 | >64 |
| E. coli GC 2234 | 0.50 | >64 | 1 | >64 | 1 | >64 | 0.50 | >64 |
| E. coli GC 2270 | 1 | >64 | 1 | >64 | 1 | >64 | 0.50 | >64 |
| E. coli GC 2271 | 0.50 | >64 | 1 | >64 | 1 | >64 | 0.50 | >64 |
| E. coli GC 2272 | 1 | >64 | 1 | >64 | 1 | >64 | 1 | >64 |
| E. coli GC 4559 | 1 | >64 | 2 | >64 | 2 | >64 | 1 | >64 |
| E. coli GC 4560 | 0.25 | >64 | 0.50 | >64 | 0.50 | 8 | 0.25 | 64 |
| E. coli GC 6465 | 4 | >64 | 8 | >64 | 4 | >64 | 8 | >64 |
| E. coli GC 3226 | 8 | >64 | 8 | >64 | 8 | >64 | 1 | >64 |
| E. coli GC 2203 | 0.50 | >64 | 1 | >64 | 1 | >64 | 0.50 | >64 |
| E. coli GC 1073 | 1 | >64 | 2 | >64 | 1 | >64 | 1 | >64 |
| Salmonella spp. GC 235 | 2 | >64 | 2 | >64 | 2 | >64 | 1 | >64 |
| Salmonella spp. GC 566 | 4 | >64 | 4 | >64 | 4 | >64 | 2 | >64 |
| S. cholerasius GC 1355 | 16 | >64 | 16 | >64 | 16 | >64 | 32 | >64 |
| S. typhimurium GC 2172 | 4 | >64 | 8 | >64 | 4 | >64 | 8 | >64 |
| P. aeruginosa GC 2214 | >64 | >64 | >64 | >64 | >64 | >64 | 16 | >64 |
| S. aureus GC 1131 | 1 | 64 | 1 | 4 | 1 | 2 | 1 | 2 |
| S. aureus GC 6466 | 1 | 64 | 0.50 | 2 | 0.25 | 0.50 | 0.25 | 0.50 |
| S. aureus GC 6467 | 4 | >64 | 4 | >64 | 4 | 8 | 4 | >64 |
| S. aureus GC 1079 | 4 | >64 | 2 | 32 | 2 | 4 | 2 | 64 |
| S. aureus GC 4536 | 2 | 32 | 1 | 2 | 1 | 2 | 1 | 4 |
| S. aureus GC 2216 | 1 | 64 | 1 | 4 | 1 | 4 | 0.50 | 4 |
| S. aureus GC 6335 | 2 | 64 | 2 | 8 | 2 | 4 | 2 | 16 |
| S. aureus GC 6469 | 4 | >64 | 4 | 64 | 4 | 4 | 4 | >64 |
| S. epidermidis GC 4935 | 2 | 64 | 2 | 16 | 2 | 4 | 2 | 16 |
| E. faecalis GC 4555 | 1 | 64 | 2 | 64 | 1 | 4 | 1 | 64 |
| E. faecalis GC 2265 | 1 | 64 | 2 | 64 | 1 | 4 | 2 | 32 |
| E. faecalis GC 2267 | 2 | 64 | 4 | 64 | 2 | 8 | 4 | 64 |
| E. faecalis GC 2242 | 2 | 32 | 2 | 32 | 2 | 4 | 2 | 4 |
| E. faecium GC 4556 | 2 | 64 | 2 | 64 | 2 | 4 | 1 | 32 |
| E. faecium GC 2243 | 0.50 | 8 | 1 | 8 | 0.50 | 4 | 0.50 | 2 |
| S. pneumoniae* GC 4465 | 0.25 | 0.50 | 0.50 | 1 | 0.12 | 0.12 | <0.06 | <0.06 |
| S. pneumoniae+ GC 4465 | 4 | 4 | 4 | 16 | 4 | 8 | 2 | 1 |
| S. pyogenes GC 4563 | 0.25 | 0.12 | 0.50 | 1 | 0.12 | 0.25 | <0.06 | <0.06 |
| S. agalactiae GC 4564 | 0.50 | 8 | 1 | 8 | 0.25 | 0.25 | 0.50 | 8 |
| c. albicans GC 3066 | >64 | >64 | >64 | >64 | >64 | >64 | >64 | >64 |

TABLE VI

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Mouse Serum Example 25 | Water Example 25 | Mouse Serum Example 26 | Water Example 26 | Mouse Serum Example 27 | Water Example 27 | Mouse Serum Example 28 | Water Example 28 |
|---|---|---|---|---|---|---|---|---|
| E. coli GC 2236 | 2 | 64 | 2 | >64 | 0.50 | 64 | 0.50 | >64 |
| E. coli GC 2231 | 2 | >64 | 4 | >64 | 1 | >64 | 1 | >64 |
| E. coli GC 2235 | 1 | 32 | 1 | 64 | 0.50 | 64 | 0.50 | >64 |
| E. coli GC 2232 | 1 | >64 | 1 | >64 | 0.50 | 64 | 0.50 | >64 |
| E. coli GC 2233 | 2 | 32 | 2 | >64 | 0.50 | 64 | 0.50 | >64 |
| E. coli GC 2234 | 1 | >64 | 1 | >64 | 0.50 | 64 | 0.25 | >64 |
| E. coli GC 2270 | 1 | >64 | 1 | >64 | 0.50 | 64 | 0.50 | >64 |
| E. coli GC 2271 | 1 | 32 | 1 | >64 | 0.50 | 64 | 0.25 | >64 |
| E. coli GC 2272 | 2 | 64 | 2 | 64 | 0.50 | 32 | 0.50 | >64 |
| E. coli GC 4559 | 2 | >64 | 2 | >64 | 0.50 | >64 | 0.50 | >64 |
| E. coli GC 4560 | 0.50 | 2 | 0.50 | 8 | 0.25 | 1 | 0.25 | >64 |
| E. coli GC 6465 | 8 | >64 | 8 | >64 | 4 | >64 | 8 | >64 |
| E. coli GC 3226 | 2 | >64 | 2 | >64 | 0.50 | >64 | 0.50 | >64 |
| E. coli GC 2203 | 1 | >64 | 1 | >64 | 0.50 | >64 | 0.50 | >64 |
| E. coli GC 1073 | 2 | >64 | 2 | >64 | 0.50 | >64 | 0.50 | >64 |
| Salmonella spp. GC 235 | 2 | >64 | 2 | >64 | 1 | >64 | 0.50 | >64 |
| Salmonella spp. GC 566 | 4 | >64 | 4 | >64 | 1 | >64 | 2 | >64 |
| S. cholerasius GC 1355 | 32 | >64 | 32 | >64 | 16 | >64 | 16 | >64 |
| S. typhimurium GC 2172 | 8 | >64 | 16 | >64 | 4 | >64 | 8 | >64 |
| P. aeruginosa GC 2214 | 32 | >64 | 32 | >64 | 8 | >64 | 16 | >64 |
| S. aureus GC 1131 | 0.50 | 0.50 | 0.50 | 0.50 | 0.12 | 0.25 | 0.50 | 32 |
| S. aureus GC 6466 | 0.25 | 0.25 | 0.25 | 0.25 | 0.12 | 0.25 | 0.50 | 4 |
| S. aureus GC 6467 | 2 | 2 | 1 | 4 | 2 | 2 | 4 | 64 |
| S. aureus GC 1079 | 1 | 2 | 1 | 2 | 1 | 2 | 2 | 64 |
| S. aureus GC 4536 | 0.50 | 0.50 | 0.25 | 0.50 | 0.12 | 0.12 | 0.50 | 32 |
| S. aureus GC 2216 | 0.50 | 1 | 0.50 | 0.50 | 0.25 | 0.25 | 0.50 | 32 |
| S. aureus GC 6335 | 0.50 | 0.50 | 0.50 | 1 | 0.25 | 0.50 | 1 | 16 |
| S. aureus GC 6469 | 2 | 4 | 1 | 2 | 1 | 2 | 4 | 64 |
| S. epidermidis GC 4935 | 1 | 2 | 1 | 2 | 0.25 | 1 | 1 | 32 |
| E. faecalis GC 4555 | 1 | 2 | 1 | 4 | 0.25 | 1 | 0.25 | 64 |
| E. faecalis GC 2265 | 2 | 2 | 2 | 8 | 1 | 2 | 2 | 64 |
| E. faecalis GC 2267 | 2 | 4 | 2 | 4 | 1 | 2 | 2 | 64 |
| E. faecalis GC 2242 | 2 | 2 | 2 | 4 | 0.50 | 0.50 | 0.50 | 4 |
| E. faecium GC 4556 | 1 | 4 | 1 | 4 | 0.50 | 1 | 0.50 | 32 |
| E. faecium GC 2243 | 0.50 | 1 | 1 | 2 | 0.12 | 0.25 | 0.25 | 0.25 |
| S. pneumoniae* GC 4465 | 0.12 | 0.25 | 0.25 | 0.25 | <0.06 | <0.06 | <0.06 | <0.06 |
| S. pneumoniae+ GC 4465 | 4 | 4 | 4 | 4 | 1 | 2 | 2 | 0.50 |
| S. pyogenes GC 4563 | 0.12 | 0.25 | 0.25 | 0.25 | <0.06 | <0.06 | <0.06 | <0.06 |
| S. agalactiae GC 4564 | 0.50 | 0.50 | 1 | 2 | 0.12 | 0.12 | 0.25 | 0.50 |
| c. albicans GC 3066 | >64 | >64 | >64 | >64 | >64 | >64 | >64 | >64 |

TABLE VII

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

|  | Water Example 42 | Mouse Serum Example 42 | Mouse Serum Example 42 | Water Example 43 | Mouse Serum Example 43 | Human Serum Example 43 | Water Example 44 | Mouse Serum Example 44 | Human Serum Example 44 |
|---|---|---|---|---|---|---|---|---|---|
| E. coli GC 2236 | >64 | 4 | >64 | >64 | 0.50 | >64 | >64 | 2 | >64 |
| E. coli GC 2231 | >64 | 4 | >64 | >64 | 0.50 | >64 | >64 | 2 | >64 |
| E. coli GC 2235 | >64 | 4 | >64 | >64 | 0.25 | >64 | >64 | 2 | >64 |
| E. coli GC 2232 | >64 | 4 | >64 | >64 | 0.50 | >64 | >64 | 2 | >64 |
| E. coli GC 2233 | >64 | 4 | >64 | >64 | 0.50 | >64 | >64 | 2 | >64 |
| E. coli GC 2234 | >64 | 4 | >64 | >64 | 0.25 | >64 | >64 | 2 | >64 |
| E. coli GC 2270 | >64 | 4 | >64 | >64 | 0.25 | >64 | >64 | 2 | >64 |
| E. coli GC 2271 | >64 | 4 | >64 | >64 | 0.25 | >64 | >64 | 2 | >64 |
| E. coli GC 2272 | >64 | 4 | >64 | >64 | 0.50 | >64 | >64 | 2 | >64 |
| E. coli GC 4559 | >64 | 8 | >64 | >64 | 0.50 | >64 | >64 | 4 | >64 |
| E. coli GC 4560 | 8 | 2 | 8 | 32 | <0.06 | 16 | 4 | 2 | 4 |
| E. coli GC 6465 | >64 | 16 | >64 | >64 | 2 | >64 | >64 | 8 | >64 |
| E. coli GC 3226 | >64 | 16 | >64 | >64 | 1 | >64 | >64 | 4 | >64 |
| E. coli GC 2203 | >64 | 8 | >64 | >64 | 0.50 | >64 | >64 | 2 | >64 |

TABLE VII-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

| | Water Example 42 | Mouse Serum Example 42 | Mouse Serum Example 42 | Water Example 43 | Mouse Serum Example 43 | Human Serum Example 43 | Water Example 44 | Mouse Serum Example 44 | Human Serum Example 44 |
|---|---|---|---|---|---|---|---|---|---|
| E. coli GC 1073 | >64 | 8 | >64 | >64 | 0.50 | >64 | >64 | 4 | >64 |
| Salmonella spp. GC 235 | >64 | 16 | >64 | >64 | 0.50 | >64 | >64 | 4 | >64 |
| Salmonella spp. GC 566 | >64 | 32 | >64 | >64 | 2 | >64 | >64 | 8 | >64 |
| S. cholerasius GC 1355 | >64 | 64 | >64 | >64 | 4 | >64 | >64 | 16 | >64 |
| S. typhimurium GC 2172 | >64 | 64 | >64 | >64 | 2 | >64 | >64 | 8 | >64 |
| P. aeruginosa GC 2214 | >64 | >64 | >64 | >64 | 16 | >64 | >64 | >64 | >64 |
| S. aureus GC 1131 | 4 | 2 | 2 | 64 | 1 | 16 | 4 | 2 | 2 |
| S. aureus GC 6466 | 4 | 2 | 4 | 64 | 0.50 | 16 | 2 | 2 | 2 |
| S. aureus GC 6467 | 8 | 4 | 4 | >64 | 0.50 | 32 | 4 | 2 | 2 |
| S. aureus GC 1079 | 4 | 2 | 4 | 64 | 1 | 32 | 4 | 2 | 2 |
| S. aureus GC 4536 | 8 | 2 | 4 | 32 | 1 | 16 | 4 | 2 | 2 |
| S. aureus GC 2216 | 4 | 2 | 2 | 64 | 0.50 | 32 | 2 | 2 | 2 |
| S. aureus GC 6335 | 4 | 2 | 4 | 64 | 1 | 64 | 4 | 2 | 4 |
| S. aureus GC 6469 | 4 | 2 | 4 | >64 | 1 | 32 | 4 | 2 | 2 |
| S. epidermidis GC 4935 | 8 | 4 | 4 | 32 | 2 | 4 | 4 | 2 | 4 |
| E. faecalis GC 4555 | 4 | 2 | 4 | 32 | 0.50 | 8 | 4 | 2 | 4 |
| E. faecalis GC 2265 | 8 | 2 | 4 | 32 | 0.50 | 8 | 4 | 2 | 2 |
| E. faecalis GC 2267 | 4 | 2 | 4 | 32 | 0.50 | 4 | 4 | 2 | 4 |
| E. faecalis GC 2242 | 8 | 4 | 4 | 16 | 0.50 | 4 | 4 | 2 | 4 |
| E. faecium GC 4556 | 8 | 2 | 4 | 16 | 0.50 | 8 | 4 | 2 | 4 |
| E. faecium GC 2243 | 4 | 2 | 4 | 0.25 | 0.12 | 0.25 | 4 | 2 | 4 |
| S. pneumoniae* GC 4465 | 4 | 2 | 4 | 0.50 | <0.06 | 1 | 2 | 1 | 2 |
| S. pneumoniae+ GC 4465 | 8 | 4 | 8 | 2 | 2 | 2 | 4 | 4 | 4 |
| S. pyogenes GC 4563 | 4 | 2 | 4 | <0.06 | <0.06 | <0.06 | 2 | 1 | 4 |
| S. agalactiae GC 4564 | 8 | 2 | 8 | 2 | <0.06 | 2 | 4 | 1 | 4 |
| c. albicans GC 3066 | >64 | >64 | >64 | >64 | >64 | >64 | >64 | >64 | >64 |

TABLE VIII

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

| | Water Example 45 | Mouse Serum Example 45 | Human Serum Example 45 | Water Example 46 | Mouse Serum Example 46 | Human Serum Example 46 | Water Example 47 | Mouse Serum Example 47 | Human Serum Example 47 |
|---|---|---|---|---|---|---|---|---|---|
| E. coli GC 2236 | 16 | 1 | 4 | 64 | 0.50 | 4 | >64 | 1 | 32 |
| E. coli GC 2231 | 32 | 1 | 4 | 64 | 0.50 | 4 | >64 | 1 | 32 |
| E. coli GC 2235 | 16 | 0.50 | 4 | 64 | 0.50 | 4 | >64 | 1 | 16 |
| E. coli GC 2232 | 16 | 1 | 4 | 64 | 0.50 | 4 | >64 | 1 | 16 |
| E. coli GC 2233 | 16 | 1 | 4 | 64 | 0.50 | 4 | >64 | 0.50 | 16 |
| E. coli GC 2234 | 16 | 0.50 | 4 | 64 | 0.50 | 4 | >64 | 1 | 16 |
| E. coli GC 2270 | 32 | 0.50 | 4 | >64 | 0.50 | 4 | >64 | 0.50 | 16 |
| E. coli GC 2271 | 16 | 0.50 | 4 | 64 | 0.50 | 4 | >64 | 1 | 16 |
| E. coli GC 2272 | 16 | 1 | 8 | 64 | 1 | 4 | >64 | 1 | 16 |
| E. coli GC 4559 | 64 | 1 | 8 | >64 | 1 | 8 | >64 | 2 | 64 |
| E. coli GC 4560 | 2 | 0.25 | 0.50 | 4 | 0.50 | 1 | 16 | 1 | 4 |
| E. coli GC 6465 | >64 | 2 | 16 | >64 | 2 | 16 | >64 | 2 | >64 |
| E. coli GC 3226 | 64 | 1 | 8 | >64 | 1 | 16 | >64 | 2 | 32 |
| E. coli GC 2203 | 32 | 0.50 | 4 | >64 | 0.50 | 8 | >64 | 1 | 32 |
| E. coli GC 1073 | 64 | 1 | 8 | >64 | 1 | 8 | >64 | 2 | 32 |
| Salmonella spp. GC 235 | >64 | 1 | 8 | >64 | 1 | 16 | >64 | 2 | 64 |
| Salmonella spp. GC 566 | >64 | 2 | 32 | >64 | 2 | 16 | >64 | 4 | >64 |
| S. cholerasius GC 1355 | >64 | 4 | 32 | >64 | 2 | 32 | >64 | 4 | >64 |
| S. typhimurium GC 2172 | >64 | 2 | 32 | >64 | 2 | 32 | >64 | 4 | >64 |
| P. aeruginosa GC 2214 | >64 | 16 | >64 | >64 | 16 | >64 | >64 | 32 | >64 |
| S. aureus GC 1131 | 1 | 0.50 | 0.50 | 0.50 | 0.50 | 0.50 | 2 | 1 | 2 |
| S. aureus GC 6466 | 0.50 | 0.25 | 0.25 | 0.25 | 0.25 | 0.25 | 2 | 1 | 1 |
| S. aureus GC 6467 | 2 | 1 | 1 | 1 | 1 | 0.50 | 4 | 1 | 2 |
| S. aureus GC 1079 | 1 | 0.50 | 0.12 | 0.50 | 0.50 | 0.50 | 2 | 1 | 2 |
| S. aureus GC 4536 | 1 | 0.50 | 0.50 | 0.50 | 0.50 | 0.50 | 4 | 1 | 1 |
| S. aureus GC 2216 | 1 | 1 | 0.50 | 1 | 0.50 | 0.50 | 2 | 1 | 1 |
| S. aureus GC 6335 | 2 | 1 | 0.50 | 1 | 1 | 0.50 | 2 | 1 | 2 |
| S. aureus GC 6469 | 1 | 1 | 0.50 | 1 | 1 | 0.50 | 4 | 1 | 2 |
| S. epidermidis GC 4935 | 2 | 1 | 1 | 2 | 1 | 1 | 4 | 2 | 4 |

TABLE VIII-continued

ANTIBACTERIAL ACTIVITY OF 9-AMINOCARBONYLSUBSTITUTED DERIVATIVES
OF GLYCYLCYCLINES OF FORMULA I
MINIMAL INHIBITORY CONCENTRATION MIC(UG/ML)

| | Water Example 45 | Mouse Serum Example 45 | Human Serum Example 45 | Water Example 46 | Mouse Serum Example 46 | Human Serum Example 46 | Water Example 47 | Mouse Serum Example 47 | Human Serum Example 47 |
|---|---|---|---|---|---|---|---|---|---|
| E. faecalis GC 4555 | 2 | 1 | 2 | 2 | 0.50 | 0.50 | 4 | 1 | 4 |
| E. faecalis GC 2265 | 4 | 0.50 | 1 | 2 | 0.50 | 1 | 4 | 1 | 4 |
| E. faecalis GC 2267 | 2 | 0.50 | 1 | 2 | 0.50 | 1 | 4 | 1 | 4 |
| E. faecalis GC 2242 | 2 | 1 | 1 | 1 | 0.50 | 1 | 4 | 1 | 4 |
| E. faecium GC 4556 | 2 | 1 | 1 | 1 | 0.50 | 1 | 4 | 1 | 4 |
| E. faecium GC 2243 | 2 | 0.50 | 1 | 0.50 | 0.25 | 0.25 | 2 | 0.50 | 2 |
| S. pneumoniae* GC 4465 | 0.50 | 0.25 | 0.25 | 0.12 | 0.12 | 0.12 | 0.50 | 0.25 | 0.50 |
| S. pneumoniae+ GC 4465 | 4 | 2 | 2 | 1 | 1 | 1 | 4 | 2 | 2 |
| S. pyogenes GC 4563 | 0.50 | 0.25 | 0.25 | 0.25 | 0.12 | 0.25 | 0.25 | 0.12 | 0.25 |
| S. agalactiae GC 4564 | 0.50 | 0.25 | 0.50 | 0.25 | 0.25 | 0.25 | 1 | 0.50 | 1 |
| c. albicans GC 3066 | >64 | >64 | >64 | >64 | >64 | >64 | >64 | >64 | >64 |

TABLE IX

ANTIBACTERIAL ACTIVITY OF 9-AMINOCARBONYLSUBSTITUTED DERIVATIVES OF
GLYCYLCYCLINES OF FORMULA I MINIMAL INHIBITORY CONCENTRATION MIC (UG/ML)

| | Water Example 48 | Mouse Serum Example 48 | Human Serum Example 48 | Water Example 49 | Mouse Serum Example 49 | Human Serum Example 49 | Water Example 50 | Mouse Serum Example 50 | Human Serum Example 50 |
|---|---|---|---|---|---|---|---|---|---|
| E. coli GC 2236 | 64 | 0.25 | 16 | 16 | 0.50 | 4 | 32 | 1 | 8 |
| E. coli GC 2231 | 64 | 0.50 | 16 | 16 | 0.50 | 8 | 64 | 1 | 8 |
| E. coli GC 2235 | 32 | 0.25 | 16 | 8 | 0.50 | 4 | 32 | 1 | 4 |
| E. coli GC 2232 | 64 | 0.25 | 16 | 16 | 0.50 | 4 | 32 | 1 | 8 |
| E. coli GC 2233 | 64 | 0.25 | 16 | 8 | 0.25 | 4 | 32 | 1 | 8 |
| E. coli GC 2234 | 64 | 0.50 | 16 | 16 | 0.25 | 4 | 64 | 1 | 8 |
| E. coli GC 2270 | 64 | 0.50 | 16 | 16 | 0.50 | 4 | 32 | 1 | 8 |
| E. coli GC 2271 | 32 | 0.25 | 8 | 8 | 0.25 | 4 | 32 | 1 | 4 |
| E. coli GC 2272 | 64 | 0.25 | 8 | 8 | 0.50 | 2 | 32 | 1 | 4 |
| E. coli GC 4559 | >64 | 0.25 | 32 | 16 | 0.50 | 8 | 64 | 2 | 16 |
| E. coli GC 4560 | 2 | 0.12 | 1 | 1 | 0.12 | 0.50 | 4 | 0.50 | 2 |
| E. coli GC 6465 | >64 | 2 | >64 | >64 | 2 | 32 | >64 | 2 | 16 |
| E. coli GC 3226 | >64 | 0.50 | 32 | 16 | 0.50 | 8 | 32 | 1 | 8 |
| E. coli GC 2203 | 64 | 0.25 | 16 | 8 | 0.25 | 4 | 32 | 1 | 8 |
| E. coli GC 1073 | 64 | 0.50 | 32 | 32 | 0.50 | 8 | 32 | 2 | 8 |
| Salmonella spp. GC 235 | >64 | 0.50 | 32 | 32 | 1 | 16 | >64 | 2 | 32 |
| Salmonella spp. GC 566 | >64 | 2 | >64 | 64 | 2 | 32 | >64 | 4 | 32 |
| S. cholerasius GC 1355 | >64 | 4 | >64 | >64 | 4 | 64 | >64 | 4 | 64 |
| S. typhimurium GC 2172 | >64 | 4 | >64 | >64 | 4 | 32 | >64 | 4 | 32 |
| P. aeruginosa GC 2214 | >64 | 16 | >64 | >64 | 32 | >64 | >64 | 32 | >64 |
| S. aureus GC 1131 | 0.25 | 0.25 | 0.25 | 0.50 | 0.50 | 0.50 | 1 | 0.50 | 0.50 |
| S. aureus GC 6466 | 0.12 | 0.12 | 0.12 | 0.12 | 0.12 | 0.12 | 0.25 | 0.25 | 0.25 |
| S. aureus GC 6467 | 2 | 1 | 0.50 | 2 | 1 | 1 | 2 | 0.25 | 0.25 |
| S. aureus GC 1079 | 1 | 0.25 | 0.25 | 0.50 | 0.50 | 0.50 | 2 | 0.50 | 0.50 |
| S. aureus GC 4536 | 0.25 | 0.25 | 0.25 | 0.25 | 0.25 | 0.25 | 0.50 | 0.25 | 0.25 |
| S. aureus GC 2216 | 0.50 | 0.25 | 0.25 | 0.50 | 0.25 | 0.25 | 2 | 1 | 0.50 |
| S. aureus GC 6335 | 2 | 2 | 2 | 2 | 1 | 1 | 1 | 1 | 1 |
| S. aureus GC 6469 | 1 | 0.50 | 1 | 1 | 1 | 1 | 2 | 1 | 1 |
| S. epidermidis GC 4935 | 1 | 0.50 | 0.50 | 2 | 1 | 1 | 4 | 2 | 2 |
| E. faecalis GC 4555 | 2 | 0.12 | 4 | 4 | 0.25 | 0.50 | 4 | 1 | 2 |
| E. faecalis GC 2265 | 2 | 0.50 | 1 | 2 | 0.50 | 1 | 4 | 1 | 2 |
| E. faecalis GC 2267 | 2 | 0.50 | 1 | 4 | 0.50 | 1 | 4 | 1 | 2 |
| E. faecalis GC 2242 | 1 | 0.50 | 1 | 2 | 0.50 | 1 | 2 | 1 | 1 |
| E. faecium GC 4556 | 1 | 0.50 | 1 | 2 | 0.50 | 1 | 2 | 1 | 1 |
| E. faecium GC 2243 | 0.50 | 0.25 | 0.25 | 0.50 | 0.25 | 0.25 | 0.50 | 0.25 | 0.25 |
| S. pneumoniae* GC 4465 | 0.12 | 0.12 | 0.12 | 0.12 | 0.12 | 0.12 | <0.06 | <0.06 | <0.06 |
| S. pneumoniae+ GC 4465 | 0.25 | 0.25 | 0.25 | 1 | 1 | 1 | 0.50 | 0.50 | 0.50 |
| S. pyogenes GC 4563 | 0.12 | 0.12 | 0.12 | 0.12 | 0.12 | 0.12 | 0.25 | 0.12 | 0.12 |
| S. agalactiae GC 4564 | 0.12 | 0.12 | 0.12 | 0.25 | 0.12 | 0.12 | 0.25 | 0.25 | 0.25 |
| c. albicans GC 3066 | >64 | >64 | >64 | >64 | >64 | >64 | >64 | >64 | >64 |

TABLE X

ANTIBACTERIAL ACTIVITY OF 9-AMINOCARBONYLSUBSTITUTED DERIVATIVES OF
GLYCYLCYCLINES OF FORMULA I MINIMAL INHIBITORY CONCENTRATION MIC (UG/ML)

| | Water Example 51 | Mouse Serum Example 51 | Human Serum Example 51 | Water Example 52 | Mouse Serum Example 52 | Human Serum Example 52 | Water Example 53 | Mouse Serum Example 53 | Human Serum Example 53 |
|---|---|---|---|---|---|---|---|---|---|
| E. coli GC 2236 | >64 | 2 | 32 | 8 | 1 | 8 | 32 | 1 | 16 |
| E. coli GC 2231 | >64 | 2 | 32 | 16 | 1 | 8 | 64 | 1 | 16 |
| E. coli GC 2235 | >64 | 1 | 32 | 4 | 0.50 | 4 | 32 | 0.50 | 8 |
| E. coli GC 2232 | >64 | 2 | 32 | 8 | 0.50 | 4 | 32 | 0.50 | 8 |
| E. coli GC 2233 | >64 | 2 | 32 | 8 | 0.50 | 8 | 32 | 1 | 16 |
| E. coli GC 2234 | >64 | 1 | 32 | 8 | 0.50 | 4 | 16 | 0.50 | 8 |
| E. coli GC 2270 | >64 | 1 | 32 | 4 | 0.50 | 4 | 32 | 1 | 8 |
| E. coli GC 2271 | >64 | 1 | 32 | 4 | 0.50 | 4 | 16 | 0.50 | 8 |
| E. coli GC 2272 | >64 | 2 | 32 | 4 | 0.50 | 4 | 16 | 0.25 | 8 |
| E. coli GC 4559 | >64 | 2 | 32 | 8 | 1 | 8 | 32 | 1 | 16 |
| E. coli GC 4560 | 32 | 1 | 8 | 2 | 0.25 | 2 | 2 | 0.50 | 2 |
| E. coli GC 6465 | >64 | 4 | 32 | 64 | 2 | 16 | >64 | 4 | 32 |
| E. coli GC 3226 | >64 | 2 | 64 | 16 | 1 | 16 | 32 | 1 | 16 |
| E. coli GC 2203 | >64 | 2 | 32 | 8 | 0.50 | 8 | 32 | 1 | 16 |
| E. coli GC 1073 | >64 | 2 | 64 | 4 | 1 | 8 | 32 | 1 | 16 |
| Salmonella spp. GC 235 | >64 | 2 | 64 | 16 | 1 | 16 | 64 | 2 | 64 |
| Salmonella spp. GC 566 | >64 | 4 | 64 | 64 | 2 | 32 | >64 | 2 | 32 |
| S. cholerasius GC 1355 | >64 | 8 | >64 | >64 | 4 | >64 | >64 | 8 | 64 |
| S. typhimurium GC 2172 | >64 | 8 | 64 | 64 | 4 | 64 | >64 | 4 | 64 |
| P. aeruginosa GC 2214 | >64 | 64 | >64 | >64 | 64 | >64 | >64 | 64 | >64 |
| S. aureus GC 1131 | 1 | 0.50 | 0.50 | 2 | 0.50 | 1 | 1 | 1 | 1 |
| S. aureus GC 6466 | 1 | 0.25 | 0.25 | 2 | 0.50 | 1 | 0.50 | 0.50 | 0.50 |
| S. aureus GC 6467 | 2 | 0.50 | 1 | 4 | 0.50 | 4 | 2 | 1 | 1 |
| S. aureus GC 1079 | 2 | 0.50 | 1 | 2 | 0.50 | 1 | 1 | 0.50 | 0.50 |
| S. aureus GC 4536 | 1 | 0.50 | 0.50 | 2 | 0.50 | 0.50 | 1 | 0.25 | 0.50 |
| S. aureus GC 2216 | 1 | 0.50 | 0.50 | 4 | 0.50 | 1 | 1 | 0.50 | 0.50 |
| S. aureus GC 6335 | 1 | 0.50 | 0.50 | 4 | 1 | 2 | 1 | 0.50 | 0.50 |
| S. aureus GC 6469 | 2 | 1 | 1 | 4 | 0.50 | 2 | 2 | 1 | 1 |
| S. epidermidis GC 4935 | 4 | 2 | 2 | 4 | 1 | 4 | 2 | 1 | 2 |
| E. faecalis GC 4555 | 16 | 1 | 8 | 4 | 0.50 | 2 | 2 | 0.50 | 2 |
| E. faecalis GC 2265 | 8 | 1 | 4 | 4 | 1 | 4 | 4 | 1 | 0.50 |
| E. faecalis GC 2267 | 16 | 2 | 4 | 4 | 0.50 | 4 | 4 | 0.50 | 2 |
| E. faecalis GC 2242 | 8 | 2 | 4 | 4 | 0.50 | 4 | 2 | 0.50 | 2 |
| E. faecium GC 4556 | 8 | 2 | 8 | 4 | 0.50 | 2 | 2 | 0.50 | 2 |
| E. faecium GC 2243 | 4 | 1 | 4 | 1 | 0.25 | 1 | 0.50 | 0.25 | 0.25 |
| S. pneumoniae* GC 4465 | 1 | 0.50 | 2 | 0.12 | <0.06 | 0.25 | 0.12 | 0.12 | 0.25 |
| S. pneumoniae+ GC 4465 | 1 | 1 | 2 | 2 | 1 | 4 | 2 | 2 | 1 |
| S. pyogenes GC 4563 | 2 | 0.50 | 2 | 0.25 | 0.12 | 0.25 | 0.25 | 0.12 | 0.25 |
| S. agalactiae GC 4564 | 2 | 1 | 4 | 0.50 | 0.12 | 0.50 | 0.50 | <0.06 | 0.50 |
| c. albicans GC 3066 | >64 | >64 | >64 | >64 | >64 | >64 | >64 | >64 | >64 |

TABLE XI

ANTIBACTERIAL ACTIVITY OF 9-AMINOCARBONYLSUBSTITUTED DERIVATIVES OF
GLYCYLCYCLINES OF FORMULA I MINIMAL INHIBITORY CONCENTRATION MIC (UG/ML)

| | Water Example 58 | Mouse Serum Example 58 | Human Serum Example 58 | Water Example 59 | Mouse Serum Example 59 | Human Serum Example 59 | Water Example 60 | Mouse Serum Example 60 | Human Serum Example 60 |
|---|---|---|---|---|---|---|---|---|---|
| E. coli GC 2236 | >64 | >64 | >64 | >64 | >64 | >64 | >64 | >64 | >64 |
| E. coli GC 2231 | >64 | >64 | >64 | >64 | >64 | >64 | >64 | >64 | >64 |
| E. coli GC 2235 | >64 | >64 | >64 | >64 | >64 | >64 | >64 | 64 | 64 |
| E. coli GC 2232 | >64 | >64 | >64 | >64 | >64 | >64 | >64 | >64 | >64 |
| E. coli GC 2233 | >64 | >64 | >64 | >64 | >64 | >64 | >64 | >64 | >64 |
| E. coli GC 2234 | >64 | >64 | >64 | >64 | >64 | >64 | >64 | >64 | >64 |
| E. coli GC 2270 | >64 | >64 | >64 | >64 | >64 | >64 | >64 | >64 | >64 |
| E. coli GC 2271 | >64 | >64 | >64 | >64 | >64 | >64 | >64 | 64 | 64 |
| E. coli GC 2272 | >64 | >64 | >64 | >64 | 64 | >64 | 64 | 32 | 32 |
| E. coli GC 4559 | >64 | >64 | >64 | >64 | 64 | >64 | >64 | >64 | >64 |

TABLE XI-continued

ANTIBACTERIAL ACTIVITY OF 9-AMINOCARBONYLSUBSTITUTED DERIVATIVES OF
GLYCYLCYCLINES OF FORMULA I MINIMAL INHIBITORY CONCENTRATION MIC (UG/ML)

| | Water Example 58 | Mouse Serum Example 58 | Human Serum Example 58 | Water Example 59 | Mouse Serum Example 59 | Human Serum Example 59 | Water Example 60 | Mouse Serum Example 60 | Human Serum Example 60 |
|---|---|---|---|---|---|---|---|---|---|
| E. coli GC 4560 | 4 | 4 | 4 | 4 | 4 | 4 | 2 | 1 | 1 |
| E. coli GC 6465 | >64 | >64 | >64 | >64 | 32 | >64 | >64 | >64 | >64 |
| E. coli GC 3226 | >64 | >64 | >64 | >64 | >64 | >64 | >64 | >64 | >64 |
| E. coli GC 2203 | >64 | >64 | >64 | >64 | >64 | >64 | >64 | >64 | >64 |
| E. coli GC 1073 | >64 | >64 | >64 | >64 | >64 | >64 | >64 | >64 | >64 |
| Salmonella spp. GC 235 | >64 | >64 | >64 | >64 | >64 | >64 | >64 | >64 | >64 |
| Salmonella spp. GC 566 | >64 | >64 | >64 | >64 | >64 | >64 | >64 | >64 | >64 |
| S. cholerasius GC 1355 | >64 | >64 | >64 | >64 | >64 | >64 | >64 | >64 | >64 |
| S. typhimurium GC 2172 | >64 | >64 | >64 | >64 | >64 | >64 | >64 | >64 | >64 |
| P. aeruginosa GC 2214 | >64 | >64 | >64 | >64 | >64 | >64 | >64 | >64 | >64 |
| S. aureus GC 1131 | 4 | 2 | 4 | 4 | 4 | 4 | 8 | 2 | 2 |
| S. aureus GC 6466 | 4 | 2 | 4 | 8 | 4 | 4 | 8 | 4 | 4 |
| S. aureus GC 6467 | 4 | 2 | 4 | 4 | 4 | 4 | 8 | 4 | 4 |
| S. aureus GC 1079 | 8 | 2 | 4 | 8 | 4 | 2 | 4 | 2 | 2 |
| S. aureus GC 4536 | 4 | 2 | 4 | 4 | 4 | 4 | 4 | 2 | 2 |
| S. aureus GC 2216 | 4 | 2 | 4 | 4 | 4 | 4 | 4 | 2 | 2 |
| S. aureus GC 6335 | 4 | 4 | 4 | 4 | 4 | 4 | 8 | 8 | 8 |
| S. aureus GC 6469 | 4 | 2 | 4 | 4 | 4 | 4 | 4 | 2 | 2 |
| S. epidermidis GC 4935 | 8 | 4 | 4 | 4 | 4 | 4 | 16 | 8 | 8 |
| E. faecalis GC 4555 | 8 | 4 | 4 | 4 | 4 | 4 | 4 | 4 | 2 |
| E. faecalis GC 2265 | 4 | 4 | 4 | 4 | 4 | 4 | 8 | 8 | 4 |
| E. faecalis GC 2267 | 4 | 2 | 4 | 4 | 4 | 4 | 8 | 8 | 4 |
| E. faecalis GC 2242 | 4 | 2 | 4 | 4 | 2 | 4 | 8 | 8 | 4 |
| E. faecium GC 4556 | 4 | 2 | 4 | 4 | 4 | 4 | 4 | 4 | 4 |
| E. faecium GC 2243 | 4 | 2 | 4 | 4 | 4 | 8 | 4 | 2 | 2 |
| S. pneumoniae* GC 4465 | 2 | 2 | 4 | 4 | 4 | 4 | 2 | 1 | 1 |
| S. pneumoniae+ GC 4465 | 8 | 4 | 4 | 8 | 4 | 8 | 4 | 4 | 2 |
| S. pyogenes GC 4563 | 4 | 4 | 4 | 4 | 4 | 4 | 2 | 1 | 0.50 |
| S. agalactiae GC 4564 | 8 | 8 | 16 | 8 | 8 | 8 | 4 | 4 | 4 |
| c. albicans GC 3066 | >64 | >64 | >64 | >64 | >64 | >64 | >64 | >64 | >64 |

TABLE XII

ANTIBACTERIAL ACTIVITY OF 9-AMINOCARBONYLSUBSTITUTED DERIVATIVES OF
GLYCYLCYCLINES OF FORMULA I MINIMAL INHIBITORY CONCENTRATION MIC (UG/ML)

| | Water Example 61 | Mouse Serum Example 61 | Human Serum Example 61 | Water Example 62 | Mouse Serum Example 62 | Human Serum Example 62 | Water Example 63 | Mouse Serum Example 63 | Human Serum Example 63 |
|---|---|---|---|---|---|---|---|---|---|
| E. coli GC 2236 | 16 | 0.50 | 4 | 4 | 0.50 | 8 | >64 | 1 | >64 |
| E. coli GC 2231 | 32 | 1 | 8 | 8 | 0.50 | 4 | >64 | 1 | >64 |
| E. coli GC 2235 | 16 | 0.50 | 4 | 4 | 0.50 | 2 | >64 | 0.50 | >64 |
| E. coli GC 2232 | 16 | 0.50 | 4 | 8 | 1 | 2 | >64 | 1 | >64 |
| E. coli GC 2233 | 16 | 1 | 8 | 8 | 2 | 4 | >64 | 1 | >64 |
| E. coli GC 2234 | 16 | 0.50 | 8 | 8 | 1 | 2 | >64 | 1 | 64 |
| E. coli GC 2270 | 16 | 0.50 | 4 | 8 | 0.50 | 2 | >64 | 0.50 | 64 |
| E. coli GC 2271 | 16 | 0.50 | 4 | 4 | 1 | 2 | >64 | 0.50 | >64 |
| E. coli GC 2272 | 8 | 0.50 | 4 | 8 | 1 | 4 | >64 | 1 | >64 |
| E. coli GC 4559 | 64 | 1 | 8 | 16 | 1 | 8 | >64 | 2 | >64 |
| E. coli GC 4560 | 1 | 0.25 | 1 | 0.50 | 0.25 | 0.50 | 16 | 0.50 | 2 |
| E. coli GC 6465 | >64 | 1 | 32 | >64 | 2 | 8 | >64 | 2 | >64 |
| E. coli GC 3226 | 32 | 0.50 | 8 | 8 | 1 | 4 | >64 | 1 | >64 |
| E. coli GC 2203 | 32 | 0.50 | 8 | 16 | 1 | 4 | >64 | 1 | >64 |
| E. coli GC 1073 | 32 | 0.50 | 8 | 16 | 0.50 | 4 | >64 | 2 | >64 |
| Salmonella spp. GC 235 | >64 | 1 | 16 | >64 | 1 | 8 | >64 | 1 | >64 |
| Salmonella spp. GC 566 | >64 | 1 | 32 | >64 | 1 | 16 | >64 | 1 | >64 |
| S. cholerasius GC 1355 | >64 | 2 | 64 | >64 | 2 | 32 | >64 | 2 | >64 |
| S. typhimurium GC 2172 | >64 | 1 | 64 | >64 | 2 | 16 | >64 | 2 | >64 |
| P. aeruginosa GC 2214 | >64 | 8 | >64 | >64 | 16 | >64 | >64 | 32 | >64 |
| S. aureus GC 1131 | 0.50 | 0.50 | 0.50 | 0.50 | 0.50 | 0.50 | 4 | 1 | 1 |
| S. aureus GC 6466 | 0.50 | 0.50 | 0.50 | 0.25 | 0.50 | 0.50 | 2 | 0.50 | 1 |
| S. aureus GC 6467 | 1 | 0.50 | 0.50 | 0.50 | 1 | 0.50 | 16 | 2 | 4 |
| S. aureus GC 1079 | 1 | 0.25 | 0.50 | 0.50 | 1 | 0.50 | 8 | 1 | 2 |
| S. aureus GC 4536 | 0.50 | 0.50 | 0.50 | 0.50 | 0.50 | 0.50 | 4 | 1 | 1 |
| S. aureus GC 2216 | 1 | 0.50 | 0.50 | 0.50 | 0.50 | 0.50 | 4 | 1 | 1 |

TABLE XII-continued

ANTIBACTERIAL ACTIVITY OF 9-AMINOCARBONYLSUBSTITUTED DERIVATIVES OF GLYCYLCYCLINES OF FORMULA I MINIMAL INHIBITORY CONCENTRATION MIC (UG/ML)

| | Water Example 61 | Mouse Serum Example 61 | Human Serum Example 61 | Water Example 62 | Mouse Serum Example 62 | Human Serum Example 62 | Water Example 63 | Mouse Serum Example 63 | Human Serum Example 63 |
|---|---|---|---|---|---|---|---|---|---|
| *S. aureus* GC 6335 | 1 | 0.50 | 1 | 0.50 | 1 | 0.50 | 4 | 1 | 1 |
| *S. aureus* GC 6469 | 2 | 0.50 | 0.50 | 1 | 1 | 0.50 | 16 | 1 | 2 |
| *S. epidermidis* GC 4935 | 1 | 0.50 | 1 | 0.50 | 0.50 | 0.50 | 4 | 2 | 2 |
| *E. faecalis* GC 4555 | 2 | 1 | 2 | 1 | 1 | 0.50 | 4 | 1 | 2 |
| *E. faecalis* GC 2265 | 2 | 0.50 | 2 | 1 | 0.50 | 0.50 | 8 | 1 | 2 |
| *E. faecalis* GC 2267 | 2 | 0.50 | 2 | 1 | 0.50 | 0.50 | 16 | 1 | 2 |
| *E. faecalis* GC 2242 | 2 | 0.50 | 2 | 0.50 | 0.50 | 0.50 | 1 | 1 | 1 |
| *E. faecium* GC 4556 | 2 | 0.50 | 2 | 1 | 1 | 1 | 0.50 | 1 | 4 |
| *E. faecium* GC 2243 | 0.50 | 0.25 | 1 | 0.50 | 0.50 | 0.50 | 0.50 | 0.25 | 0.25 |
| *S. pneumoniae\** GC 4465 | 0.12 | 0.12 | 0.25 | 0.12 | 0.12 | 0.12 | 0.12 | 0.12 | 0.12 |
| *S. pneumoniae+* GC 4465 | 0.50 | 0.50 | 0.50 | 0.50 | 1 | 0.50 | 0.50 | 0.50 | 0.50 |
| *S. pyogenes* GC 4563 | 0.50 | 0.25 | 0.25 | 0.25 | 0.25 | 0.12 | 0.12 | 0.12 | 0.12 |
| *S. agalactiae* GC 4564 | 0.25 | 0.25 | 0.50 | 0.25 | 0.25 | 0.12 | 0.25 | 0.25 | 0.25 |
| *c. albicans* GC 3066 | >64 | >64 | >64 | >64 | >64 | >64 | >64 | >64 | >64 |

TABLE XIII

ANTIBACTERIAL ACTIVITY OF 9-AMINOCARBONYLSUBSTITUTED DERIVATIVES OF GLYCYLCYCLINES OF FORMULA I MINIMAL INHIBITORY CONCENTRATION MIC (UG/ML)

| | MouseSerum Example 108 | Water Example 108 | MouseSerum Example 109 | Water Example 109 | MouseSerum Example 109 | Water Example 109 | MouseSerum Example 110 | Water Example 110 |
|---|---|---|---|---|---|---|---|---|
| *E. coli* GC 2236 | 0.50 | 2 | 0.50 | 1 | 0.50 | 2 | 1 | 2 |
| *E. coli* GC 2231 | 2 | 4 | 0.50 | 1 | 1 | 2 | 4 | 8 |
| *E. coli* GC 2235 | 0.50 | 1 | 0.25 | 0.50 | 0.50 | 1 | 0.50 | 1 |
| *E. coli* GC 2232 | 1 | 2 | 0.50 | 1 | 0.50 | 2 | 1 | 2 |
| *E. coli* GC 2233 | 0.50 | 1 | 0.25 | 0.50 | 1 | 2 | 0.50 | 1 |
| *E. coli* GC 2234 | 0.50 | 2 | 0.12 | 0.25 | 0.25 | 2 | 1 | 2 |
| *E. coli* GC 2270 | 0.50 | 1 | 0.25 | 0.50 | 0.25 | 2 | 1 | 1 |
| *E. coli* GC 2271 | 0.50 | 0.50 | 0.12 | 0.25 | 0.25 | 1 | 1 | 2 |
| *E. coli* GC 2272 | 0.25 | 0.50 | 0.25 | 0.25 | 0.50 | 2 | 1 | 1 |
| *E. coli* GC 4559 | 0.50 | 1 | 0.12 | 0.25 | 1 | 2 | 2 | 2 |
| *E. coli* GC 4560 | 0.12 | 0.25 | <0.06 | <0.06 | 0.25 | 0.25 | 0.25 | 0.50 |
| *E. coli* GC 6465 | 8 | 64 | 1 | 4 | 4 | 16 | 64 | >64 |
| *E. coli* GC 3226 | 0.50 | 1 | 0.50 | 1 | 1 | 4 | 2 | 4 |
| *E. coli* GC 2203 | 0.50 | 1 | 0.50 | 1 | 0.50 | 2 | 1 | 4 |
| *E. coli* GC 1073 | 0.50 | 2 | 0.50 | 1 | 1 | 4 | 2 | 8 |
| *Salmonella* spp. GC 235 | 1 | 4 | 1 | 2 | 1 | 4 | 4 | 8 |
| *Salmonella* spp. GC 566 | 1 | 8 | 2 | 4 | 2 | 4 | 16 | 32 |
| *S. cholerasius* GC 1355 | 32 | 64 | 8 | 32 | 8 | 32 | >64 | >64 |
| *S. typhimurium* GC 2172 | 4 | 32 | 4 | 16 | 4 | 16 | 64 | >64 |
| *P. aeruginosa* GC 2214 | 16 | 32 | 16 | >64 | 32 | >64 | >64 | >64 |
| *S. aureus* GC 1131 | 0.25 | 0.50 | 1 | 2 | 1 | 4 | 2 | 4 |
| *S. aureus* GC 6466 | 0.50 | 1 | 0.50 | 1 | 0.50 | 4 | 1 | 2 |
| *S. aureus* GC 6467 | 2 | 8 | 2 | 4 | 2 | 8 | 32 | >64 |
| *S. aureus* GC 1079 | 2 | 4 | 2 | 4 | 2 | 8 | 16 | 16 |
| *S. aureus* GC 4536 | 0.50 | 1 | 1 | 2 | 1 | 4 | 4 | 4 |
| *S. aureus* GC 2216 | 0.50 | 1 | 1 | 2 | 0.50 | 8 | 2 | 4 |
| *S. aureus* GC 6335 | 1 | 2 | 2 | 4 | 1 | 4 | 8 | 8 |
| *S. aureus* GC 6469 | 0.25 | 1 | 1 | 2 | 2 | 8 | 32 | 32 |
| *S. epidermidis* GC 4935 | 1 | 2 | 2 | 4 | 2 | 8 | 4 | 8 |

TABLE XIII-continued

ANTIBACTERIAL ACTIVITY OF 9-AMINOCARBONYLSUBSTITUTED DERIVATIVES OF GLYCYLCYCLINES OF FORMULA I MINIMAL INHIBITORY CONCENTRATION MIC (UG/ML)

| | MouseSerum Example 108 | Water Example 108 | MouseSerum Example 109 | Water Example 109 | MouseSerum Example 109 | Water Example 109 | MouseSerum Example 110 | Water Example 110 |
|---|---|---|---|---|---|---|---|---|
| *E. faecalis* GC 4555 | 0.50 | 0.50 | 0.50 | 1 | 0.50 | 1 | 1 | 2 |
| *E. faecalis* GC 2265 | 1 | 2 | 1 | 2 | 1 | 4 | 8 | 4 |
| *E. faecalis* GC 2267 | 1 | 2 | 1 | 2 | 1 | 4 | 8 | 4 |
| *E. faecalis* GC 2242 | 0.50 | 1 | 1 | 1 | 1 | 2 | 1 | 1 |
| *E. faecium* GC 4556 | 0.50 | 1 | 1 | 2 | 1 | 2 | 1 | 2 |
| *E. faecium* GC 2243 | 0.50 | 0.50 | 0.50 | 0.50 | 0.50 | 1 | 0.50 | 0.50 |
| *S. pneumoniae**  GC 4465 | 0.12 | 0.12 | <0.06 | 0.12 | <0.06 | 0.25 | 0.25 | 0.12 |
| *S. pneumoniae+* GC 4465 | 1 | 2 | 1 | 1 | 1 | 2 | 4 | 2 |
| *S. pyogenes* GC 4563 | 0.12 | 0.12 | <0.06 | 0.12 | 0.12 | 0.25 | 0.12 | <0.06 |
| *S. agalactiae* GC 4564 | 0.12 | 0.12 | 0.12 | 0.25 | <0.06 | 0.25 | 0.25 | 0.25 |
| *c. albicans* GC 3066 | >64 | >64 | >64 | >64 | >64 | >64 | >64 | >64 |

TABLE 1

In vitro activity (MIC)$^a$ of representative examples of formula I

Minimum inhibitory concentration MIC (μg/ml)

| Ex Number | E. coli (Mouse Serum) | E. coli (Water) | Staph (Mouse Serum) | Staph (Water) |
|---|---|---|---|---|
| 1 | 0.5-1 | 16-64 | 1-4 | 1-8 |
| 2 | 1-4 | 32-64 | 1-8 | 2-8 |
| 3 | 1-2 | >64 | 1-4 | 4-32 |
| 4 | 0.5-2 | 64->64 | 0.5-2 | 2-16 |
| 5 | 1-2 | 16-64 | 0.25-2 | 0.5-4 |
| 6 | 1-2 | 8-64 | 0.5-2 | 1-4 |
| 7 | 0.25-2 | 2-16 | 0.5-4 | 0.5-4 |
| 8 | 1-2 | 16->64 | 0.5-4 | 1-8 |
| 9 | 0.5-2 | 4-64 | <0.06-2 | 0.12-2 |
| 10 | 0.25-2 | 4-32 | 0.25-2 | 0.12-2 |
| 11 | 0.25-2 | 4->64 | 0.25-4 | 0.25-4 |
| 12 | 0.5-2 | 16-64 | 0.5-4 | 1-16 |
| 13 | 1-4 | 8-16 | 1-4 | 2-8 |
| 14 | 32->64 | 64->64 | 1-8 | 2-8 |
| 15 | 32->64 | 32->64 | 2-16 | 4-16 |
| 16 | 16->16 | 64->64 | 2-8 | 4-8 |
| 17 | 0.5-2 | 32-64 | 1-4 | 2-32 |
| 18 | 0.5-2 | 4-8 | 1-4 | 1-4 |
| 19 | 0.5-2 | 32->64 | 0.5-4 | 1-8 |
| 20 | 0.5-2 | >64 | 1-4 | 64->64 |
| 21 | 0.5-8 | >64 | 1-4 | 32->64 |
| 22 | 1-8 | >64 | 0.5-4 | 2->64 |
| 23 | 1-8 | >64 | 0.25-4 | 0.5-8 |
| 24 | 0.5-2 | >64 | 0.25-4 | 0.5->64 |
| 25 | 1-2 | 32->64 | 0.25-2 | 0.5-4 |
| 26 | 1-4 | 64->64 | 0.25-1 | 0.25-4 |
| 27 | 0.5-1 | 32->64 | 0.12-2 | 0.12-2 |
| 28 | 0.25-1 | >64 | 0.5-4 | 4-64 |
| 29 | 0.5-1 | >64 | 0.25-2 | 1-4 |
| 30 | 0.5-1 | 32->64 | 0.25-2 | 1-8 |
| 31 | 0.5-1 | 16->64 | 0.25-2 | 0.5-4 |
| 32 | 0.5-1 | 1-4 | 0.25-2 | 0.5-4 |
| 33 | 0.5-2 | 32->64 | 0.12-2 | 0.12-2 |
| 34 | 0.5-1 | 4-16 | 0.25-4 | 0.25-4 |
| 35 | 4-8 | 8-64 | 2-4 | 2-4 |
| 36 | 2-8 | 8-32 | 2-4 | 4-16 |
| 37 | 2-4 | 4-32 | 1-4 | 2-4 |
| 38 | 0.5-4 | 64->64 | 0.5-2 | 1-8 |
| 39 | 1-4 | 16-32 | 1-4 | 2-16 |
| 40 | 1-2 | 16->64 | 0.25-2 | 0.25-2 |
| 41 | 0.5-4 | 16-64 | 0.5-4 | 1-8 |
| 42 | 4-16 | >64 | 2-4 | 4-8 |
| 43 | 0.25-2 | >64 | 0.5-2 | 32->64 |
| 44 | 2-8 | >64 | 2 | 2-4 |
| 45 | 0.5-2 | 16->64 | 0.25-1 | 0.5-2 |
| 46 | 0.5-2 | 64->64 | 0.25-1 | 0.25-2 |
| 47 | 0.5-2 | >64 | 1-2 | 2-4 |
| 48 | 0.25-2 | 32->64 | 0.12-2 | 0.12-2 |
| 49 | 0.25-2 | 8->64 | 0.12-1 | 0.12-2 |
| 50 | 1-2 | 32-64 | 0.25-2 | 0.25-4 |
| 51 | 1-2 | >64 | 0.25-2 | 1-4 |
| 52 | 0.5-1 | 4-16 | 0.5-1 | 2-4 |
| 53 | 0.25-1 | 16-64 | 0.25-1 | 0.5-2 |
| 54 | 0.5-1 | >64 | 0.5-2 | 1-4 |
| 55 | 0.5-8 | 64->64 | 1-2 | 2-8 |
| 56 | 0.25-2 | 8 > 64 | 0.25-1 | 1-4 |
| 57 | 0.5-4 | >64 | 0.5-2 | 4-16 |
| 58 | >64 | >64 | 2-4 | 4-8 |
| 59 | 32->64 | >64 | 4 | 4-8 |
| 60 | 32->64 | 64->64 | 2-8 | 4-16 |
| 61 | 0.5-1 | 8->64 | 0.25-0.5 | 0.5-2 |
| 62 | 0.5-2 | 4->64 | 0.5-1 | 0..25 – 1 |
| 63 | 0.5-2 | >64 | 0.5-2 | 2-16 |
| 64 | <0.12 | <0.12-1 | <0.12-0.25 | <0.12-0.5 |
| 65 | <0.12-0.5 | 16 | <0.12-0.5 | <0.12-1 |
| 66 | >128 | >128 | 1-16 | 2-16 |
| 67 | <0.12-0.25 | 8-32 | <0.12-0.25 | <0.12-1 |
| 68 | <0.12-1 | 2-8 | <0.12-0.25 | <0.12-1 |
| 69 | <0.12-0.5 | 8-64 | <0.12-0.25 | <0.12-1 |
| 70 | 4-8 | >64 | 1-4 | 2-4 |
| 71 | 0.12-0.25 | >64 | 0.5-1 | 32-64 |
| 72 | 0.5-1 | >64 | 0.5-1 | 4-8 |
| 73 | 0.5-1 | >64 | 1-4 | 4-8 |

TABLE 1-continued

In vitro activity (MIC)[a] of representative examples of formula I

Minimum inhibitory concentration MIC (μg/ml)

| Ex Number | E. coli (Mouse Serum) | E. coli (Water) | Staph (Mouse Serum) | Staph (Water) |
|---|---|---|---|---|
| 74 | 0.25-1 | >64 | 0.5-4 | 64->64 |
| 75 | 16->64 | >64 | 8-16 | 16-32 |
| 76 | 16->64 | >64 | 8-16 | 8-32 |
| 77 | 8->64 | >64 | 2-4 | 4-32 |
| 78 | 16-64 | >64 | 8 | 8-32 |
| 79 | 16->64 | >64 | 4 | 4-8 |
| 80 | 16->64 | 64->64 | 4-8 | 4-16 |
| 81 | 0.5-1 | 8-16 | 0.5-2 | 4-8 |
| 82 | 64->64 | >64 | 4-6 | 4-8 |
| 83 | 64->64 | >64 | 8-32 | 2-16 |
| 84 | 2-4 | >64 | 0.5-2 | 0.5-4 |
| 85 | 1-2 | >64 | 1-2 | 4-16 |
| 86 | 8-16 | >64 | 2-8 | 8 |
| 87 | 64->64 | >64 | 32-64 | >64 |
| 88 | 0.5-2 | 8-16 | 1-4 | 4-16 |
| 89 | 0.25-1 | 4-8 | 0.5-1 | 1-4 |
| 90 | 2-4 | >64 | 0.25-2 | 1-16 |
| 91 | 0.5-2 | >64 | 0.12-0.25 | 0.25-2 |
| 92 | 4-8 | >64 | 4 | 8-32 |
| 93 | 1-4 | 64->64 | 1-2 | 32-64 |
| 94 | 32-64 | >64 | 16-32 | >64 |
| 95 | >64 | >64 | 16->64 | >64 |
| 96 | 0.25-1 | 64->64 | 0.25-1 | 4-16 |
| 97 | 4-8 | >64 | 1-4 | 4-8 |
| 98 | 1-4 | >64 | 0.5-2 | 2-4 |
| 99 | 1-2 | >64 | 0.5-2 | 2-4 |
| 100 | 2 | 64->64 | 0.5-1 | 2-4 |
| 101 | 1 | 16-32 | 0.5-2 | 4-16 |
| 102 | 0.5-1 | >64 | 0.5-1 | 64->64 |
| 103 | 8-16 | >64 | 8-16 | 64->64 |
| 104 | 8-16 | >64 | 16-64 | 64->64 |
| 105 | 2 | >64 | 1-2 | 16->64 |
| 106 | >64 | >64 | >64 | >64 |
| 107 | >64 | 0.5-1 | 2-8 | 0.5-1 |
| 108 | 0.5-2 | 0.5-4 | 0.25-2 | 1-8 |
| 109 | 0.25-1 | 1-4 | 0.5-2 | 4-8 |
| 110 | 0.5-4 | 1-8 | 1-32 | 2->64 |
| 111 | 0.25-1 | 1-4 | 0.5-8 | 1-16 |
| 112 | 1-4 | 2-8 | 2-8 | 4-16 |
| 113 | 1-4 | 2-16 | 4-16 | 4-32 |

[a]Range of MIC (minimum inhibitory concentration) for E. coli and Staph., including MRSA which are selected from those E. coli and Staph., presented in Tables I-XIII.

Representative examples of compounds of Formula I were further evaluated for oral efficacy, stability in physiological pH in mouse serum and human plasma.

TABLE 3

In vitro activity (MIC)[a] of representative examples of compounds of Formula I

Minimum inhibitory concentration (MIC), μg/mL

| Ex. No. | E. coli (mouse serum) | E. coli (water) | Staph. (mouse serum) | Staph. (water) |
|---|---|---|---|---|
| 1 | 0.5-1 | 16-64 | 1-4 | 1-8 |
| 2 | 1-4 | 32-64 | 1-8 | 2-8 |
| 3 | 1-2 | >64 | 1-4 | 4-32 |
| 4 | 0.5-2 | 64->64 | 0.5-2 | 2-16 |
| 12 | 0.5-2 | 16-64 | 0.5-4 | 1-16 |
| 13 | 1-4 | 8-16 | 1-4 | 2-8 |
| 17 | 0.5-2 | 32-64 | 1-4 | 2-32 |
| 18 | 0.5-2 | 4-8 | 1-4 | 1-4 |
| 20 | 0.5-2 | >64 | 1-4 | 64->64 |
| 21 | 0.5-8 | >64 | 1-4 | 32->64 |
| 22 | 1-8 | >64 | 0.5-4 | 2->64 |
| 23 | 1-8 | >64 | 0.25-4 | 0.5-8 |
| 29 | 0.5-1 | >64 | 0.25-2 | 1-4 |
| 30 | 0.5-1 | 32->64 | 0.25-2 | 1-8 |
| 34 | 0.5-1 | 4-16 | 0.25-4 | 0.25-4 |
| 36 | 2-8 | 8-32 | 2-4 | 4-16 |
| 38 | 0.5-4 | 64->64 | 0.5-2 | 1-8 |
| 39 | 1-4 | 16-32 | 1-4 | 2-16 |

[a]Range of MIC (minimum inhibitory concentration) for E. coli and Staph., including MRSA which are selected from those E. coli and Staph., presented in Tables I-XIII.

TABLE 2

In vitro activity (MIC) of Example 87.

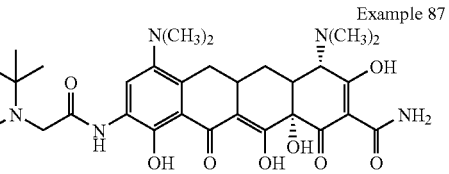

Example 87

| | water | Mouse serum | Human serum |
|---|---|---|---|
| E. coli, tet(A-D), efflux | >64 | 0.25-0.5 | >64 |
| E. coli, tet (M,S,O) Tet (M) | >64 | 0.25-0.5 | >64 |
| E. coli (susceptible) | >64 | 0.5 | >64 |
| E. coli (IMP) | 32 | <0.06 | 16 |
| S. aureus, tet (M) | 64 | 0.5 | 16 |
| S. aureus, tet (K), efflux | 64 | 1 | 32 |
| S. aureus (susceptible)[a] | 32 | 1 | 16 |
| Enterococcus spp. | 0.25-32 | 0.12-0.5 | 0.25-8 |
| Streptococcus spp. | 0.5-2 | <0.06 | 1-2 |
| C. albicans | >64 | >64 | >64 |

[a]Strain used for the in vivo testing

TABLE 4

In vitro activity (MIC)[a] of representative examples of compounds of Formula I

| Ex. No. | E. coli (mouse serum) | E. coli (water) | Staph. (mouse serum) | Staph. (water) |
|---|---|---|---|---|
| 5 | 1-2 | 16-64 | 0.25-2 | 0.5-4 |
| 6 | 1-2 | 8-64 | 0.5-2 | 1-4 |
| 7 | 0.25-2 | 2-16 | 0.5-4 | 0.5-4 |
| 8 | 1-2 | 16->54 | 0.5-4 | 1-8 |
| 9 | 0.5-2 | 4-64 | 0.06-1 | 0.12-2 |
| 10 | 0.25-2 | 4-32 | 0.25-2 | 0.12-2 |
| 11 | 0.25-2 | 4->64 | 0.25-4 | 0.25-4 |
| 19 | 0.5-2 | 32->64 | 0.5-4 | 1-8 |
| 24 | 0.5-2 | >64 | 0.25-4 | 0.5->64 |
| 25 | 1-2 | 32->64 | 0.25-2 | 0.5-4 |
| 26 | 1-4 | 64->64 | 0.25-1 | 0.25-4 |
| 27 | 0.5-1 | 32->64 | 0.12-2 | 0.12-2 |
| 28 | 0.25-1 | >64 | 0.5-4 | 4-64 |
| 31 | 0.5-1 | 16->64 | 0.25-2 | 0.5-4 |
| 33 | 0.5-2 | 32->64 | 0.12-2 | 0.12-2 |
| 35 | 4-8 | 8-64 | 2-4 | 2-4 |
| 40 | 1-2 | 16->64 | 0.25-2 | 0.25-2 |
| 41 | 0.5-4 | 16-64 | 0.5-4 | 1-8 |

[a]Range of MIC (minimum inhibitory concentration) for E. coli and Staph. including MRSA which are selected from those E. coli and Staph., presented in Tables I-XIII.

TABLE 5

In vitro activity (MIC) of Example 27

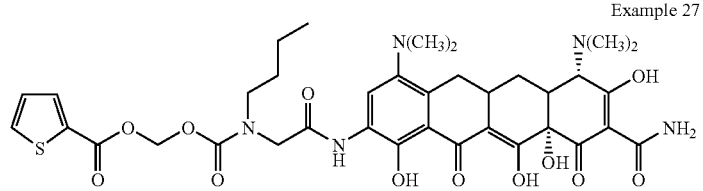

Example 27

| | water | Mouse serum | Human serum |
|---|---|---|---|
| E. coli, tet(A-D), efflux | 64->64 | 0.5-1 | 4-16 |
| E. coli, tet(M,S,O) Tet (M) | 0.5 | 0.5 | 4-8 |
| E. coli (susceptible) | 0.5 | 0.5 | 16 |
| E. coli (IMP) | 0.25 | 0.25 | 0.5 |
| S. aureus, tet (M) | 0.12 | 0.12 | 0.25 |
| S. aureus, tet (K), efflux | 1 | 1 | 1 |
| S. aureus (susceptible)[a] | 0.12 | 0.12 | 0.5 |
| Enterococcus spp. | 0.12-1 | 0.12-1 | 0.5-2 |
| Streptococcus spp. | <0.06-0.12 | <0.06-0.12 | 0.12-2 |
| C. albicans | >64 | >64 | >64 |

[a]Strain used for in vivo testing

Representative examples of compounds of Formula I were tested for the oral efficacy using S. aureus Smith in mice. The summary of in vivo and in vitro activities of selected compounds are listed in Table 6.

TABLE 6

In vitro and in vivo activity of representative examples of compounds of Formula I against Staph. aureus Smith in mice.

| | ED$_{50}$ mg/kg (Staph aureus Smith) | | µg/mL (Staph aureus Smith) |
|---|---|---|---|
| Ex. No. | SOD[b] | SIV[c] | MIC[a] |
| 42 | 5.68 | 1.43 | 8 |
| 44 | 4 | 0.75 | 4 |

TABLE 6-continued

In vitro and in vivo activity of representative examples of compounds of Formula I against Staph. aureus Smith in mice.

| | ED$_{50}$ mg/kg (Staph aureus Smith) | | µg/mL (Staph aureus Smith) |
|---|---|---|---|
| Ex. No. | SOD[b] | SIV[c] | MIC[a] |
| 45 | 5.9 | 0.66 | 1 |
| 47 | 14 | 1.2 | 4 |
| 48 | 10.1 | 1.1 | 0.25 |
| 49 | 16 | 0.92 | 0.25 |
| 50 | 16.88 | 1.65 | 0.5 |
| 52 | 10.69 | 1.29 | 2 |
| 53 | 5.08 | 0.73 | 1 |
| 54 | 8.4 | 0.83 | 0.5 |
| 87 | 12.82 | 0.83 | 32 |

[a]MIC (minimum inhibitory concentration)
[b]SOD (Single oral dose)
[c]SIV (Single intravenous dose)

Representative examples of compounds of Formula I were tested in vivo against gram-negative bacteria (E. coli) in mice. Results of the tests (MIC, oral and IV) are list in Table 7.

TABLE 7

In vivo (oral, iv) and in vitro (MIC)[a] activity of representative examples of compounds of Formula I against E. coli in mice.

| | ED$_{50}$ mg/kg (E. coli) | | µg/mL (E. coli) |
|---|---|---|---|
| Ex. No. | SOD[b] | SIV[c] | MIC |
| 5 | >64 | 3.17 | >64 |
| 42 | 30.3 | 3.1 | >64 |
| 44 | 42.8 | 2.85 | >64 |
| 45 | 64 | 1.8 | 64 |
| 48 | 29.8 | 1.7 | >64 |
| 49 | 49 | 2.2 | 64 |
| 50 | 29.8 | 1.7 | >64 |
| 52 | 43.7 | 3.78 | 8 |

TABLE 7-continued

In vivo (oral, iv) and in vitro (MIC)[a] activity of representative examples of compounds of Formula I against *E. coli* in mice.

| | $ED_{50}$ mg/kg (*E. coli*) | | µg/mL (*E. coli*) |
|---|---|---|---|
| Ex. No. | SOD[b] | SIV[c] | MIC |
| 53 | 46.88 | 2.25 | 32 |
| 54 | 29.2 | 2.16 | >64 |
| 87 | 60.4 | 3.6 | >64 |

[a]MIC (minimum inhibitory concentration)
[b]SOD (Single oral dose)
[c]SIV (Single intravenous dose)

Test results of in vivo activity are shown in Table 8 for representative examples of compounds of Formula I.

TABLE 8

In vivo (oral, iv) and in vitro (MIC)[a] activity of representative examples of compounds of Formula I, against *Staph aureus* Smith in mice.

| | $ED_{50}$ mg/kg (*Staph aureus* Smith) | | µg/mL (*Staph aureus* Smith) |
|---|---|---|---|
| Ex. No. | SOD[b] | SIV[c] | MIC |
| 1 | 4.7 | 0.6 | 4 |
| 5 | 8.51 | 0.5 | 1 |
| 19 | 8.05 | 0.31 | 1 |
| 26 | 8.79 | 0.43 | 0.5 |
| 27 | 3.9 | 0.44 | 0.12 |
| 28 | 6.61 | 0.6 | 32 |
| 33 | 4.91 | 0.48 | 0.12 |
| 35 | 3.5 | 0.43 | 4 |
| 36 | 5.15 | 0.84 | 8 |
| 38 | 5.3 | 0.6 | 2 |
| 40 | 4.65 | 0.39 | 0.5 |

[a]MIC (minimum inhibitory concentration)
[b]SOD (Single oral dose)
[c]SIV (Single intravenous dose)

TABLE 9

| | Minimum inhibitory concentration (MIC), µg/mL | | | |
|---|---|---|---|---|
| Ex No. | *E. coli* (Human Serum) | *E. coli* (Water) | *Staph* (Human Serum) | *Staph* (Water) |
| 4 | 8-32 | 32->64 | 0.5-4 | 2-8 |
| 19 | 8-32 | 16->64 | 0.12-1 | 0.25-4 |
| 27 | 4-16 | 64->64 | 0.25-2 | 0.5-4 |
| 42 | >64 | >64 | 2-4 | 4-8 |
| 43 | >64 | >64 | 4-64 | 32->64 |
| 44 | >64 | >64 | 2-4 | 2-4 |
| 45 | 4-16 | 16->64 | 0.12-1 | 0.5-2 |
| 46 | 4-16 | 64->64 | 0.25-1 | 0.25-2 |
| 47 | 16->64 | >64 | 1-4 | 2-4 |
| 48 | 8->64 | 32->64 | 0.12-2 | 0.12-2 |
| 49 | 4-32 | 8->64 | 0.12-1 | 0.12-2 |
| 50 | 4-16 | 32-64 | 0.25-2 | 0.25-4 |
| 51 | 32-64 | >64 | 0.25-2 | 1-4 |
| 52 | 4-16 | 4-16 | 0.5-4 | 2-4 |
| 53 | 8-16 | 16-64 | 0.5-2 | 0.5-2 |
| 54 | 16-32 | >64 | 0.5-2 | 1-4 |
| 55 | 32->64 | 64->64 | 1-4 | 2-8 |
| 56 | 4-32 | 8->64 | 0.25-2 | 1-4 |
| 57 | >64 | >64 | 1-8 | 4-16 |
| 58 | >64 | >64 | 4 | 4-8 |
| 59 | >64 | >64 | 2-4 | 4-8 |
| 60 | 32->64 | 64->64 | 2-8 | 4-16 |
| 61 | 4-32 | 8->64 | 0.5-1 | 0.5-2 |
| 62 | 2-8 | 4->64 | 0.5 | 0.25-1 |
| 63 | 64->64 | >64 | 1-4 | 2-16 |
| 102 | 64->64 | | >64 | |
| 105 | 64 > 64 | | 8->64 | |

TABLE 10

| | $ED_{50}$ (mg/kg) Staph Smith | | $ED_{50}$ mg/kg *E. coli* #311 | | IV - RAT 2 mg/kg | | | PO - RAT 20 mg/kg | | |
|---|---|---|---|---|---|---|---|---|---|---|
| Ex. No. | SOD | SIV | SOD | SIV | Cmax | AUC | T½ | Cmax | AUC | % BA |
| 1 | | | | | | | | | | |
| 2 | 13.27 | 0.71 | | | | | | | | |
| 3 | 16.05 | 0.59 | | | | | | | | |
| 4 | 11.6 | 0.39 | >32 | >2 | | | | | | |
| 5 | 8.51 | 0.5 | | | | | | | | |
| 6 | 20.05 | 0.87 | | | | | | | | |
| 7 | 16.1 | 0.52 | | | | | | | | |
| 8 | 16.63 | 0.48 | | | | | | | | |
| 9 | 11.27 | 0.32 | | | | | | | | |
| 10 | 13.62 | 0.36 | | | | | | | | |
| 11 | 30.27 | 0.59 | | | | | | | | |
| 12 | 15.02 | 1 | | | | | | | | |
| 13 | 10.98 | 0.82 | | | | | | | | |
| 14 | >32 | >2 | | | | | | | | |
| 16 | >32 | >2 | | | | | | | | |
| 17 | 59.9 | 1.07 | | | | | | | | |
| 18 | 29.02 | 0.6 | | | | | | | | |
| 19 | 8.05 | 0.31 | >32 | >2 | | | | | | |
| 20 | 19.4 | 0.6 | | | | | | | | |
| 21 | >32 | 0.77 | | | | | | | | |
| 22 | 18.77 | 0.43 | | | | | | | | |
| 23 | 19.01 | 0.47 | | | | | | | | |
| 24 | 27 | 0.59 | | | | | | | | |
| 25 | 15.71 | 0.56 | | | | | | | | |
| 26 | 8.79 | 0.43 | | | | | | | | |
| 27 | 3.9 | 0.44 | >32 | >2 | | | | | | |
| 28 | 6.61 | 0.6 | >32 | >2 | | | | | | |

TABLE 10-continued

| Ex No | | | | | | | | | | |
|---|---|---|---|---|---|---|---|---|---|---|
| 29 | 13.67 | 0.43 | | | | | | | | |
| 30 | 15.1 | 0.41 | | | | | | | | |
| 31 | 11.11 | 0.31 | | | | | | | | |
| 32 | 7.7 | 0.56 | | | | | | | | |
| 33 | 4.91 | 0.45 | | | | | | | | |
| 34 | 12.86 | 0.71 | | | | | | | | |
| 35 | 3.5 | 0.43 | | | | | | | | |
| 36 | 5.15 | 0.84 | | | | | | | | |
| 37 | 4.1 | 0.55 | | | | | | | | |
| 38 | 5.3 | 0.6 | | | | | | | | |
| 39 | 13.3 | 0.6 | | | | | | | | |
| 40 | 4.65 | 0.39 | | | | | | | | |
| 41 | 11.3 | 0.83 | | | | | | | | |
| 42 | 5.68 | 1.43 | 30.3 | 3.1 | 4.1 | 1.6 | 5.1 | 0.22 | 0.64 | 8.1 |
| 43 | 12.82 | 0.83 | 60.4 | 3.6 | | | | | | |
| 44 | 4 | 0.75 | 42.8 | 2.85 | 6.5 | 2.4 | 3.5 | 0.05 | 0.27 | 2.3 |
| 45 | 5.9 | 0.66 | 64 | 1.8 | | | | | | |
| 46 | 8.4 | 0.83 | 29.2 | 2.16 | | | | | | |
| 47 | 14 | 1.2 | >64 | 3.17 | | | | | | |
| 48 | 10.1 | 1.1 | 29.8 | 1.7 | | | | | | |
| 49 | 16.6 | 0.92 | 49 | 2.2 | | | | | | |
| 50 | 16.88 | 1.65 | >64 | 2.59 | | | | | | |
| 52 | 10.69 | 1.29 | 43.7 | 3.78 | | | | | | |
| 53 | 5.08 | 0.73 | 46.88 | 2.25 | | | | | | |
| 54 | >16 | 1.17 | >32 | 3.72 | | | | | | |
| 55 | >16 | 1.81 | 32 | 4.69 | | | | | | |
| 56 | >16 | 0.79 | | | | | | | | |
| 57 | 6.36 | 1.17 | | | | | | | | |
| 58 | | | >32 | >8 | | | | | | |
| 59 | | | >32 | >8 | | | | | | |
| 60 | | | >32 | >8 | | | | | | |
| 61 | | | >32 | 2–4 | | | | | | |
| 62 | | | >32 | 4–8 | | | | | | |
| 63 | | | >32 | 4–8 | | | | | | |
| 71 | >32 | 1 | >32 | >4 | | | | | | |
| 74 | >32 | 1.08 | >32 | >4 | | | | | | |
| 81 | 16–32 | >4 | | | | | | | | |
| 82 | 21.97 | 0.52 | | | | | | | | |
| 90 | 16–32 | 0.5–1 | | | | | | | | |
| 91 | 11.73 | 1.21 | | | | | | | | |
| 93 | >32 | 0.5–1 | | | | | | | | |
| 96 | 16–32 | 1–2 | >32 | 2–4 | | | | | | |
| 102 | 19.81 | 1.59 | >32 | 2–4 | | | | | | |
| 108 | >32 | >2 | | | | | | | | |
| 109 | 19.94 | 0.76 | | | | | | | | |
| 110 | 31.94 | 0.6 | | | | | | | | |
| 112 | 6.12 | 0.48 | | | | | | | | |
| 113 | 7.01 | 0.4 | | | | | | | | |

| | IV - DOG 2 mg/kg | | | Oral - DOG 10 mg/kg | | | IV - MONKEY 2 mg/kg | | | Oral - MONKEY 10 mg/kg | | |
|---|---|---|---|---|---|---|---|---|---|---|---|---|
| Ex No | Cmax | AUC | T½ | Cmax | AUC | % BA | Cmax | AUC | T½ | Cmax | AUC | % BA |
| 1 | 10.8 | 8.3 | 14.9 | 0.11 | 0.67 | 1.6% | 9.1 | 3.3 | 17.6 | no levels detected | | |
| 27 | 1.9 | 9.8 | 10.7 | 0.018 | 0.22 | 0.5% | 20 | 9.3 | 7.3 | 0.04 | 0.21 | 0.5% |
| 28 | 0.55 | 6 | 7.8 | 0.09 | 0.74 | 2.5% | 0.77 | 3.6 | 13.2 | 0.05 | 0.23 | 1.3% |

When the compounds of the invention are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight may be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The present invention further provides a method of treating bacterial infections in warm-blooded animals including man, which comprises providing to the afflicted warm-blooded animals an antibacterially effective amount of a compound or a pharmaceutical composition of a compound of the invention.

The invention will be more fully described in conjunction with the following specific examples which are not to be construed as limiting the scope of the invention.

Reference Compound 1

(Tert-butyl-chloromethoxycarbonyl-amino)-acidic acid benzyl ester

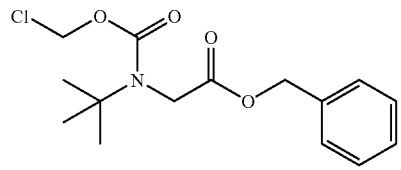

To a solution of tert-butylamino-acetic acid benzyl ester in dichloromethane is added two equivalents of [1,8-bis(dimethylamino)naphthalene, N,N, N',N'-tetramethyl-1,8-naphthalenediamine]. The reaction mixture is than cooled in an ice bath and one equivalent of chloromethyl chloroformate is added. The reaction is then warm to room temperature and continue to stir for 24 hr. It is then washed with water and then brine.

Reference Compound 2

3,3-Dimethyl-butyric acid (benzyloxycarbonylmethyl-tert-butyl-carbamoyloxy)-methyl ester

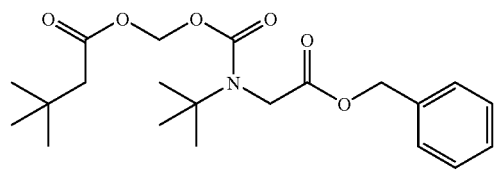

Tert-butylacetic acid and 1.0 M tetrabutylammonium hydroxide in methanol is stirred for an hour, methanol is removed and THF is added. To this solution is then added benzyl N-(tert-butyl)-N-[(chloromethoxy)carbonyl]glycinate and stirred at room temperature for 24 hr. Solvent is removed and residue is diluted with ether, then washed with water, then brine. It is dried over magnesium sulfate, filtered and solvent removed.

MS (ESI) m/z 394.25

Reference Compounds 3-55 (Table A)

Substantially following the method described in detail hereinabove in Reference Compound 2 using (tert-butyl-chloromethoxycarbonyl-amino)-acidic acid benzyl ester from Reference Compound 1 and the appropriate carboxylic acid, the reference compounds 3-55 of this invention listed below in Table A are prepared.

TABLE A

| Ref. Cpd. No. | Name | Spectra |
|---|---|---|
| 3 | ({[[2-(benzyloxy)-2-oxoethyl](tert-butyl)amino]carbonyl}oxy)methyl 4-tert-butylbenzoate | MS (ESI) m/z 456.23 |
| 4 | ({[[2-(benzyloxy)-2-oxoethyl](tert-butyl)amino]carbonyl}oxy)methyl 2,2-dimethylbutanoate | MS m/z 01-400386LMS; |

TABLE A-continued

| Ref. Cpd. No. | Name | Spectra |
|---|---|---|
| 5 | ({[[2-(benzyloxy)-2-oxoethyl](tert-butyl)amino]carbonyl}oxy)methyl 2-methylpropanoate | MS (ESI) m/z 366.24; HRMS: calcd for C19H27NO6 + Na+, 388.17306; found (ESI+, [M + NA]1+), 388.17295; |
| 6 | ({[[2-(benzyloxy)-2-oxoethyl](tert-butyl)amino]carbonyl}oxy)methyl cyclopentanecarboxylate | MS (ESI) m/z 392.23; |
| 7 | ({[[2-(benzyloxy)-2-oxoethyl](tert-butyl)amino]carbonyl}oxy)methyl 4-methylbenzoate | MS (ESI) m/z 414.24; MS (ESI) m/z 436.23; HRMS: calcd for C23H27NO6 + Na+, 436.17306; found (ESI+, [M + NA]1+), 436.17291; |
| 8 | ({[[2-(benzyloxy)-2-oxoethyl](tert-butyl)amino]carbonyl}oxy)methyl heptanoate | MS (ESI) m/z 408.24; |
| 9 | ({[[2-(benzyloxy)-2-oxoethyl](tert-butyl)amino]carbonyl}oxy)methyl propionate | MS (ESI) m/z 352.17; HRMS: calcd for C18H25NO6 + H+, 352.17546; found (ESI+, [M + H]+), 352.17551; |
| 10 | ({[[2-(benzyloxy)-2-oxoethyl](tert-butyl)amino]carbonyl}oxy)methyl cyclohexanecarboxylate | MS (ESI) m/z 406.26; |
| 11 | ({[[2-(benzyloxy)-2-oxoethyl](tert-butyl)amino]carbonyl}oxy)methyl 3,5-dimethylbenzoate MS (ESI) m/z 428.25; MS (ESI) m/z 87.54; | MS (ESI) m/z 428.25; MS (ESI) m/z 87.54; |
| 12 | ({[[2-(benzyloxy)-2-oxoethyl](tert-butyl)amino]carbonyl}oxy)methyl 4-fluorobenzoate | MS (ESI) m/z 418.2; MS (ESI) m/z 440.2; |
| 13 | ({[[2-(benzyloxy)-2-oxoethyl](tert-butyl)amino]carbonyl}oxy)methyl 3-methylbutanoate | MS (ESI) m/z 380.27; HRMS: calcd for C20H29NO6 + Na+, 402.18871; found (ESI+, [M + NA]1+), 402.18882; |
| 14 | benzyl N-(tert-butyl)-N-({[(cyclopentylacetyl)oxy]methoxy}carbonyl)glycinate | MS (ESI) m/z 406.2; |
| 15 | ({[[2-(benzyloxy)-2-oxoethyl](tert-butyl)amino]carbonyl}oxy)methyl 4-(trifluoromethyl)benzoate | MS (CI(ISOBUTANE)) m/z 468.13; |
| 16 | ({[[2-(benzyloxy)-2-oxoethyl](tert-butyl)amino]carbonyl}oxy)methyl cyclopropanecarboxylate | MS (ESI) m/z 364.26; |
| 17 | ({[[2-(benzyloxy)-2-oxoethyl](tert-butyl)amino]carbonyl}oxy)methyl adamantane-1-carboxylate | MS (ESI) m/z 458.3; |
| 18 | ({[[2-(benzyloxy)-2-oxoethyl](tert-butyl)amino]carbonyl}oxy)methyl pentanoate | MS (ESI) m/z 380.2; |
| 19 | ({[[2-(benzyloxy)-2-oxoethyl](tert-butyl)amino]carbonyl}oxy)methyl cyclobutanecarboxylate | MS (ESI) m/z 378.2; MS (ESI) m/z 400.2; |
| 20 | ({[[2-(benzyloxy)-2-oxoethyl](tert-butyl)amino]carbonyl}oxy)methyl 3-cyclohexylpropanoate | MS (ESI) m/z 434.3; MS (ESI) m/z 451.3; HRMS: calcd for C24H35NO6 + Na+, 456.23566; found (ESI+, [M + NA]1+), 456.23661; |
| 21 | benzyl N-(tert-butyl)-N-[({[(4-fluorophenoxy)acetyl]oxy}methoxy)carbonyl]glycinate | |

TABLE A-continued

| Ref. Cpd. No. | Name | Spectra |
|---|---|---|
| 22 | benzyl N-(tert-butyl)-N-({[(cyclohexylacetyl)oxy]methoxy}carbonyl)glycinate | MS (ESI) m/z 420.2; MS (ESI) m/z 442.2; |
| 23 | ({[[2-(benzyloxy)-2-oxoethyl](tert-butyl)amino]carbonyl}oxy)methyl 2,6-dimethylbenzoate | MS (ESI) m/z 428.2; |
| 24 | benzyl N-(tert-butyl)-N-({[(phenylacetyl)oxy]methoxy}carbonyl)glycinate | MS (ESI) m/z 414.2; MS (ESI) m/z 436.2; HRMS: calcd for C23H27NO6 + H+, 414.19112; found (ESI+, [M + H]1+), 414.19143; |
| 25 | ({[[2-(benzyloxy)-2-oxoethyl](tert-butyl)amino]carbonyl}oxy)methyl pivalate | MS (ESI) m/z 380.1; MS (ESI) m/z 781.3; HRMS: calcd for C20H29NO6 + H+, 380.20677; found (ESI+, [M + H]1+), 380.20649; |
| 26 | ({[[2-(benzyloxy)-2-oxoethyl](tert-butyl)amino]carbonyl}oxy)methyl 1-benzofuran-2-carboxylate | MS (ESI) m/z 440; MS (ESI) m/z 901.1; HRMS: calcd for C24H25NO7 + H+, 440.17038; found (ESI+, [M + H]1+), 440.17005; |
| 27 | ({[[2-(benzyloxy)-2-oxoethyl](tert-butyl)amino]carbonyl}oxy)methyl 1-methyl-1H-pyrrole-2-carboxylate | MS (ESI) m/z 403.3; MS (ESI) m/z 827.7; |
| 28 | ({[[2-(benzyloxy)-2-oxoethyl](tert-butyl)amino]carbonyl}oxy)methyl 1,1'-biphenyl-4-carboxylate | MS (ESI) m/z 476.2; HRMS: calcd for C28H29NO6 + Na+, 498.18871; found (ESI+, [M + NA]1+), 498.18857; |
| 29 | ({[[2-(benzyloxy)-2-oxoethyl](tert-butyl)amino]carbonyl}oxy)methyl 4-methoxybenzoate | MS (ESI) m/z 430.3; MS (ESI) m/z 452.3; |
| 30 | ({[[2-(benzyloxy)-2-oxoethyl](tert-butyl)amino]carbonyl}oxy)methyl 1H-indole-2-carboxylate | MS (ESI) m/z 439.1; HRMS: calcd for C24H26N2O6 + Na+, 461.16831; found (ESI+, [M + NA]1+), 461.168; |
| 31 | benzyl N-(tert-butyl)-N-({[(diphenylacetyl)oxy]methoxy}carbonyl)glycinate | MS (ESI) m/z 490.2; |
| 32 | ({[[2-(benzyloxy)-2-oxoethyl](tert-butyl)amino]carbonyl}oxy)methyl 1-naphthoate | MS (ESI) m/z 450.1; |
| 33 | ({[[2-(benzyloxy)-2-oxoethyl](tert-butyl)amino]carbonyl}oxy)methyl 2-naphthoate | MS (ESI) m/z 450.1; |
| 34 | ({[[2-(benzyloxy)-2-oxoethyl](tert-butyl)amino]carbonyl}oxy)methyl 1-methyl-1H-indole-3-carboxylate | MS (ESI) m/z 453.3; MS (ESI) m/z 905.6; MS (ESI) m/z 927.5; |
| 35 | ({[[2-(benzyloxy)-2-oxoethyl](tert-butyl)amino]carbonyl}oxy)methyl quinoline-2-carboxylate | MS (ESI) m/z 451.2; MS (ESI) m/z 901.4; |
| 36 | ({[[2-(benzyloxy)-2-oxoethyl](tert-butyl)amino]carbonyl}oxy)methyl nicotinate | MS (ESI) m/z 401.1; |
| 37 | ({[[2-(benzyloxy)-2-oxoethyl](tert-butyl)amino]carbonyl}oxy)methyl isonicotinate | MS (ESI) m/z 401; |

TABLE A-continued

| Ref. Cpd. No. | Name | Spectra |
|---|---|---|
| 38 | ({[[2-(benzyloxy)-2-oxoethyl](tert-butyl)amino]carbonyl}oxy)methyl 2,6-difluorobenzoate | MS (ESI) m/z 436.2; MS (ESI) m/z 893.4; MS (ESI) m/z 453.2; |
| 39 | ({[[2-(benzyloxy)-2-oxoethyl](tert-butyl)amino]carbonyl}oxy)methyl 2-fluorobenzoate | MS (ESI) m/z 418.2; MS (ESI) m/z 857.5; MS (ESI) m/z 440.2; |
| 40 | ({[[2-(benzyloxy)-2-oxoethyl](tert-butyl)amino]carbonyl}oxy)methyl 2-(trifluoromethyl)benzoate | MS (ESI) m/z 468.1; MS (ESI) m/z 490.2; |
| 41 | ({[[2-(benzyloxy)-2-oxoethyl](tert-butyl)amino]carbonyl}oxy)methyl 4-(1H-pyrrol-1-yl)benzoate | MS (ESI) m/z 465.1; MS (ESI) m/z 482.1; |
| 42 | ({[[2-(benzyloxy)-2-oxoethyl](tert-butyl)amino]carbonyl}oxy)methyl 1,1'-biphenyl-2-carboxylate | MS (ESI) m/z 476.3; MS (ESI) m/z 493.3; MS (ESI) m/z 951.6; |
| 43 | ({[[2-(benzyloxy)-2-oxoethyl](tert-butyl)amino]carbonyl}oxy)methyl 2,4,6-trimethylbenzoate | MS (ESI) m/z 442.3; MS (ESI) m/z 459.3; |
| 44 | ({[[2-(benzyloxy)-2-oxoethyl](tert-butyl)amino]carbonyl}oxy)methyl 4-isopropoxybenzoate | MS (ESI) m/z 458.3; |
| 45 | ({[[2-(benzyloxy)-2-oxoethyl](tert-butyl)amino]carbonyl}oxy)methyl 3,4,5-trimethoxybenzoate | MS (ESI) m/z 490.3; MS (ESI) m/z 996.5; MS (ESI) m/z 979.5; |
| 46 | ({[[2-(benzyloxy)-2-oxoethyl](tert-butyl)amino]carbonyl}oxy)methyl 3,5-dimethoxybenzoate | MS (ESI) m/z 460.3; MS (ESI) m/z 936.5; MS (ESI) m/z 919.5; |
| 47 | 3-phenyl-acrylic acid (benzyloxycarbonylmethyl-tert-butyl-carbamoyloxy)-methyl ester | PE added cpd |
| 48 | ({[[2-(benzyloxy)-2-oxoethyl](tert-butyl)amino]carbonyl}oxy)methyl 3-methyl-1-benzofuran-2-carboxylate | MS (ESI) m/z 454.2; MS (ESI) m/z 907.5; HRMS: calcd for C25H27NO7 + Na+, 476.16797; found (ESI, [M + NA]1+), 476.16858; |
| 49 | benzyl N-{[({[3,5-biS(trifluoromethyl)phenyl]acetyl}oxy)methoxy]carbonyl}-N-(tert-butyl)glycinate | MS m/z 01-305267LMS; HRMS: calcd for C25H25F6NO6 + Na+, 572.14783; found (ESI+, [M + NA]1+), 572.14702; |
| 50 | ({[[2-(benzyloxy)-2-oxoethyl](tert-butyl)amino]carbonyl}oxy)methyl 4-(heptyloxy)benzoate | MS (ESI) m/z 514.3; HRMS: calcd for C29H39NO7 + H+, 514.27993; found (ESI+, [M + H]1+), 514.28023; |
| 51 | ({[[2-(benzyloxy)-2-oxoethyl](tert-butyl)amino]carbonyl}oxy)methyl 2-(2-phenylethyl)benzoate | MS (ESI) m/z 526.2; |

TABLE A-continued

| Ref. Cpd. No. | Name | Spectra |
|---|---|---|
| 52 | ({[[2-(benzyloxy)-2-oxoethyl](tert-butyl)amino]carbonyl}oxy)methyl 4-(dodecyloxy)benzoate | MS (ESI) m/z 584.3; HRMS: calcd for C34H49NO7 + H+, 584.35818; found (ESI+, [M + H]1+), 584.3574; |
| 53 | ({[[2-(benzyloxy)-2-oxoethyl](tert-butyl)amino]carbonyl}oxy)methyl 4-(acetylamino)benzoate | MS (ESI) m/z 457.2; MS (ESI) m/z 913.4; HRMS: calcd for C24H28N2O7 + Na+, 479.17887; found (ESI+, [M + NA]1+), 479.17909; |
| 54 | ({[[2-(benzyloxy)-2-oxoethyl](tert-butyl)amino]carbonyl}oxy)methyl anthracene-9-carboxylate | MS (ESI) m/z 500.2; MS (ESI) m/z 999.5; |
| 55 | ({[[2-(benzyloxy)-2-oxoethyl](tert-butyl)amino]carbonyl}oxy)methyl 4-benzoylbenzoate | MS (ESI) m/z 504.2; |

Reference Compound 56

3,3-Dimethyl-butyric (tert-butyl-carboxymethyl-carbamoyloxy)-methyl ester

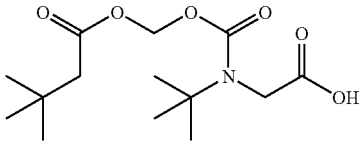

The product from Reference Compound 2, 10% palladium on carbon in ethyl acetate is hydrogenated in a Parr shaker at ca. 40 psi for about an hour. The catalyst is filtered and solvent removed to give the corresponding carboxylic acid product of the example MS(ESI) m/z 394.25.

Reference Examples 57-108 (Table B)

Substantially following the method described in detail hereinabove in Reference Compound 56 the reference compounds 57-108 of this invention listed below in Table B are prepared using the appropriate benzyl esters of Reference Compounds 3-55.

TABLE B

| Ref. Cpd. No. | Name | Spectra |
|---|---|---|
| 57 | N-(tert-butyl)-N-({[(4-tert-butylbenzoyl)oxy]methoxy}carbonyl)glycine | MS (ESI) m/z 366.18 |
| 58 | N-(tert-butyl)-N-{[(isobutyryloxy)methoxy]carbonyl}glycine | MS (ESI) m/z 274.05; MS (ESI) m/z 549.13; HRMS: calcd for C12H21NO6 + H+, 276.14416; found (ESI+, [M + H]1+), 276.14314; |
| 59 | N-(tert-butyl)-N-({[(cyclopentylcarbonyl)oxy]methoxy}carbonyl)glycine | MS (ESI) m/z 300.04; MS (ESI) m/z 601.1; HRMS: calcd for 2 C14H23NO6 − H+, 601.29780; found (ESI−, [2M − H]1−), 601.29741; |

TABLE B-continued

| Ref. Cpd. No. | Name | Spectra |
|---|---|---|
| 60 | N-(tert-butyl)-N-({[(4-methylbenzoyl)oxy]methoxy}carbonyl)glycine | MS (ESI) m/z 324.19; HRMS: calcd for C16H21NO6 + Na+, 346.12611; found (ESI+, [M + NA]1+), 346.12625; |
| 61 | N-(tert-butyl)-N-{[(heptanoyloxy)methoxy]carbonyl}glycine | MS (ESI) m/z 316.25; MS (ESI) m/z 633.54; |
| 62 | N-(tert-butyl)-N-{[(propionyloxy)methoxy]carbonyl}glycine | MS (ESI) m/z 260.05; MS (ESI) m/z 521.13; HRMS: calcd for C11H19NO6 + Na+, 284.11046; found (ESI, [M + NA]+), 284.11017; |
| 63 | N-(tert-butyl)-N-({[(cyclohexylcarbonyl)oxy]methoxy}carbonyl)glycine | MS (ESI) m/z 314.06; MS (ESI) m/z 629.14; HRMS: calcd for 2 C15H25NO6 − H+, 629.32910; found (ESI−, [2M − H]1−), 629.32842; |
| 64 | N-(tert-butyl)-N-({[(3,5-dimethylbenzoyl)oxy]methoxy}carbonyl)glycine | MS (ESI) m/z 338.16; |
| 65 | N-(tert-butyl)-N-({[(4-fluorobenzoyl)oxy]methoxy}carbonyl)glycine | MS (ESI) m/z 326; MS (ESI) m/z 653; HRMS: calcd for C15H18FNO6 + Na+, 350.10103; found (ESI+, [M + NA]1+), 350.10131; |
| 66 | N-(tert-butyl)-N-({[(3-methylbutanoyl)oxy]methoxy}carbonyl)glycine | HRMS: calcd for C13H23NO6 + Na+, 312.14176; found (ESI+, [M + NA]1+), 312.14197; |
| 67 | N-(tert-butyl)-N-({[(cyclopentylacetyl)oxy]methoxy}carbonyl)glycine | MS (ESI) m/z 314; MS (ESI) m/z 629.1; HRMS: calcd for C15H25NO6 + H+, 316.17546; found (ESI+, [M + H]1+), 316.17503; |
| 68 | N-(tert-butyl)-N-[({[4-(trifluoromethyl)benzoyl]oxy}methoxy)carbonyl]glycine | MS (ESI) m/z 376; MS (ESI) m/z 752.9; |

TABLE B-continued

| Ref. Cpd. No. | Name | Spectra |
|---|---|---|
| 69 | N-(tert-butyl)-N-({[(cyclopropylcarbonyl)oxy]methoxy}carbonyl)glycine | HRMS: calcd for C12H19NO6 + Na+, 296.11046; found (ESI+, [M + NA]1+), 296.11061; |
| 70 | N-({[(1-adamantylcarbonyl)oxy]methoxy}carbonyl)-N-(tert-butyl)glycine | MS (ESI) m/z 368.21; MS (ESI) m/z 757.37; |
| 71 | N-(tert-butyl)-N-{[(pentanoyloxy)methoxy]carbonyl}glycine | MS (ESI) m/z 288; MS (ESI) m/z 577.1; HRMS: calcd for C13H23NO6 + H+, 290.15982; found (ESI+, [M + H]1+), 290.15951; |
| 72 | N-(tert-butyl)-N-({[(cyclobutylcarbonyl)oxy]methoxy}carbonyl)glycine | MS (ESI) m/z 288.1; MS (ESI) m/z 310.1; HRMS: calcd for C13H21NO6 + H+, 288.14416; found (ESI+, [M + H]1+), 288.14435; |
| 73 | N-(tert-butyl)-N-({[(3-cyclohexylpropanoyl)oxy]methoxy}carbonyl)glycine | MS (ESI) m/z 344.2; MS (ESI) m/z 709.4; HRMS: calcd for C17H29NO6 + Na+, 366.18871; found (ESI+, [M + NA]1+), 366.18863; |
| 74 | N-(tert-butyl)-N-[({[(4-fluorophenoxy)acetyl]oxy}methoxy)carbonyl]glycine | MS (ESI) m/z 356.1; |
| 75 | N-(tert-butyl)-N-({[(cyclohexylacetyl)oxy]methoxy}carbonyl)glycine | MS (ESI) m/z 328; MS (ESI) m/z 657.1; |
| 76 | N-(tert-butyl)-N-({[(2,6-dimethylbenzoyl)oxy]methoxy}carbonyl)glycine | MS (ESI) m/z 338.2; |
| 77 | N-(tert-butyl)-N-({[(phenylacetyl)oxy]methoxy}carbonyl)glycine | MS (ESI) m/z 322.1; MS (ESI) m/z 645.2; HRMS: calcd for C16H21NO6 + H+, 324.14416; found (ESI+, [M + H]1+), 324.14351; |
| 78 | N-(tert-butyl)-N-({[(2,2-dimethylpropanoyl)oxy]methoxy}carbonyl)glycine | MS (ESI) m/z 288.1; MS (ESI) m/z 577.1; HRMS: calcd for C13H23NO6 + H+, 290.15982; found (ESI+, [M + H]1+), 290.15965; |

TABLE B-continued

| Ref. Cpd. No. | Name | Spectra |
|---|---|---|
| 79 | N-({[(1-benzofuran-2-ylcarbonyl)oxy]methoxy}carbonyl)-N-(tert-butyl)glycine | MS (ESI) m/z 350; MS (ESI) m/z 721; HRMS: calcd for C17H19NO7 + H+, 350.12343; found (ESI+, [M + H]1+), 350.12327; |
| 80 | N-(tert-butyl)-N-[({[(1-methyl-1H-pyrrol-2-yl)carbonyl]oxy}methoxy)carbonyl]glycine | MS (ESI) m/z 313; MS (ESI) m/z 647.1; |
| 81 | N-({[(1,1'-biphenyl-4-ylcarbonyl)oxy]methoxy}carbonyl)-N-(tert-butyl)glycine | MS (ESI) m/z 386.2; HRMS: calcd for C21H23NO6 + Na+, 408.14176; found (ESI+, [M + NA]1+), 408.14195; |
| 82 | N-(tert-butyl)-N-({[(4-methoxybenzoyl)oxy]methoxy}carbonyl)glycine | MS (ESI) m/z 338.1; MS (ESI) m/z 677.3; HRMS: calcd for C16H21NO7 + Na+, 362.12102; found (ESI+, [M + NA]1+), 362.12095; |
| 83 | N-(tert-butyl)-N-({[(1H-indol-2-ylcarbonyl)oxy]methoxy}carbonyl)glycine | MS (ESI) m/z 349.2; HRMS: calcd for C17H20N2O6 + Na+, 371.12136; found (ESI+, [M + NA]1+), 371.12148; |
| 84 | N-(tert-butyl)-N-({[(diphenylacetyl)oxy]methoxy}carbonyl)glycine | MS (ESI) m/z 298.2; |
| 85 | N-(tert-butyl)-N-{[(1-naphthoyloxy)methoxy]carbonyl}glycine | MS (ESI) m/z 358.2; MS (ESI) m/z 717.4; MS (ESI) m/z 1076.6; |
| 86 | N-(tert-butyl)-N-{[(2-naphthoyloxy)methoxy]carbonyl}glycine | MS (ESI) m/z 360.1; MS (ESI) m/z 472.1; |
| 87 | N-(tert-butyl)-N-[({[(1-methyl-1H-indol-3-yl)carbonyl]oxy}methoxy)carbonyl]glycine | MS (ESI) m/z 361.2; MS (ESI) m/z 1085.7; MS (ESI) m/z 723.5; HRMS: calcd for C18H22N2O6 + H+, 363.15506; found (ESI+, [M + H]1+), 363.15556; |
| 88 | N-(tert-butyl)-N-({[(quinolin-2-ylcarbonyl)oxy]methoxy}carbonyl)glycine | MS (ESI) m/z 359.2; MS (ESI) m/z 1079.7; MS (ESI) m/z 719.4; |

TABLE B-continued

| Ref. Cpd. No. | Name | Spectra |
|---|---|---|
| 89 | N-(tert-butyl)-N-({[(pyridin-3-ylcarbonyl)oxy]methoxy}carbonyl)glycine | MS (ESI) m/z 309.2; MS (ESI) m/z 929.5; MS (ESI) m/z 619.3; |
| 90 | N-(tert-butyl)-N-{[(isonicotinoyloxy)methoxy]carbonyl}glycine | MS (ESI) m/z 311.1; MS (ESI) m/z 333.1; |
| 91 | N-(tert-butyl)-N-({[(2,6-difluorobenzoyl)oxy]methoxy}carbonyl)glycine | MS (ESI) m/z 390.2; MS (ESI) m/z 689.3; |
| 92 | N-(tert-butyl)-N-({[(2-fluorobenzoyl)oxy]methoxy}carbonyl)glycine | MS (ESI) m/z 326.2; MS (ESI) m/z 980.6; MS (ESI) m/z 653.3; |
| 93 | N-(tert-butyl)-N-[({[2-(trifluoromethyl)benzoyl]oxy}methoxy)carbonyl]glycine | MS (ESI) m/z 422.1; MS (ESI) m/z 753; |
| 94 | N-(tert-butyl)-N-({[(4-pyrrolidin-1-ylbenzoyl)oxy]methoxy}carbonyl)glycine | MS (ESI) m/z 379.2; |
| 95 | N-({[(1,1'-biphenyl-2-ylcarbonyl)oxy]methoxy}carbonyl)-N-(tert-butyl)glycine | MS (ESI) m/z 384.3; MS (ESI) m/z 1154.7; MS (ESI) m/z 769.5; |
| 96 | N-(tert-butyl)-N-({[(mesitylcarbonyl)oxy]methoxy}carbonyl)glycine | MS (ESI) m/z 701.5; MS (ESI) m/z 386.2; MS (ESI) m/z 1052.8; |
| 97 | N-(tert-butyl)-N-({[(4-isopropoxybenzoyl)oxy]methoxy}carbonyl)glycine | MS (ESI) m/z 733.3; MS (ESI) m/z 1100.3; MS (ESI) m/z 412.2; HRMS: calcd for $C_{18}H_{25}NO_7 + H+$, 368.17038; found (ESI+, [M + H]1+), 368.17069; |
| 98 | N-(tert-butyl)-N-({[(3,4,5-trimethoxybenzoyl)oxy]methoxy}carbonyl)glycine | MS (ESI) m/z 398; MS (ESI) m/z 797.2; MS (ESI) m/z 1195.9; HRMS: calcd for $C_{18}H_{25}NO_9+H+$, 400.16021; found (ESI+, [M + H]1+), 400.1610 |

TABLE B-continued

| Ref. Cpd. No. | Name | Spectra |
|---|---|---|
| 99 | N-(tert-butyl)-N-({[(3,5-dimethoxybenzoyl)oxy]methoxy}carbonyl)glycine | MS (ESI) m/z 368.1; MS (ESI) m/z 737.1; MS (ESI) m/z 414; HRMS: calcd for C17H23NO8+H+, 370.14965; found (ESI+, [M + H]1+), 370.15016; |
| 100 | N-(tert-butyl)-N-[({[(2E)-3-phenylprop-2-enoyl]oxy}methoxy)carbonyl]glycine | MS (ESI) m/z 334.2; MS (ESI) m/z 669.4; MS (ESI) m/z 1004.6; HRMS: calcd for C17H21NO6 + Na+, 358.12611; found (ESI+, [M + NA]1+), 358.12763; |
| 101 | N-(tert-butyl)-N-[({[(3-methyl-1-benzofuran-2-yl)carbonyl]oxy}methoxy)carbonyl]glycine | MS (ESI) m/z 725.4; MS (ESI) m/z 1088.6; MS (ESI) m/z 398.2; HRMS: calcd for C18H21NO7 + H+, 364.13908; found (ESI, [M + H]1+), 364.13956; |
| 102 | N-{[({[3,5-bis(trifluoromethyl)phenyl]acetyl}oxy)methoxy]carbonyl}-N-(tert-butyl)glycine | MS (ESI) m/z 458.1; MS (ESI) m/z 917.1; HRMS: calcd for C18H19F6NO6 + H+, 460.11893; found (ESI+, [M + H]1+), 460.11854; |
| 103 | N-(tert-butyl)-N-[({[4-(heptyloxy)benzoyl]oxy}methoxy)carbonyl]glycine | MS (ESI) m/z 422.2; MS (ESI) m/z 468.3; MS (ESI) m/z 845.3; HRMS: calcd for C22H33NO7 + H+, 424.23298; found (ESI+, [M + H]1+), 424.23295; |
| 104 | N-(tert-butyl)-N-[({[2-(2-phenylethyl)benzoyl]oxy}methoxy)carbonyl]glycine | MS (ESI+) m/z 414.19088; MS (ESI+) m/z 414.19112; HRMS: calcd for C23H27NO6 + H+, 414.19112; found (ESI+, [M + H]1+), 414.19088; |

TABLE B-continued

| Ref. Cpd. No. | Name | Spectra |
|---|---|---|
| 105 | N-(tert-butyl)-N-[({[4-(dodecyloxy)benzoyl]oxy}methoxy)carbonyl]glycine | MS (ESI+) m/z 494.31095; MS (ESI+) m/z 494.31123; HRMS: calcd for C27H43NO7 + H+, 494.31123; found (ESI+, [M + H]1+), 494.31095; |
| 106 | N-[({[4-(acetylamino)benzoyl]oxy}methoxy)carbonyl]-N-(tert-butyl)glycine | MS (ESI) m/z 367.1; MS (ESI) m/z 733.1; |
| 107 | N-({[(9-anthrylcarbonyl)oxy]methoxy}carbonyl)-N-(tert-butyl)glycine | MS (ESI) m/z 408.3; MS (ESI) m/z 1226.7; MS (ESI) m/z 817.5; |
| 108 | N-({[(4-benzoylbenzoyl)oxy]methoxy}carbonyl)-N-(tert-butyl)glycine | MS (ESI) m/z 414.2; |

Reference Compound 109

3,3-Dimethyl-butyric acid [tert-butyl-(2-isobutoxy-carbonyloxy-2-oxo-ethyl)-carbamoyloxy)-methyl ester

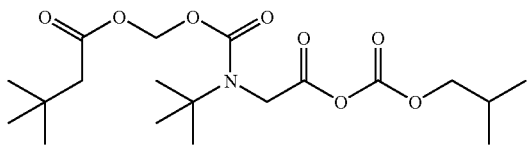

To a solution of Reference Compound 56 in dichloromethane at room temperature is added 1.2 equivalent of [1,8-bis(dimethylamino)naphthalene, N,N,N',N'-tetramethyl-1,8-naphthalenediamine] and 0.95 equivalent of isobutylchloroformate. The reaction is stirred for 24 hour, diluted with dichloromethane, washed with dilute HCl, brine, then water. It is dried with sodium sulfate. Solvent removed and the product is used in the next step without further purification.

Reference Compound 110

3,3-Dimethylbutyric acid ethylsulfanylcarbonyloxymethyl ester

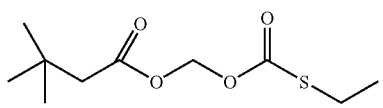

To a solution of t-butylacetic acid (0.025 mol, 3 g) in methanol is added tetrabutylammonium hydroxide (1M/methanol, 25 ml). The mixture is stirred for 1 h and the solvent removed to a residue. The residue is dissolved in 150 ml of methylene chloride and 150 ml of water and a solution of O-chloromethyl S-ethyl carbonothioate (0.025 mol, 3.85 f) in 50 ml of methylene chloride added. The mixture is stirred at room temperature for 24 h. The methylene chloride layer is separated, washed with water, brine and dried over sodium sulfate. The solvent is removed under vacuo and the residue stirred in 300 ml of ether for 24 h. The resulting white solid is filtered, the solid discarded and the solvent removed from the filtrate to give 6 g of a crude oil.

Reference Compound 111

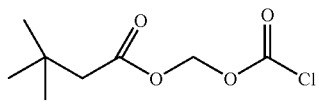

To a stirred solution of 3,3-dimethylbutyric acid ethylsulfanylcarbonyloxymethyl ester (Reference Compound 110) (0.025 ml, 6 g) in methylene chloride at −20° C. (dry ice/carbon tetrachloride) is added sulfuryl chloride 0.025 mol, 3.5 g). After 10 min, 0.1 ml of boron trifluoride etherate is added. The mixture is stirred at 0° C. for 1 h, at room temperature for 30 min. The volatiles are removed by distillation to yield 4.9 g of the desired acid chloride.

Following the procedure of Reference Compound 111 the corresponding acid chloride used in Examples 112 to 120 was prepared.

Reference Compound 112 benzyl N-(butoxycarbonyl)-N-(tert-butyl)glycinate

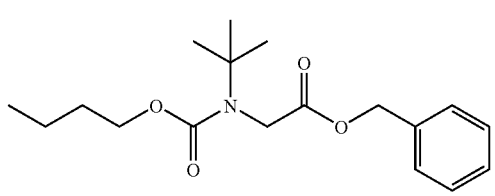

Reference Compound 113 benzyl N-(tert-butyl)-N-(isobutoxycarbonyl)glycinate

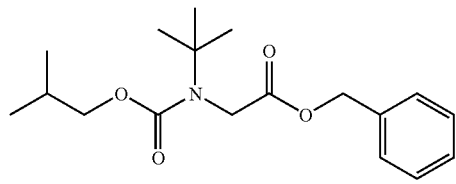

Reference Compound 114 benzyl N-(tert-butyl)-N-(methoxycarbonyl)glycinate

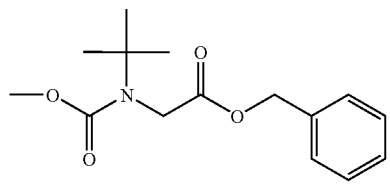

Reference Compound 115

N-(butoxycarbonyl)-N-(tert-butyl)glycine

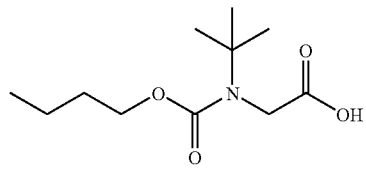

Reference Compound 116

N-(tert-butyl)-N-(isobutoxycarbonyl)glycine

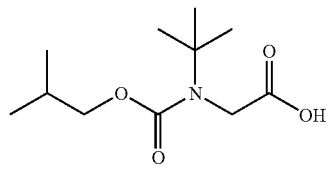

Reference Compound 117

N-(tert-butyl)-N-(methoxycarbonyl)glycine

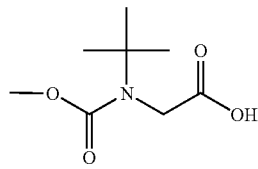

Reference Compound 118 isobutoxycarbonyl N-(butoxycarbonyl)-N-(tert-butyl)glycinate

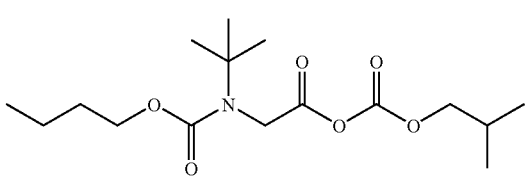

Reference Compound 119 isobutoxycarbonyl N-(tert-butyl)-N-(isobutoxycarbonyl)glycinate

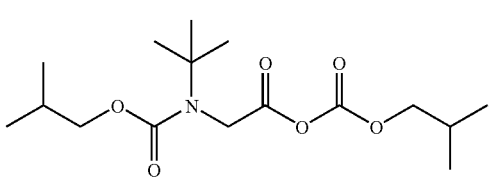

Reference Compound 120 isobutoxycarbonyl N-(tert-butyl)-N-(methoxycarbonyl)glycinate

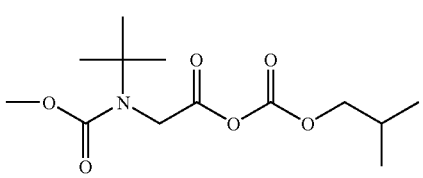

Reference Compound 121

(5-methyl-2-oxo-1,3-dioxol-4-yl)methyl 4-nitrophenyl carbonate

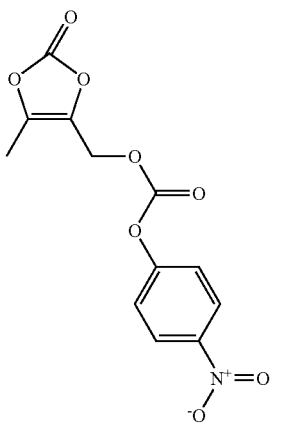

The product of the Reference Example was prepared using the conditions described by R. Sakamoto et al, Chem. Pharm. Bull. 32(6), 2241-2248 (1984).

Reference Compound 122

4-nitrophenyl (2-oxo-5-phenyl-1,3-dioxol-4-yl)methyl carbonate

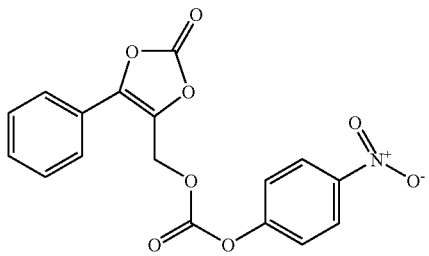

The product of the Reference Example was prepared using the conditions described by R. Sakamoto et al, Chem. Pharm. Bull. 32(6), 2241-2248 (1984).

Reference Compound 123

[5-(4-methoxyphenyl)-2-oxo-1,3-dioxol-4-yl]methyl 4-nitrophenyl carbonate

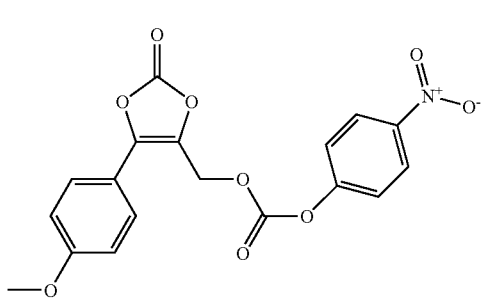

The product of the Reference Example was prepared using the conditions described by R. Sakamoto et al, Chem. Pharm. Bull. 32(6), 2241-2248 (1984).

Reference Compound 124

4-tert-butyl-10,10-dimethyl-3,6-dioxo-2,7-dioxa-4-aza-10-silaundec-1-yl (2E)-3-phenylacrylate

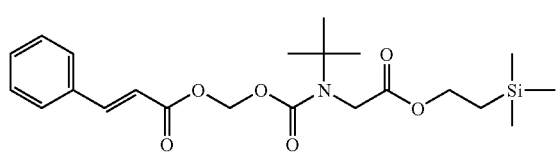

Trans-cinnamic acid (23.1 mmol) and 1.0 M tetrabutylammonium hydroxide (22.2 mmol) in methanol are stirred for one hour, and the methanol is removed. THF is added. To this solution is added 2-(trimethylsilyl)ethyl 2-(tert-butyl((chloromethoxy)carbonyl)amino)-acetate (18.5 mmol) and the mixture is stirred at room temperature for 24 hr. The solvent is removed and the residue is diluted with ether. The resulting solution is washed with water and brine. The organic layer is dried over magnesium sulfate, filtered and concentrated under reduced pressure to yield 5.01 g (61%) MS (ESI) m/z 436.3.

Using substantially the same procedure as described above for Reference Compound 124 the following reference compounds were prepared from the appropriate carboxylic acids:

Reference Compound 125

4-tert-butyl-10,10-dimethyl-3,6-dioxo-2,7-dioxa-4-aza-10-silaundec-1-yl anthracene-9-carboxylate

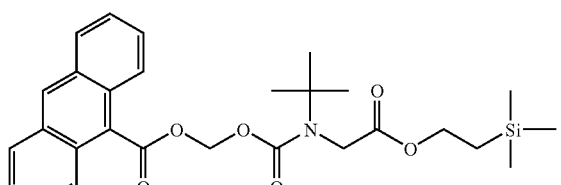

MS (ESI) m/z 510.3

Reference Compound 126

4-tert-butyl-10,10-dimethyl-3,6-dioxo-2,7-dioxa-4-aza-10-silaundecyl 4-benzoylbenzoate MS (ESI) m/z 536.2

Example 1

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 2-methylpropanoate

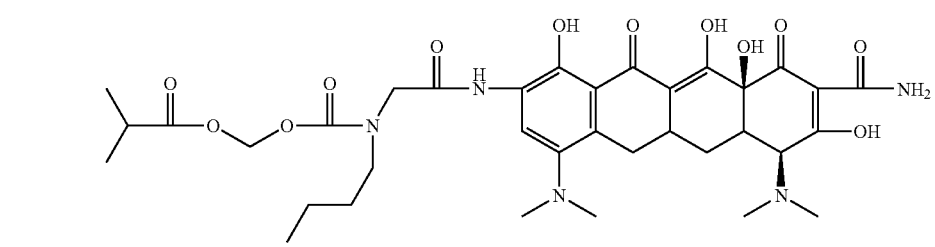

To a solution of n-Butylglycylcycline in acetonitrile/DMPA (1:5), sodium carbonate is added. The reaction mixture is stirred for 5 min and propanoic acid, 2-methyl-[(chlorocarbonyl)oxy]methyl ester prepared according to the methods described in M. Folkmann and F. J. Lund, Synthesis, December 1990, 1159-1166, is added. Stirring is continued for about 30 to 45 minute (or monitored by MS (ES)). Upon completion of the reaction, 0.5 mL of methanol is added and the mixture poured slowly into a mixture of isopropanol and ether. 1.0M HCl in ether is added and the solid is filtered. The solid is dissolved in water and is extracted with methylene chloride to give the product of the Example.

MS (ESI) m/z 730.28 (M+H);

Following the procedure of Example 1, and the corresponding acid chloride prepared by methods described in M. Folkmann and F. J. Lund, Synthesis, December 1990, 1159-1166 and N-butylglycylcycline or N-propylglycylcycline the following Examples 2-41 are prepared.

Example 2

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methoxybenzoate

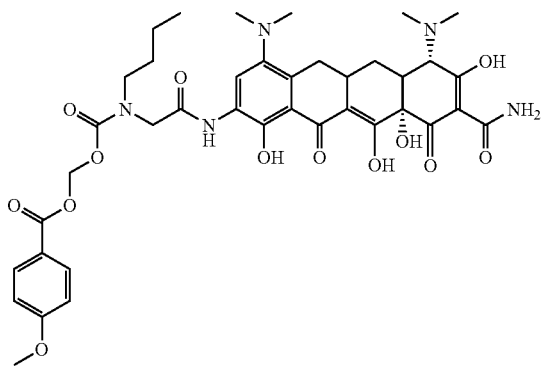

The title compound is prepared by the procedure of Example 1, using [(chlorocarbonyl)oxy]methyl 4-methoxybenzoate and N-butylglycylcycline to give the product of the Example.

Example 3

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methylbenzoate

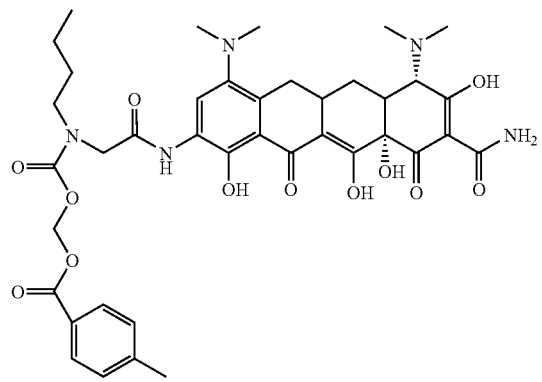

The title compound is prepared by the procedure of Example 1, using [(chlorocarbonyl)oxy]methyl 4-methylbenzoate and N-butylglycylcycline to give the product of the Example.

MS (ESI) m/z 778.3 ((M+H)+);

Example 4

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-fluorobenzoate

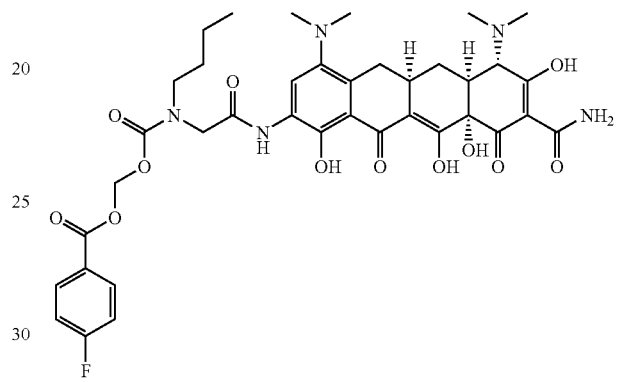

The title compound is prepared by the procedure of Example 1, using [(chlorocarbonyl)oxy]methyl 4-fluorobenzoate and N-butylglycylcycline to give the product of the Example.

MS (ESI) m/z 782.3 ((M+H)+);

Example 5

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methylbenzoate

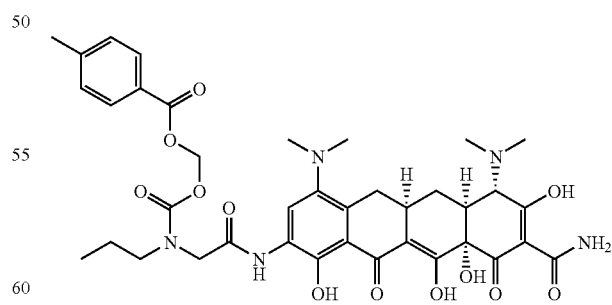

The title compound is prepared by the procedure of Example 1, using [(chlorocarbonyl)oxy]methyl 4-methylbenzoate and N-propylglycylcycline to give the product of the Example.

MS (ESI) m/z 764.3 ((M+H)+);

Example 6

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methoxybenzoate

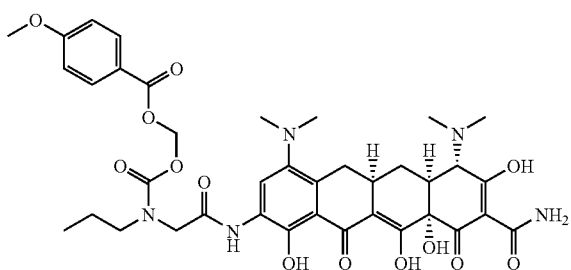

The title compound is prepared by the procedure of Example 1, using [(chlorocarbonyl)oxy]methyl 4-methoxybenzoate and N-propylglycylcycline to give the product of the Example.
MS (ESI) m/z 780.3 ((M+H)+);

Example 7

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclobutanecarboxylate

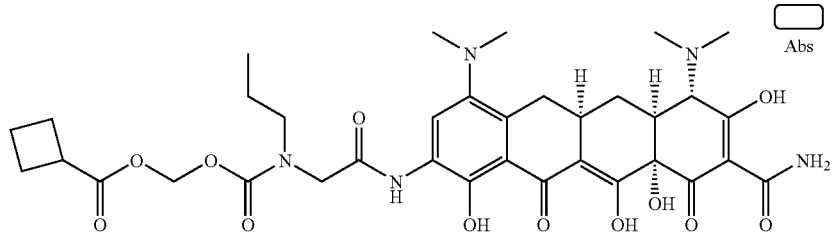

The title compound is prepared by the procedure of Example 1, using [(chlorocarbonyl)oxy]methyl cyclobutanecarboxylate and N-propylglycylcycline to give the product of the Example.
MS (ESI) m/z 728.3 ((M+H)+);

Example 8

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-fluorobenzoate

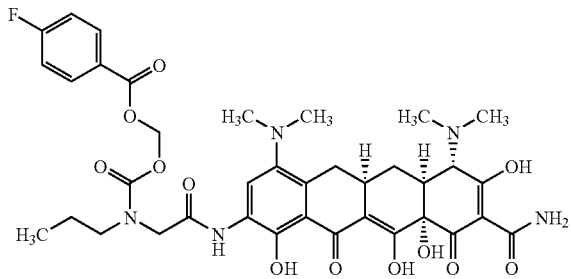

The title compound is prepared by the procedure of Example 1, using [(chlorocarbonyl)oxy]methyl 4-fluorobenzoate and N-propylglycylcycline to give the product of the Example.
MS (ESI) m/z 768.3 ((M+H)+);

Example 9

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl pivalate

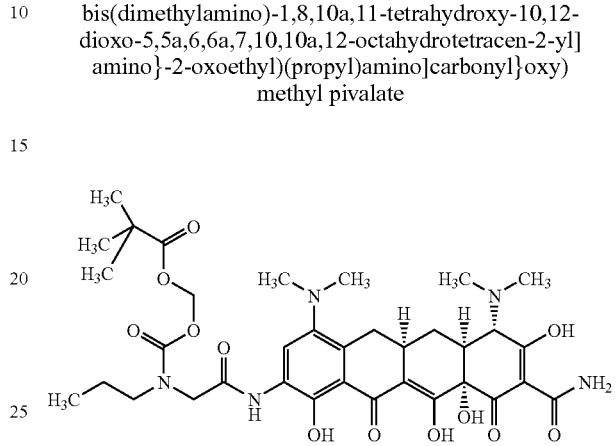

The title compound is prepared by the procedure of Example 1, using Propanoic acid, 2,2-dimethyl-, [(chlorocarbonyl)oxy]methyl ester and N-propylglycylcycline to give the product of the Example.
MS (ESI) m/z 730.3 ((M+H)+);

Example 10

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-methylpropanoate

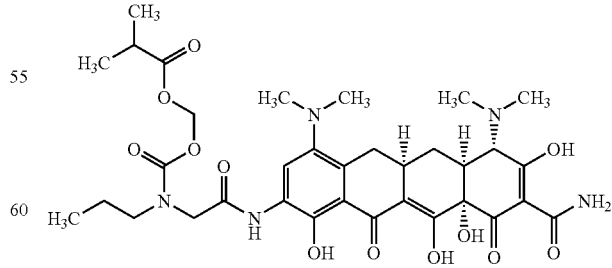

The title compound is prepared by the procedure of Example 1, using propanoic acid, 2-methyl-, [(chlorocarbonyl)oxy]methyl ester and N-propylglycylcycline to give the product of the Example.
MS (ESI) m/z 716.3 ((M+H)+);

Example 11

({[(2-{[(5aR,6aS,7S,10aS)-9-(aminocarbonyl)-4,7-bis(dimethylamino)-1,8,10a,11'-tetrahydroxy-10,12-dioxo-5,5a,6,6a,7,10,10a,12-octahydrotetracen-2-yl]amino}-2-oxoethyl)(propyl)amino]carbonyl}oxy)methyl phenylacetate

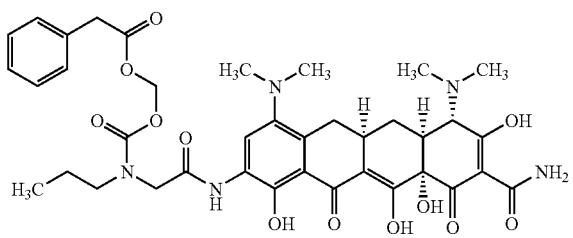

The title compound is prepared by the procedure of Example 1, using benzeneacetic acid, [(chlorocarbonyl)oxy]methyl ester and N-propylglycylcycline to give the product of the Example.

MS (ESI) m/z 764.3 ((M+H)+);

Example 12

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl phenylacetate

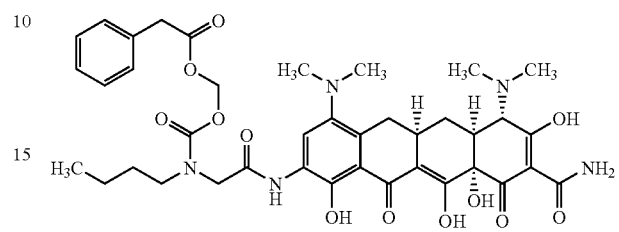

The title compound is prepared by the procedure of Example 1, using benzeneacetic acid, [(chlorocarbonyl)oxy]methyl ester and N-butylglycylcycline to give the product of the Example.

MS (ESI) m/z 778.3 ((M+H)+);

Example 13

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl pivalate

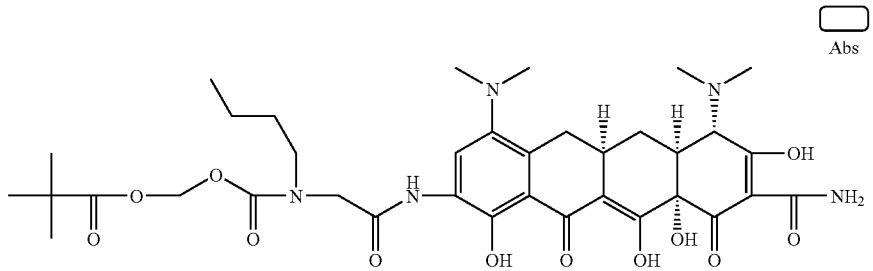

The title compound is prepared by the procedure of Example 1, using propanoic acid, 2,2-dimethyl-, [(chlorocarbonyl)oxy]methyl ester and N-butylglycylcycline to give the product of the Example.

MS (ESI) m/z 744.3 ((M+H)+);

Example 14 benzyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate

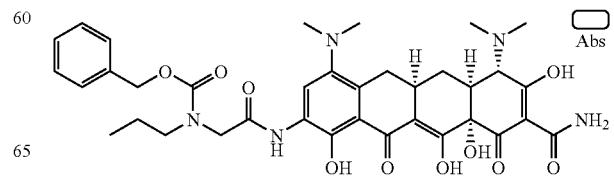

The title compound is prepared by the procedure of Example 1, using benzyl chloroformate and N-propylglycylcycline in the presence of sodium carbonate and DMPU in acetonitrile to give the product of the Example.

MS (ESI) m/z 706.3 ((M+H)+);
HRMS: calcd for $C_{36}H_{43}N_5O_{10} \cdot HCl$, 741.2777. found (ESI), 706.31133;

Example 15 ethyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate

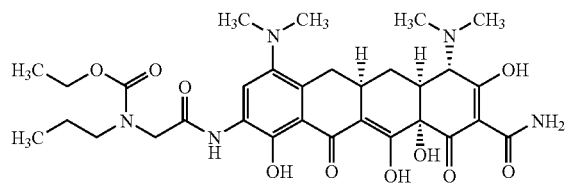

The title compound is prepared by the procedure of Example 1, using ethyl chloroformate and N-propylglycylcycline in the presence of sodium carbonate and DMPU in acetonitrile to give the product of the Example.

MS (ESI) m/z 644.3 ((M+H)+);
HRMS: calcd for $C_{31}H_{41}N_5O_{10} \cdot HCl$, 679.2620. found (ESI+), 644.29398;

Example 16 isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate

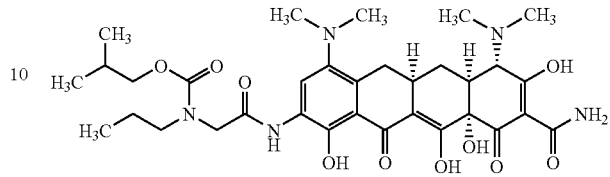

The title compound is prepared by the procedure of Example 1, using isobutyl chloroformate and N-propylglycylcycline in the presence of sodium carbonate and DMPU in acetonitrile to give the product of the Example.

MS (ESI) m/z 672.3 ((M+H)+);
MS (ESI) m/z 336.9 ((M+2H)2+);
HRMS: calcd for $C_{33}H_{45}N_5O_{10} \cdot HCl$, 707.2933. found (ESI+), 672.32618;

Example 17

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy) methyl heptanoate

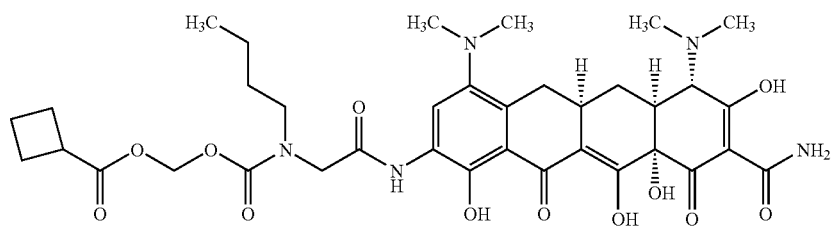

The title compound is prepared by the procedure of Example 1, using heptanoic acid, [(chlorocarbonyl)oxy]methyl ester and N-butylglycylcycline to give the product of the Example.

MS (ESI+) m/z 772.2 (M+H);
HRMS: calcd for $C_{38}H_{53}N_5O_{12} \cdot 2.00HCl$, 843.3224. found (ESI+), 772.37696;

Example 18

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy) methyl cyclobutanecarboxylate

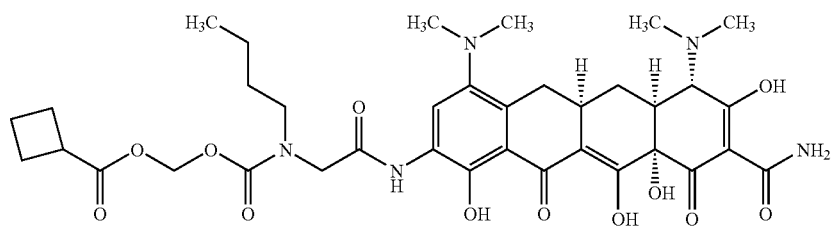

The title compound is prepared by the procedure of Example 1, using [(chlorocarbonyl)oxy]methyl cyclobutanecarboxylate and N-butylglycylcycline to give the product of the Example.

MS (ESI) m/z 742.3 ((M+H)+);

HRMS: calcd for $C_{36}H_{47}N_5O_{12}\cdot 2.00HCl$, 813.2755. found (ESI+), 742.32898;

Example 19

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl heptanoate

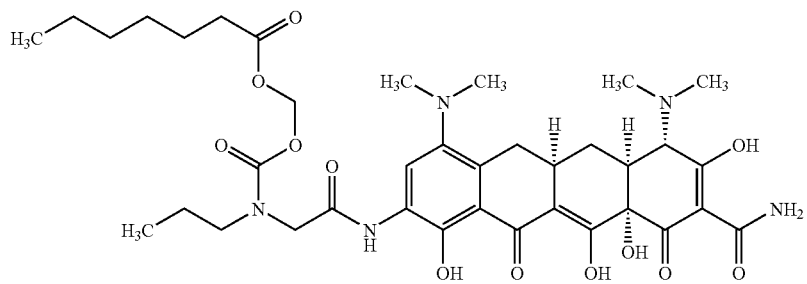

The title compound is prepared by the procedure of Example 1, using Heptanoic acid, [(chlorocarbonyl)oxy]methyl ester and N-propylglycylcycline to give the product of the Example.

MS (ESI) m/z 758.4 ((M+H)+);

HRMS: calcd for $C_{37}H_{51}N_5O_{12}\cdot HCl$, 793.3301. found (ESI+), 758.36175;

Example 20

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-tert-butylbenzoate

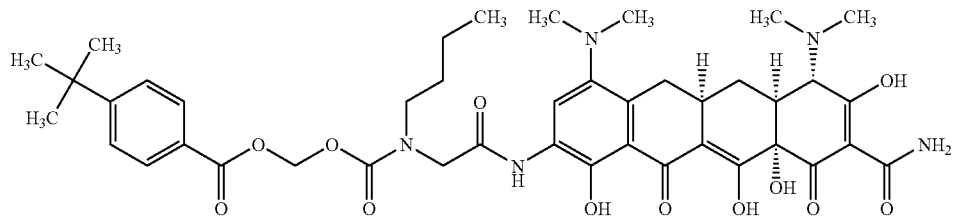

The title compound is prepared by the procedure of Example 1, using [(chlorocarbonyl)oxy]methyl 4-tert-butylbenzoate and N-butylglycylcycline to give the product of the Example.

MS (ESI+) m/z 820.2 (M+H);

HRMS: calcd for $C_{42}H_{53}N_5O_{12}\cdot HCl$, 855.3458. found (ESI+), 820.37684;

Example 21

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 1,1'-biphenyl-4-carboxylate

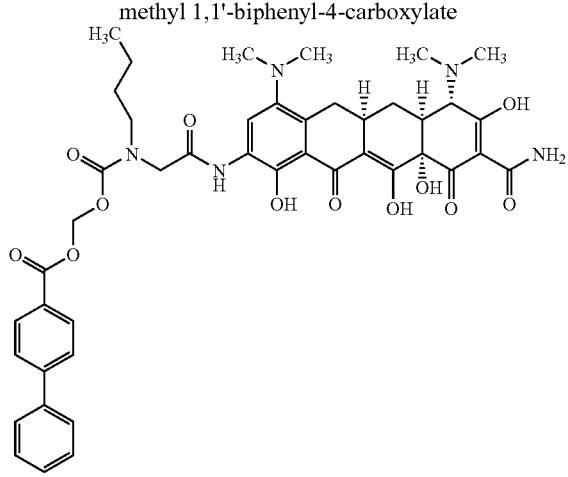

The title compound is prepared by the procedure of Example 1, using [(chlorocarbonyl)oxy]methyl biphenyl-4-carboxylate and N-butylglycylcycline to give the product of the Example.

MS (ESI) m/z 840.3 ((M+H)+);

HRMS: calcd for $C_{44}H_{49}N_5O_{12}$·HCl, 875.3145. found (ESI+), 840.34337;

Example 22

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 3,5-dimethylbenzoate

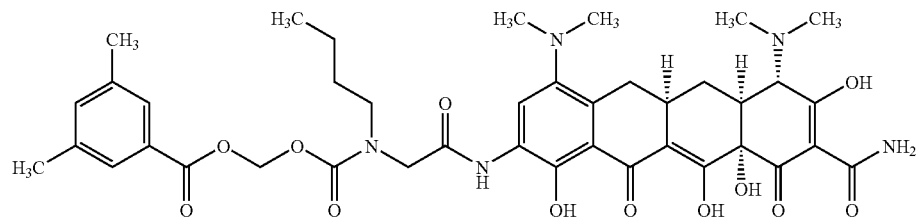

The title compound is prepared by the procedure of Example 1, using [(chlorocarbonyl)oxy]methyl 3,5-dimethylbenzoate and N-butylglycylcycline to give the product of the Example.
MS (ESI) m/z 792.3 ((M+H)+);
HRMS: calcd for $C_{40}H_{49}N_5O_{12}$·2.00HCl, 863.2911. found (ESI+), 792.34378;

Example 23

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-2-carboxylate

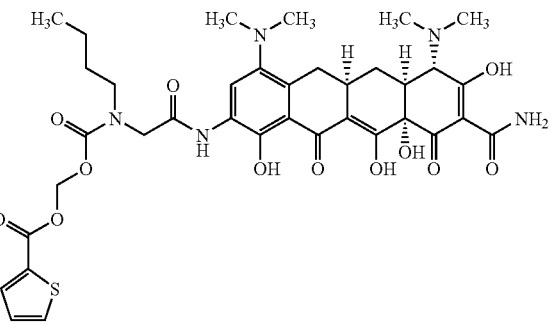

The title compound is prepared by the procedure of Example 1, using [(chlorocarbonyl)oxy]methyl thiophene-2-carboxylate and N-butylglycylcyclme to give the product of the Example.
MS (ESI) m/Z 770.1 ((M+H)+);
HRMS: calcd for $C_{36}H_{43}N_5O_{12}S$·HCl, 805.2396. found (ESI+), 770.27084;

Example 24

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 1,1'-biphenyl-4-carboxylate

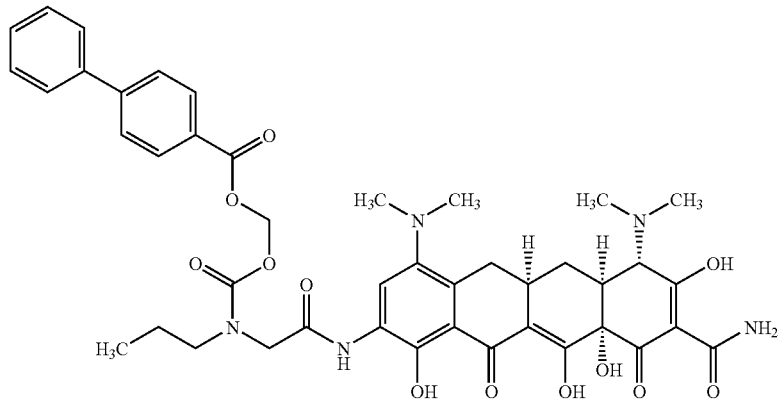

The title compound is prepared by the procedure of Example 1, using [(chlorocarbonyl)oxy]methyl biphenyl-4-carboxylate and N-propylglycylcycline to give the product of the Example.

MS (ESI) m/z 826.4 ((M+H)+);
MS (ESI) m/z 414 ((M+2H)$_2$+);
HRMS: calcd for $C_{43}H_{47}N_5O_{12}$·HCl, 861.2988. found (ESI+), 826.32782;

Example 25

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-2-carboxylate

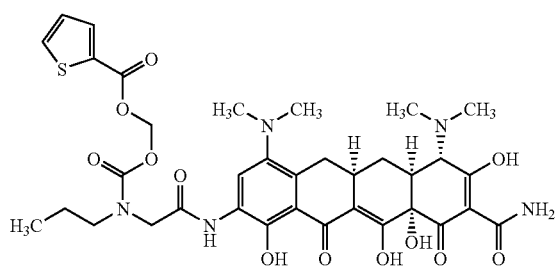

The title compound is prepared by the procedure of Example 1, using [(chlorocarbonyl)oxy]methyl thiophene-2-carboxylate and N-propylglycylcycline to give the product of the Example.

MS (ESI) m/z 756.3 ((M+H)+);
MS (ESI) m/z 378.9 ((M+2H)$_2$+);
HRMS: calcd for $C_{35}H_{41}N_5O_{12}S$·HCl, 791.2239. found (ESI+), 756.2532;

Example 26

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 3,5-dimethylbenzoate The title compound is prepared by the procedure of Example 1, using [(chlorocarbonyl)oxy]methyl 3,5-dimethylbenzoate and N-propylglycylcycline to give the product of the Example.

MS (ESI) m/z 778.3 ((M+H)+);
HRMS: calcd for $C_{39}H_{47}N_5O_{12}$·HCl, 813.2988. found (ESI+), 778.32984;

Example 27

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-3-carboxylate

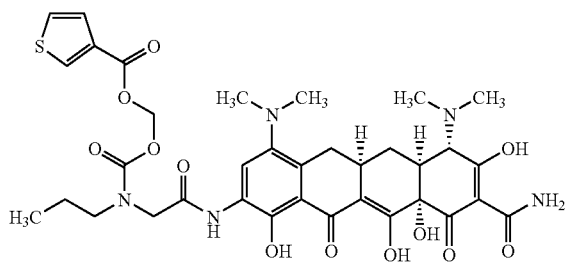

The title compound is prepared by the procedure of Example 1, using [(chlorocarbonyl)oxy]methyl thiophene-3-carboxylate and N-propylglycylcycline to give the product of the Example.

MS (ESI) m/z 756.3 ((M+H)+);

HRMS: calcd for $C_{35}H_{41}N_5O_{12}S \cdot HCl$, 791.2239. found (ESI+), 756.2547;

Example 28

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-tert-butylbenzoate

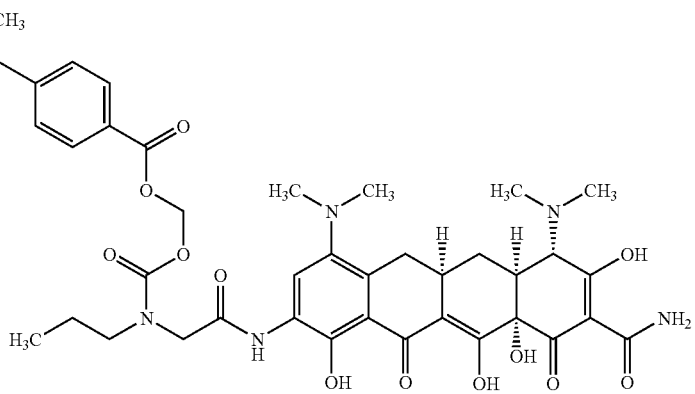

The title compound is prepared by the procedure of Example 1, using [(chlorocarbonyl)oxy]methyl 4-tert-butylbenzoate and N-propylglycylcycline to give the product of the Example.

MS (ESI) m/z 806.4 ((M+H)+);
MS (ESI) m/z 403.9 ((M+2H)$_2$+);
HRMS: calcd for $C_{41}H_{51}N_5O_{12} \cdot HCl$, 841.3301. found (ESI+), 806.36024;

Example 29

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-3-carboxylate

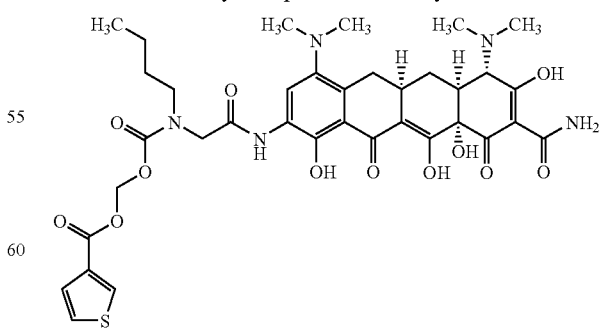

The title compound is prepared by the procedure of Example 1, using [(chlorocarbonyl)oxy]methyl thiophene-3-carboxylate and N-butylglycylcycline to give the product of the Example.

MS (ESI) m/z 770.3 ((M+H)+);

HRMS: calcd for $C_{36}H_{43}N_5O_{12}S \cdot HCl$, 805.2396. found (ESI+), 770.27028;

Example 30

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 2-furoate

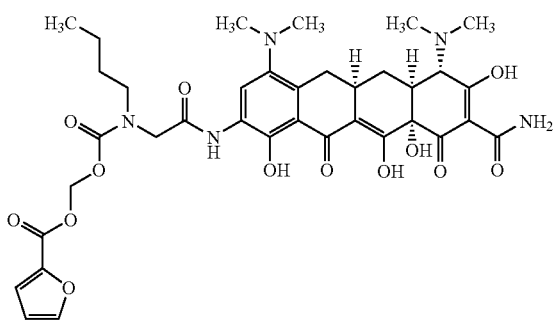

The title compound is prepared by the procedure of Example 1, using [(chlorocarbonyl)oxy]methyl 2-furoate and N-butylglycylcycline to give the product of the Example.

MS (ESI) m/z 752.2 ((M−H)−);

HRMS: calcd for $C_{36}H_{43}N_5O_{13} \cdot HCl$, 789.2624. found (ESI+), 754.29242;

Example 31

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-furoate

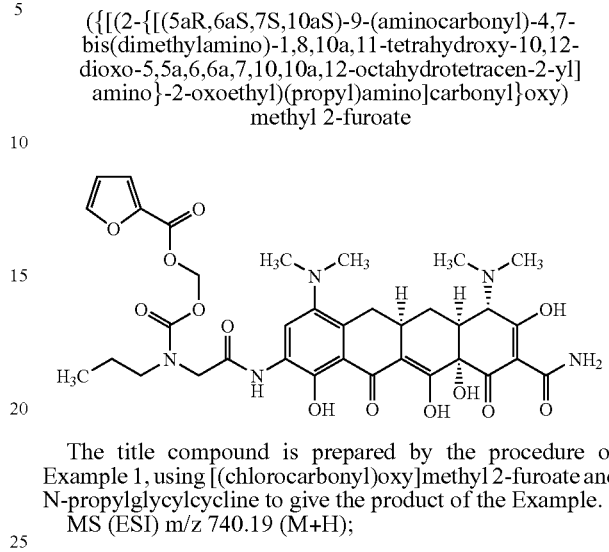

The title compound is prepared by the procedure of Example 1, using [(chlorocarbonyl)oxy]methyl 2-furoate and N-propylglycylcycline to give the product of the Example.

MS (ESI) m/z 740.19 (M+H);

Example 32

1-({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)ethyl acetate

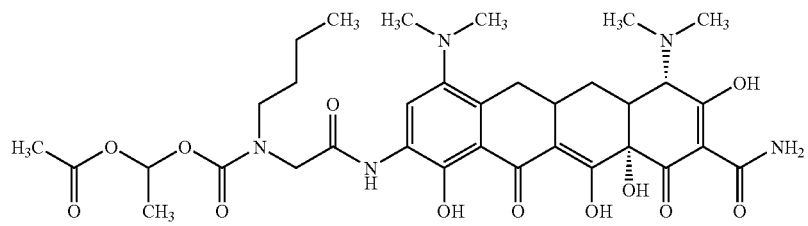

The title compound is prepared by the procedure of Example 1, using 1-[(chlorocarbonyl)oxy]ethyl acetate and N-butylglycylcycline to give the product of the Example.

MS (ESI) m/z 716.14 (M+H);

HRMS: calcd for $C_{34}H_{45}N_5O_{12}$, 715.3065. found (ESI+), 716.31469;

Example 33

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclohexanecarboxylate

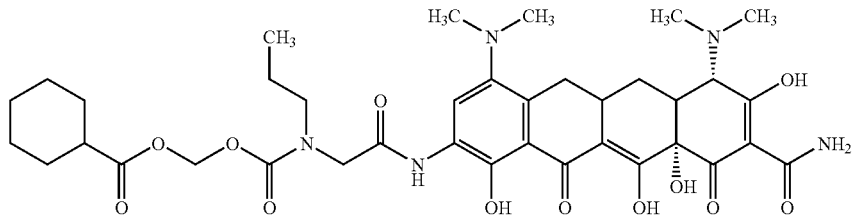

The title compound is prepared by the procedure of Example 1, using cyclohexanecarboxylic acid, [(chlorocarbonyl)oxy]methyl ester d N-propylglycylcycline to give the product of the Example.

MS (ESI) m/z 756.08 (M+H);

HRMS: calcd for $C_{37}H_{49}N_5O_{12}$, 755.3378. found (ESI+), 756.34507;

Example 34

({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl cyclohexanecarboxylate

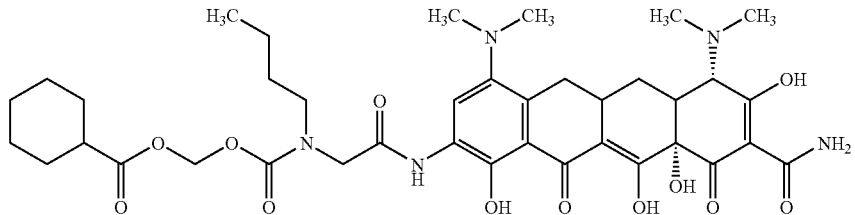

The title compound is prepared by the procedure of Example 1, using cyclohexanecarboxylic acid, [(chlorocarbonyl)oxy]methyl ester and N-butylglycylcycline to give the product of the Example.

MS (ESI) m/z 70.64 (M+H);

HRMS: calcd for $C_{38}H_{51}N_5O_{12}\cdot HCl$, 805.3301. found (ESI+), 770.36093;

Example 35

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 3,3-dimethylbutanoate

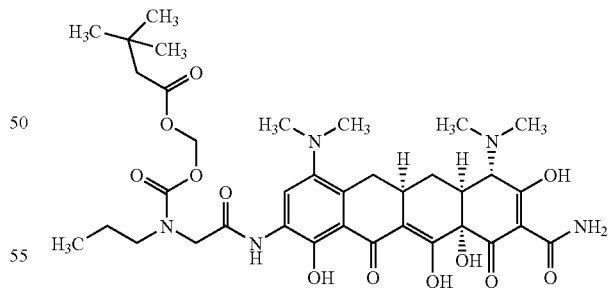

The title compound is prepared by the procedure of Example 1, using butanoic acid, 3,3-dimethyl-, [(chlorocarbonyl)oxy]methyl ester and N-propylglycylcycline to give the product of the Example.

MS m/z 00-304761LMS;

HRMS: calcd for $C_{36}H_{49}N_5O_{12}\cdot HCl$, 779.3145. found (ESI+), 744.34539;

Example 36

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy) methyl 3,3-dimethylbutanoate

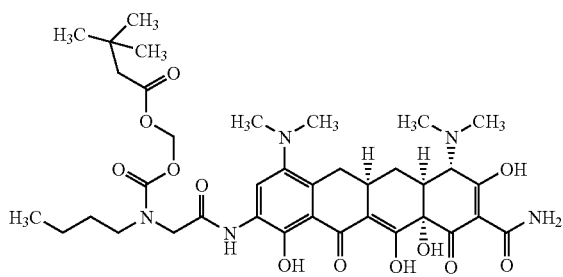

The title compound is prepared by the procedure of Example 1, using Butanoic acid, 3,3-dimethyl-, [(chlorocarbonyl)oxy]methyl ester and N-butylglycylcycline to give the product of the Example.

MS m/z 00-304762LMS;

HRMS: calcd for $C_{37}H_{51}N_5O_{12}$·HCl, 793.3301. found (ESI+), 758.36071;

Example 37

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy) methyl 2,2-dimethylbutanoate

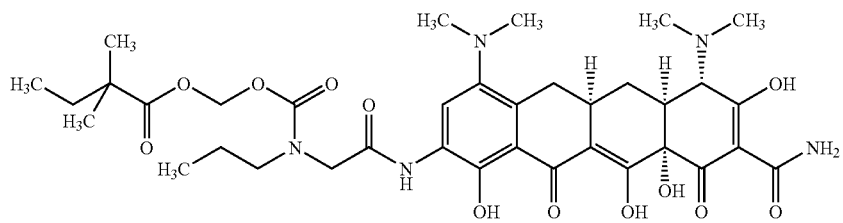

The title compound is prepared by the procedure of Example 1, using [(chlorocarbonyl)oxy]methyl 2,2-dimethylbutanoate and N-propylglycylcycline to give the product of the Example.

MS m/z 00-304763LMS;

HRMS: calcd for $C_{36}H_{49}N_5O_{12}$·HCl, 779.3145. found (ESI+), 744.3452;

Example 38

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy) methyl cyclopentylacetate

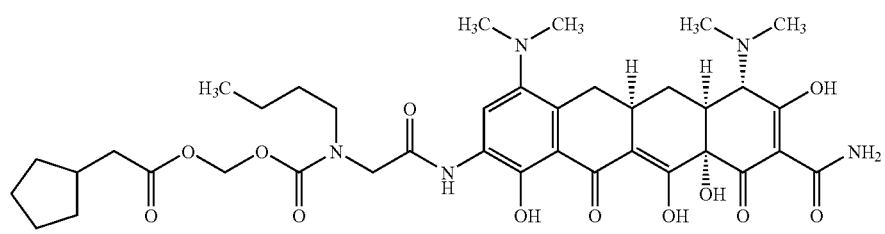

The title compound is prepared by the procedure of Example 1, using [(chlorocarbonyl)oxy]methyl cyclopentylacetate and N-butylglycylcycline to give the product of the Example.

MS (ESI) m/z 770.7 (M+H);

HRMS: calcd for $C_{38}H_{51}N_5O_{12}$·HCl, 805.3301. found (ESI+), 770.36062;

Example 39

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl adamantane-1-carboxylate

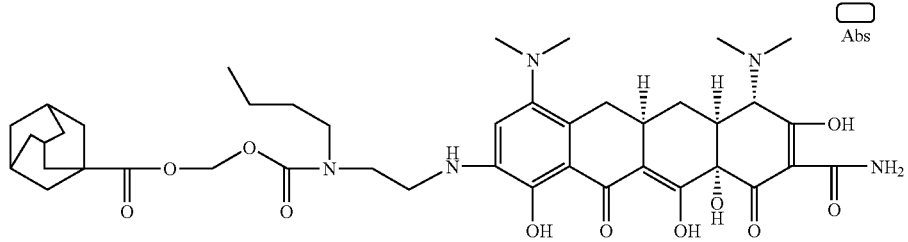

The title compound is prepared by the procedure of Example 1, using [(chlorocarbonyl)oxy]methyl adamantane-1-carboxylate and N-butylglycylcycline to give the product of the Example.
MS (ESI) m/z 822.9 (M+H);
HRMS: calcd for $C_{42}H_{55}N_5O_{12}$·HCl, 857.3614. found (ESI+), 822.39184;

Example 40

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclopentylacetate

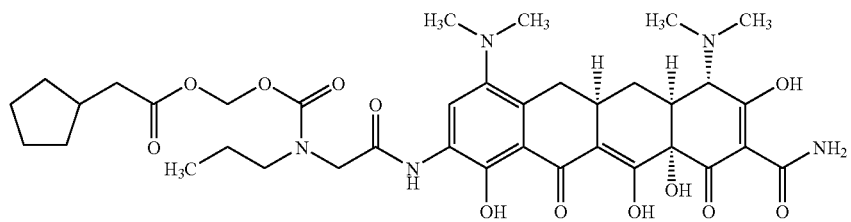

The title compound is prepared by the procedure of Example 1, using [(chlorocarbonyl)oxy]methyl cyclopentylacetate and N-propylglycylcycline to give the product of the Example.
MS (ESI) m/z 754.2 ((M−H)−);
HRMS: calcd for $C_{37}H_{49}N_5O_{12}$·HCl, 791.3145. found (ESI+), 756.34433;

Example 41

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl adamantane-1-carboxylate

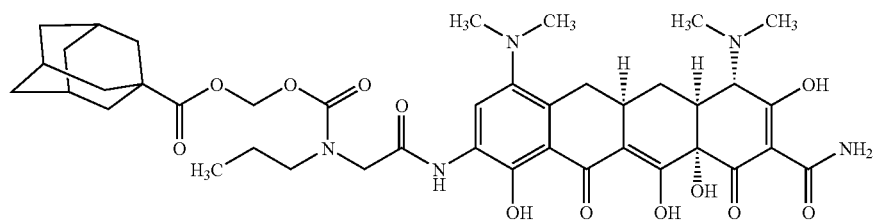

The title compound is prepared by the procedure of Example 1, using [(chlorocarbonyl)oxy]methyl adamantane-1-carboxylate and N-propylglycylcycline to give the product of the Example.

MS (ESI) m/z 808.8 (M+H);

HRMS: calcd for $C_{41}H_{53}N_5O_{12}$·HCl, 843.3458. found (ESI+), 808.37604;

Example 42

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,3-dimethylbutanoate

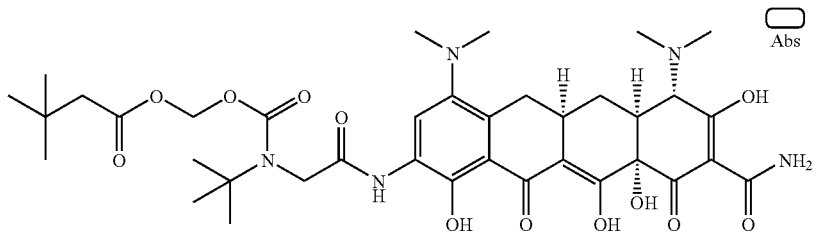

To a solution of 9-amino-minocycline monosulfate (0.0055 mol, 3.135 g, 1 equivalent) in a mixture of 12 ml of acetonitrile and 50 ml of DMPU is added 1.66 g (3 equivalents) of triethylamine and Reference Compound 109 (0.012 mole, 4.88 g), 3,3-Dimethyl-butyric acid [tert-butyl-(2-isobutoxycarbonyloxy-2-oxo-ethyl)-carbamoyloxy)-methyl ester. The reaction is stirred at room temperature for 2 hour, 1 mL methanol is added, stirred for 5 min. and the mixture is poured onto a mixture of 500 ml of ether and 100 ml of isopropanol. Solid is collected and purified by extraction to give 1.5 g of the product of the Example.

MS (ESI) m/z 758.55 (M+H);

HRMS: calcd for $C_{37}H_{51}N_5O_{12}$·HCl, 793.3301. found (ESI+), 758.36201;

Example 43

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-tert-butylbenzoate

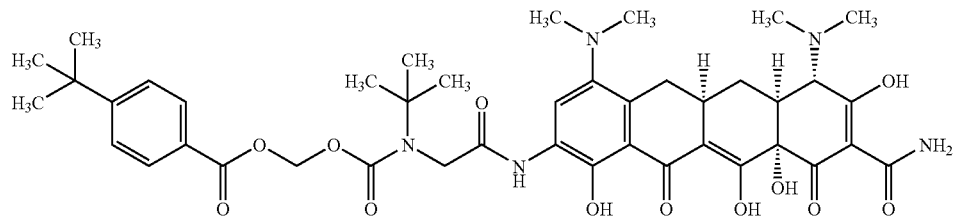

Reference Compound 57 is reacted under the conditions of Reference Compound 109 and the product of said reaction is further contacted with 9-aminominocycline using the conditions of Example 42 to give the product of the Example.

MS (ESI) m/z 820.37 (M+H);

HRMS: calcd for $C_{42}H_{53}N_5O_{12}$·HCl, 855.3458. found (ESI+), 820.37574;

Example 44

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,2-dimethylbutanoate

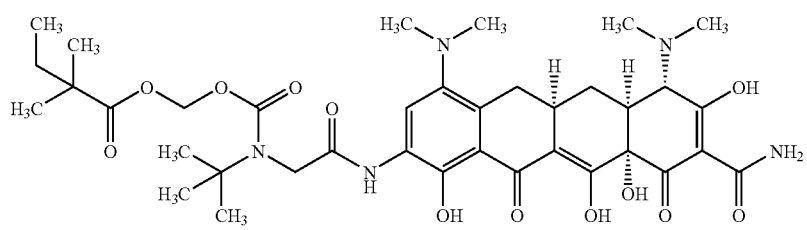

The title compound is prepared by reacting the product of the reaction of N-(tert-butyl)-N-({[(2,2-dimethylbutanoyl)oxy]methoxy}carbonyl)glycine using the conditions of Reference Compound 109 with 9-aminominocycline using the conditions of Example 42 to give the product of the Example.

MS (ESI) m/z 758.63 (M+H);

HRMS: calcd for $C_{37}H_{51}N_5O_{12}$·HCl, 793.3301. found (ESI+), 758.36119;

Example 45

Prepared According to Scheme 2

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-methylpropanoate

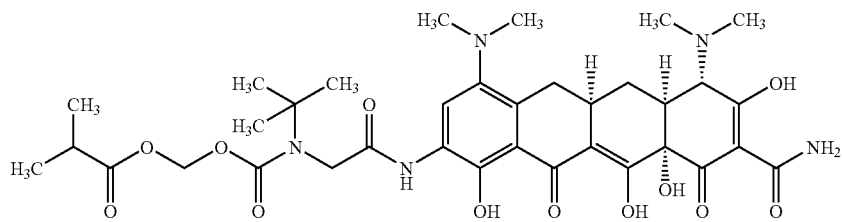

Reference Compound 58 is reacted under the conditions of Reference Compound 109 and the product of said reaction is further contacted with 9-aminominocycline using the conditions of Example 42 to give the product of the Example.

MS (ESI) m/z 730.38 (M+H);

HRMS: calcd for $C_{35}H_{47}N_5O_{12}$·HCl, 765.2988. found (ESI+), 730.33002;

Example 46

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl cyclopentanecarboxylate

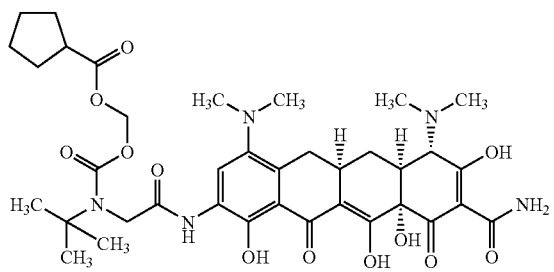

Reference Compound 59 is reacted under the conditions of Reference Compound 109 and the product of said reaction is further contacted with 9-aminominocycline using the conditions of Example 42 to give the product of the Example.

MS (ESI) m/z 754.09 ((M−H)−);

HRMS: calcd for $C_{37}H_{49}N_5O_{12}$·HCl, 791.3145. found (ESI+), 378.67644;

Example 47

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 4-methylbenzoate

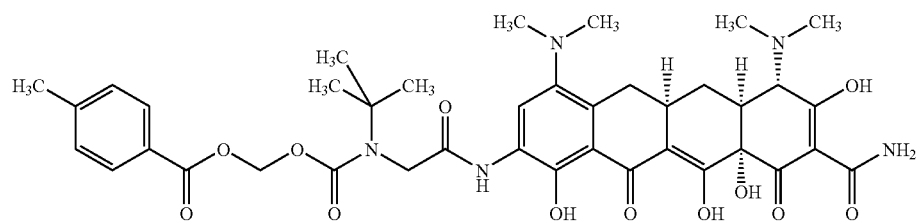

Reference Compound 60 is reacted under the conditions of Reference Compound 109 and the product of said reaction is further contacted with 9-aminominocycline using the conditions of Example 42 to give the product of the Example.

MS (ESI) m/z 778.34 (M+H);
HRMS: calcd for $C_{39}H_{47}N_5O_{12}$, 777.3221. found (ESI+), 778.33065;

Example 48

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl heptanoate

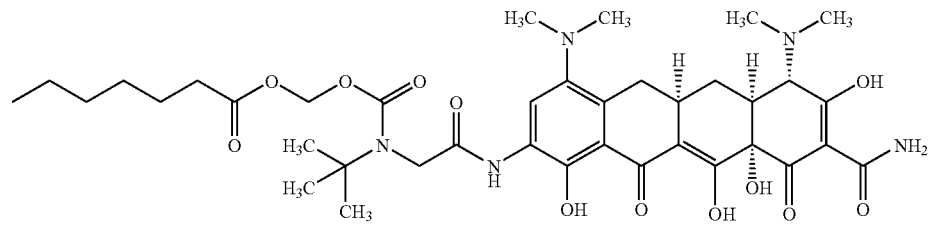

Reference Compound 61 is reacted under the conditions of Reference Compound 109 and the product of said reaction is further contacted with 9-aminominocycline using the conditions of Example 42 to give the product of the Example.

MS (ESI) m/z 772.45 (M+H);
HRMS: calcd for $C_{38}H_{53}N_5O_{12}$·HCl, 807.3458. found (ESI+), 772.37695;

Example 49

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl propionate

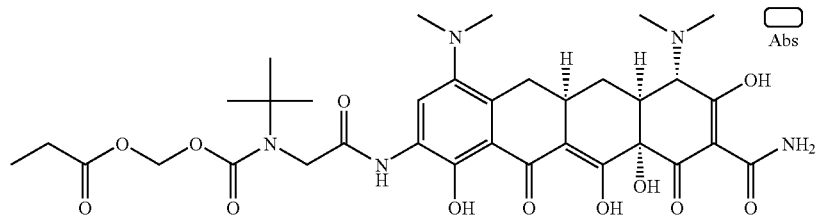

Reference Compound 62 is reacted under the conditions of Reference Compound 109 and the product of said reaction is further contacted with 9-aminominocycline using the conditions of Example 42 to give the product of the Example.

MS (ESI) m/z 716.3 (M+H);

HRMS: calcd for $C_{34}H_{45}N_5O_{12}$·HCl, 751.2832. found (ESI+), 716.31461;

Example 50

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl cyclohexanecarboxylate

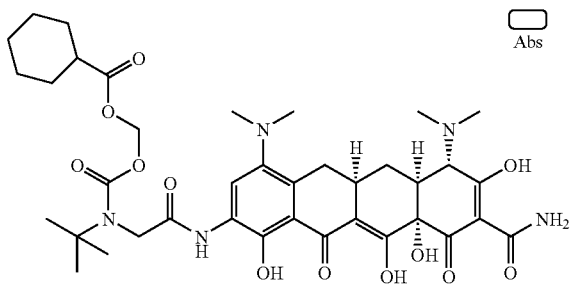

Reference Compound 63 is reacted under the conditions of Reference Compound 109 and the product of said reaction is further contacted with 9-aminominocycline using the conditions of Example 42 to give the product of the Example.

MS (ESI) m/z 770.36 (M+H);

HRMS: calcd for $C_{38}H_{51}N_5O_{12}$·HCl, 805.3301. found (ESI−), 768.34546;

Example 51

Prepared According to Scheme 2

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 3,5-dimethylbenzoate

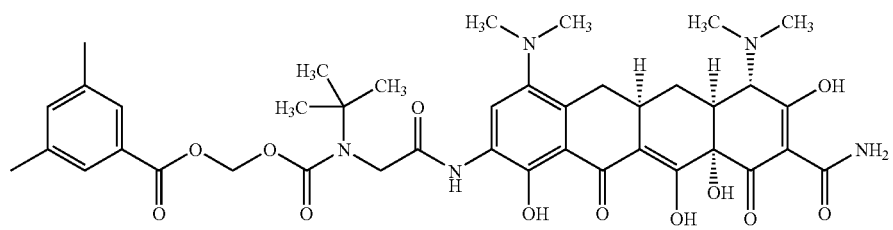

Reference Compound 64 is reacted under the conditions of Reference Compound 109 and the product of said reaction is further contacted with 9-aminominocycline using the conditions of Example 42 to give the product of the Example.

MS (ESI) m/z 792.32 (M+H);

HRMS: calcd for $C_{40}H_{49}N_5O_{12}$·HCl, 827.3145. found (ESI+), 792.34613;

Example 52

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-fluorobenzoate

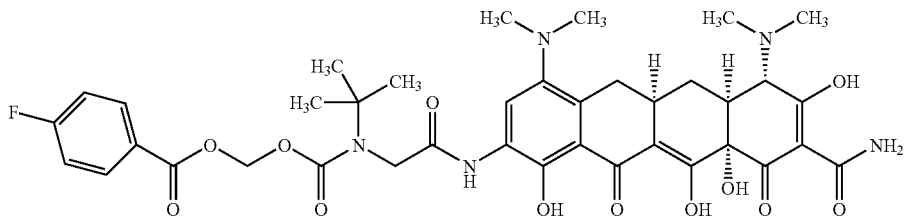

Reference Compound 65 is reacted under the conditions of Reference Compound 109 and the product of said reaction is further contacted with 9-aminominocycline using the conditions of Example 42 to give the product of the Example.

MS (ESI) m/z 782.3 (M+H);
HRMS: calcd for $C_{38}H_{44}FN_5O_{12}\cdot HCl$, 817.2737. found (ESI+), 782.30406;

Example 53

Prepared According to Scheme 2

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methylbutanoate

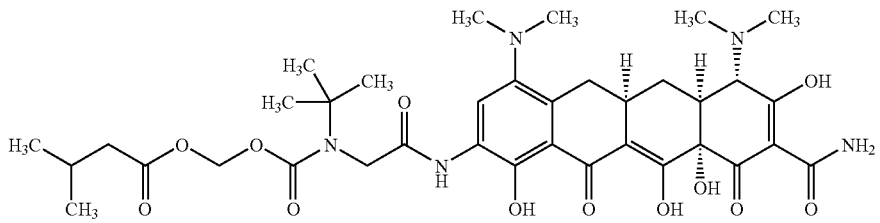

Reference Compound 66 is reacted under the conditions of Reference Compound 109 and the product of said reaction is further contacted with 9-aminominocycline using the conditions of Example 42 to give the product of the Example.

MS (ESI) m/z 744.37 (M+H);
HRMS: calcd for $C_{36}H_{49}N_5O_{12}\cdot HCl$, 779.3145. found (ESI+), 744.34481;

Example 54

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopentylacetate

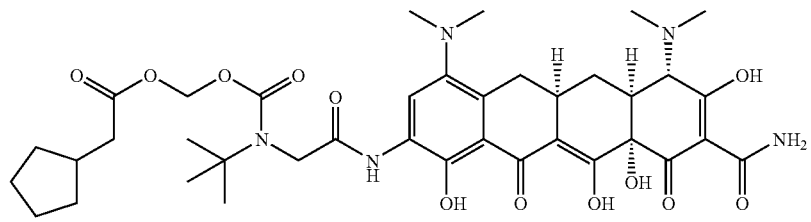

Reference Compound 67 is reacted under the conditions of Reference Compound 109 and the product of said reaction is further contacted with 9-aminominocycline using the conditions of Example 42 to give the product of the Example.

MS (ESI) m/z 770.4 (M+H);

HRMS: calcd for $C_{38}H_{51}N_5O_{12}$·HCl, 805.3301. found (ESI+), 770.35888;

Example 55

Prepared According to Scheme 2

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(trifluoromethyl)benzoate

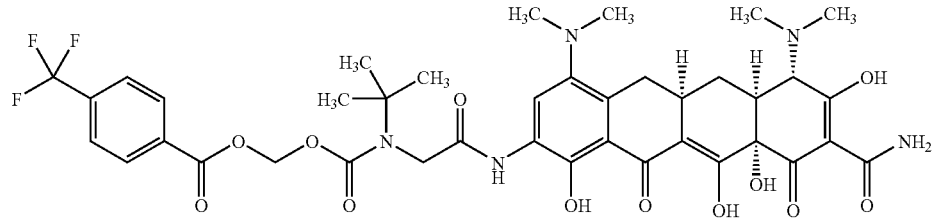

Reference Compound 68 is reacted under the conditions of Reference Compound 109 and the product of said reaction is further contacted with 9-aminominocycline using the conditions of Example 42 to give the product of the Example.

MS (ESI) m/z 832.2 (M+H);

MS (ESI) m/z 416.6 (M+2H);

HRMS: calcd for $C_{39}H_{44}F_3N_5O_{12}$·HCl, 867.2705. found (ESI+), 832.30055;

Example 56

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopropanecarboxylate

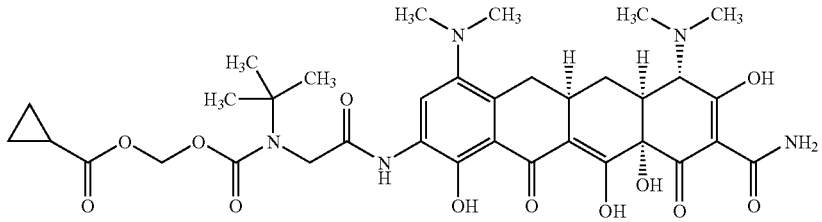

Reference Compound 69 is reacted under the conditions of Reference Compound 109 and the product of said reaction is further contacted with 9-aminominocycline using the conditions of Example 42 to give the product of the Example.
MS (ESI) m/z 728.34 (M+H);
HRMS: calcd for $C_{35}H_{45}N_5O_{12}$·HCl, 763.2832. found (ESI+), 728.31289;

Example 57

Prepared According to Scheme 2

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl adamantane-1-carboxylate

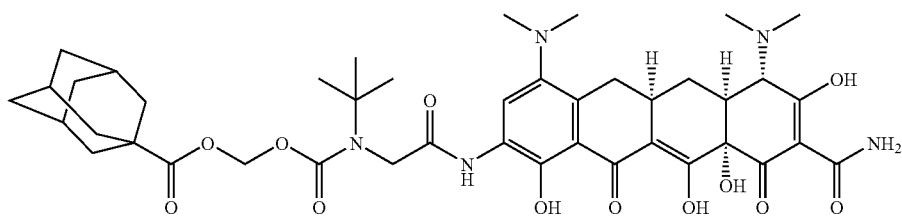

Reference Compound 70 is reacted under the conditions of Reference Compound 109 and the product of said reaction is further contacted with 9-aminominocycline using the conditions of Example 42 to give the product of the Example.
MS (ESI) m/z 822.5 (M+H);
HRMS: calcd for $C_{42}H_{55}N_5O_{12}$·HCl, 857.3614. found (ESI+), 822.39237;

Example 58 butyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate

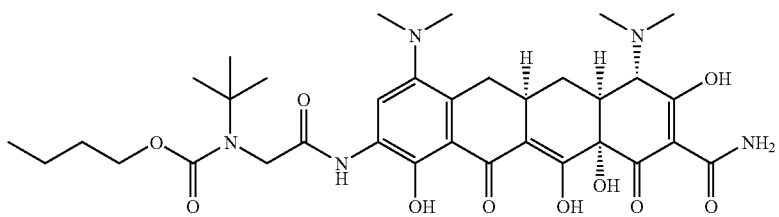

The title compound is prepared by the procedure of Example 42, using 1 equivalent of 9-amino-minocycline and 2 equivalents of isobutoxycarbonyl N-(butoxycarbonyl)-N-(tert-butyl)glycinate Reference Example 118 to give the product of the example.
MS (ESI) m/z 686.4 (M+H);
HRMS: calcd for $C_{34}H_{47}N_5O_{10}$·HCl, 721.3090. found (ESI+), 686.34079;

Example 59 isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate

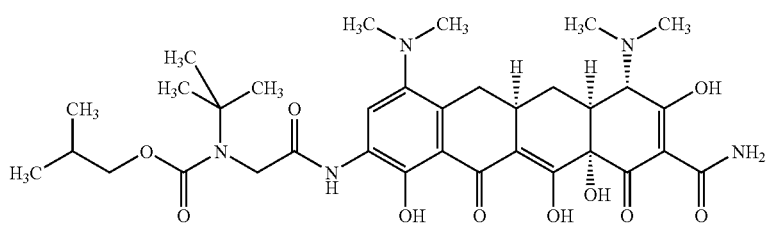

The title compound is prepared by the procedure of Example 42, using 1 equivalent of 9-amino-minocycline and 2 equivalents of isobutoxycarbonyl N-(tert-butyl)-N-(isobutoxycarbonyl)glycinate, Reference Example 119 to give the product of the example.

MS (ESI) m/z 686.3 (M+H);
MS (ESI) m/z 1371.7 (2M+H);
HRMS: calcd for $C_{34}H_{47}N_5O_{10}$·HCl, 721.3090. found (ESI–), 684.32433;

Example 60 methyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate

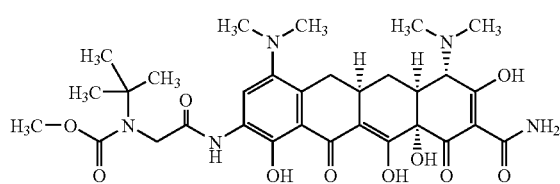

The title compound is prepared by the procedure of Example 42, using 1 equivalent of 9-amino-minocycline and 2 equivalents of isobutoxycarbonyl N-(tert-butyl)-N-(methoxycarbonyl)glycinate Reference Example 120 to give the product of the example.

MS (ESI) m/z 644.3 (M+H);

MS (ESI) m/z 322.6 (M+2H);

HRMS: calcd for $C_{31}H_{41}N_5O_{10}$·HCl, 679.2620. found (ESI–), 642.27736;

Example 61

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl pentanoate

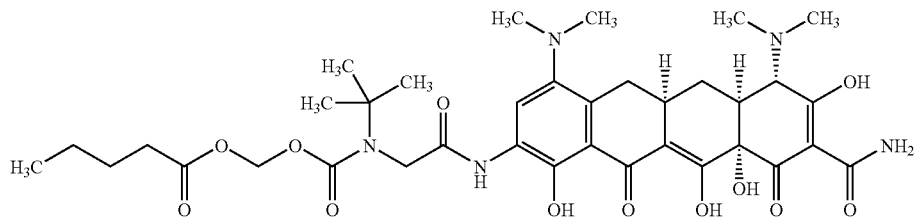

Reference Compound 71 is reacted under the conditions of Reference Compound 109 and the product of said reaction is further contacted with 9-aminominocycline using the conditions of Example 42 to give the product of the Example.
MS (ESI) m/z 742 (M–H);
HRMS: calcd for $C_{36}H_{49}N_5O_{12}$·HCl, 779.3145. found (ESI+), 744.34613;

Example 62

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclobutanecarboxylate

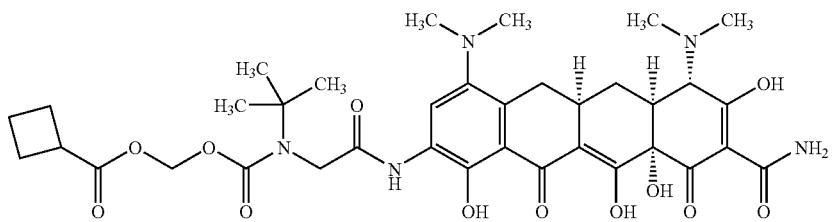

Reference Compound 72 is reacted under the conditions of Reference Compound 109 and the product of said reaction is further contacted with 9-aminominocycline using the conditions of Example 42 to give the product of the Example.

MS (ESI) m/z 742.4 (M+H);

Example 63

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 3-cyclohexylpropanoate

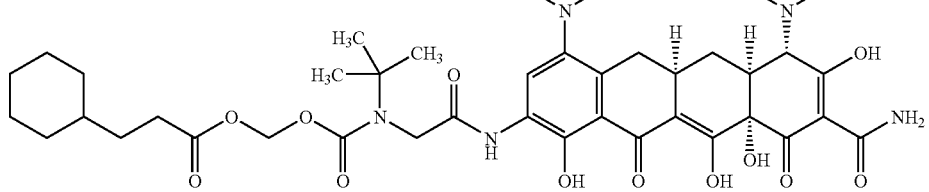

Reference Compound 73 is reacted under the conditions of Reference Compound 109 and the product of said reaction is further contacted with 9-aminominocycline using the conditions of Example 42 to give the product of the Example.
MS (ESI) m/z 796.4 (M–H);

Example 64

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl (4-fluorophenoxy)acetate

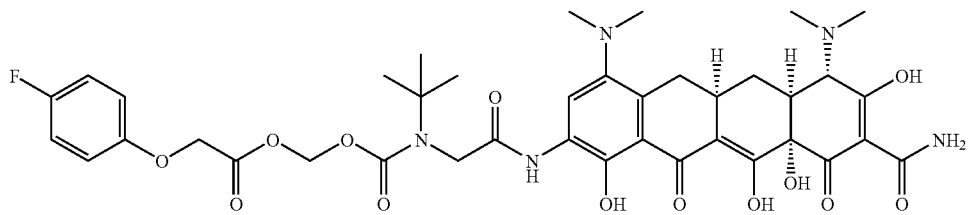

Reference Compound 74 is reacted under the conditions of Reference Compound 109 and the product of said reaction is further contacted with 9-aminominocycline using the conditions of Example 42 to give the product of the Example.
MS (ESI) m/z 812.4 (M+H);
MS (ESI) m/z 406.7 (M+2H);
HRMS: calcd for $C_{39}H_{46}FN_5O_{13}$·HCl, 847.2843. found (ESI+), 812.31518;

Example 65

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl cyclohexylacetate

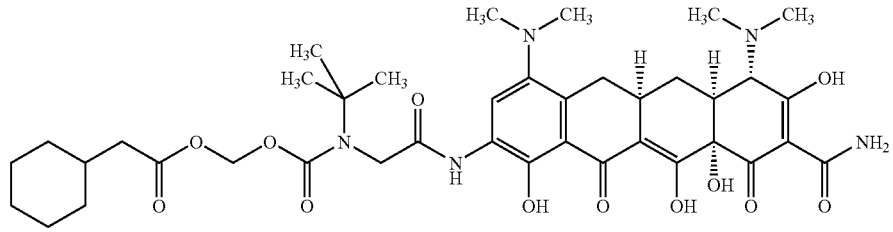

Reference Compound 75 is reacted under the conditions of Reference Compound 109 and the product of said reaction is further contacted with 9-aminominocycline using the conditions of Example 42 to give the product of the Example.
MS (ESI) m/z 782.2 (M–H);
HRMS: calcd for $C_{39}H_{53}N_5O_{12}$.HCl, 819.3458. found (ESI+), 784.37621;

Example 66

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 2,6-dimethylbenzoate

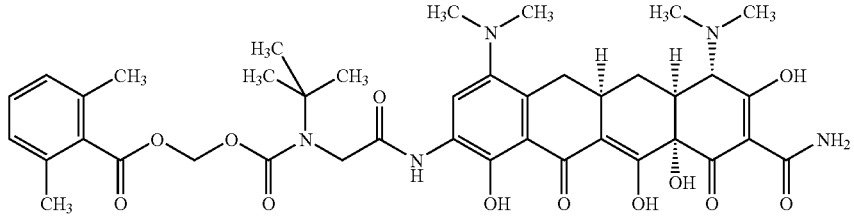

Reference Compound 76 is reacted under the conditions of Reference Compound 109 and the product of said reaction is further contacted with 9-aminominocycline using the conditions of Example 42 to give the product of the Example.
MS (ESI) m/z 790.4 (M–H);
HRMS: calcd for $C_{40}H_{49}N_5O_{12}$.HCl, 827.3145. found (ESI+), 792.34423;

Example 67

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl phenylacetate

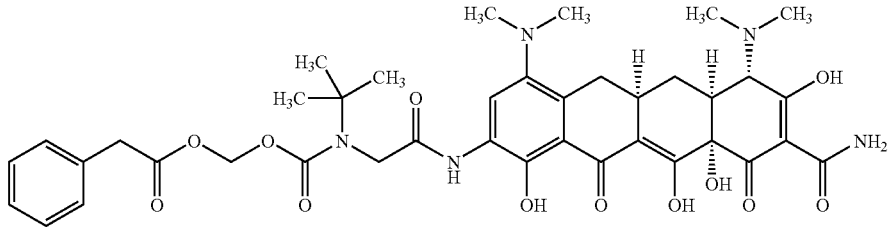

Reference Compound 77 is reacted under the conditions of Reference Compound 109 and the product of said reaction is further contacted with 9-aminominocycline using the conditions of Example 42 to give the product of the Example.
MS (ESI) m/z 778.3 (M+H);
HRMS: calcd for $C_{39}H_{47}N_5O_{12}$.HCl, 813.2988. found (ESI+), 778.3299;

Example 68

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl pivalate

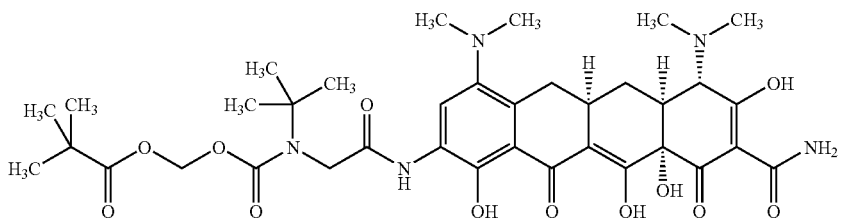

Reference Compound 78 is reacted under the conditions of Reference Compound 109 and the product of said reaction is further contacted with 9-aminominocycline using the conditions of Example 42 to give the product of the Example.

MS (ESI) m/z 744.5 (M+H);

HRMS: calcd for $C_{36}H_{49}N_5O_{12}$.HCl, 779.3145. found (ESI+), 744.34434;

Example 69

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-benzofuran-2-carboxylate

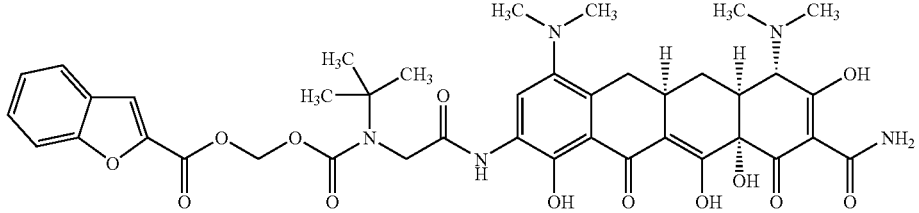

Reference Compound 79 is reacted under the conditions of Reference Compound 109 and the product of said reaction is further contacted with 9-aminominocycline using the conditions of Example 42 to give the product of the Example.

MS (ESI) m/z 804.4 (M+H);
MS (ESI) m/z 402.7 (M+2H);
HRMS: calcd for $C_{40}H_{45}N_5O_{13}$.HCl, 839.2781. found (ESI+), 804.30779;

Example 70

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-benzofuran-2-carboxylate

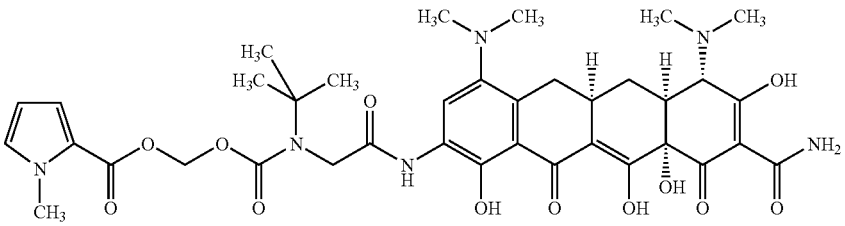

Reference Compound 80 is reacted under the conditions of Reference Compound 109 and the product of said reaction is further contacted with 9-aminominocycline using the conditions of Example 42 to give the product of the Example.

MS (ESI) m/z 767.4 (M+H);
HRMS: calcd for $C_{37}H_{46}N_6O_{12}$, 766.3174. found (ESI+), 767.32406;

Example 71

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1,1'-biphenyl-4-carboxylate

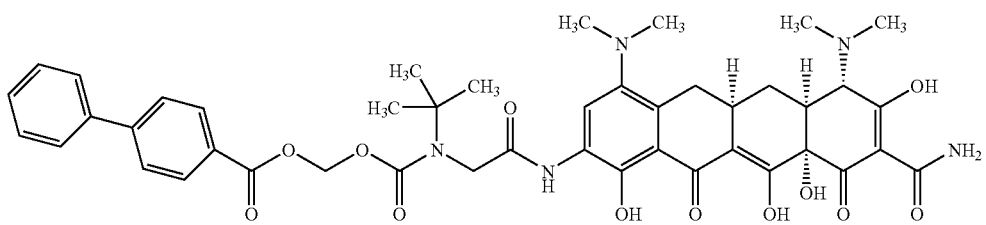

Reference Compound 81 is reacted under the conditions of Reference Compound 109 and the product of said reaction is further contacted with 9-aminominocycline using the conditions of Example 42 to give the product of the Example.
MS (ESI) m/z 838.2 (M−H);
MS (ESI) f/z 113 (TFA-H);
HRMS: calcd for C$_{44}$H$_{49}$N$_5$O$_{12}$.HCl, 875.3145. found (ESI+), 840.34496;

Example 72

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 4-methoxybenzoate

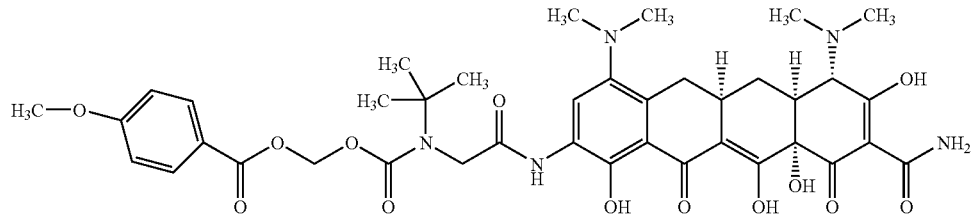

Reference Compound 82 is reacted under the conditions of Reference Compound 109 and the product of said reaction is further contacted with 9-aminominocycline using the conditions of Example 42 to give the product of the Example.
MS (ESI) m/z 792.3 (M−H);
HRMS: calcd for C$_{39}$H$_{47}$N$_5$O$_{13}$.HCl, 829.2937. found (ESI+), 794.32511;

Example 73

Prepared According to Scheme II ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 1H-indole-2-carboxylate

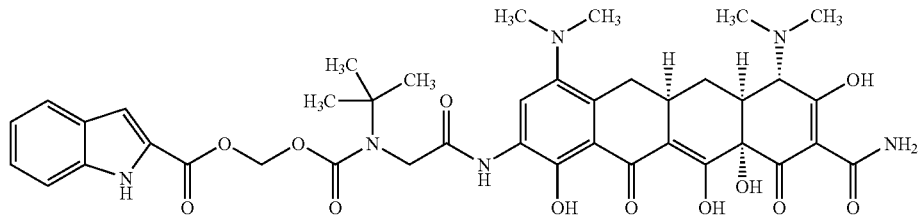

Reference Compound 83 is reacted under the conditions of Reference Compound 109 and the product of said reaction is further contacted with 9-aminominocycline using the conditions of Example 42 to give the product of the Example.
MS (ESI) f/z 803.4 (M+H);
HRMS: calcd for C$_{40}$H$_{46}$N$_6$O$_{12}$.HCl, 838.2941. found (ESI+), 803.32375;

Example 74

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl diphenylacetate

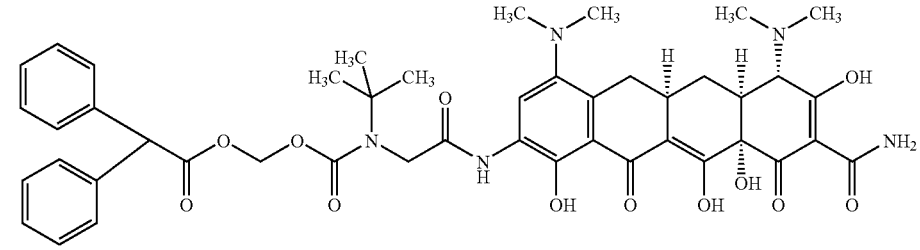

Reference Compound 84 is reacted under the conditions of Reference Compound 109 and the product of said reaction is further contacted with 9-aminominocycline using the conditions of Example 42 to give the product of the Example.

MS (ESI) m/z 852.4 (M−H);

HRMS: calcd for $C_{45}H_{51}N_5O_{12}$.HCl, 889.3301. found (ESI−), 852.3463;

Example 75

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl thiophene-2-carboxylate

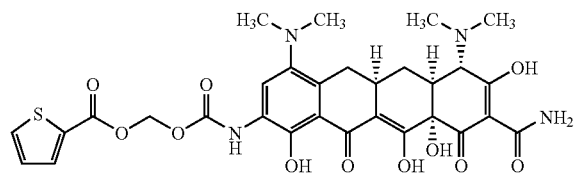

The title compound is prepared by the procedure of Example 42, using [(chlorocarbonyl)oxy]methyl thiophene-2-carboxylate in place of the Reference Compound 109 to give the product of the example.

MS (ESI) m/z 655.2 (M−H);

HRMS: calcd for $C_{30}H_{32}N_4O_{11}S$.HCl, 692.1555. found (ESI+), 657.18613;

Example 76

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 4-fluorobenzoate

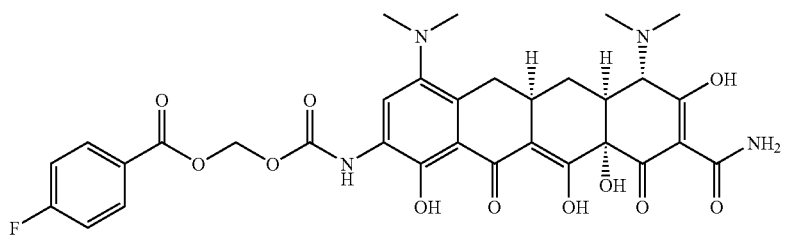

The title compound is prepared by the procedure of Example 42, using [(chlorocarbonyl)oxy]methyl 4-fluorobenzoate in place of the Reference Compound 109 to give the product of the example.

MS (ESI) m/z 667.2 (M−H);

HRMS: calcd for $C_{32}H_{33}FN_4O_{11}$.HCl, 704.1897. found (ESI+), 669.22024;

Example 77

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 3,5-dimethylbenzoate

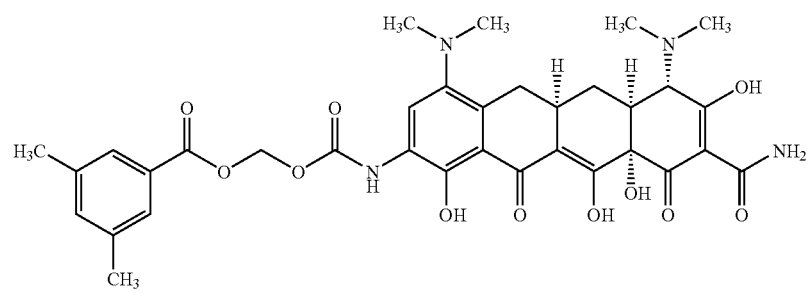

The title compound is prepared by the procedure of Example 42, using [(chlorocarbonyl)oxy]methyl 3,5-dimethylbenzoate in place of the Reference Compound 109 to give the product of the example.

MS (ESI) m/z 679.2 (M+H);

HRMS: calcd for $C_{34}H_{38}N_4O_{11} \cdot HCl$, 714.2304. found (ESI+), 679.26076;

Example 78

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl pivalate

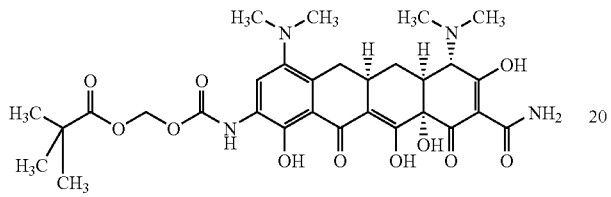

The title compound is prepared by the procedure of Example 42, using [(chlorocarbonyl)oxy]methyl pivalate in place of the Reference Compound 109 to give the product of the example.

MS (ESI) m/z 631.2 (M+H);

HRMS: calcd for $C_{30}H_{38}N_4O_{11} \cdot HCl$, 666.2304. found (ESI+), 631.26094;

Example 79

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 3,3-dimethylbutanoate

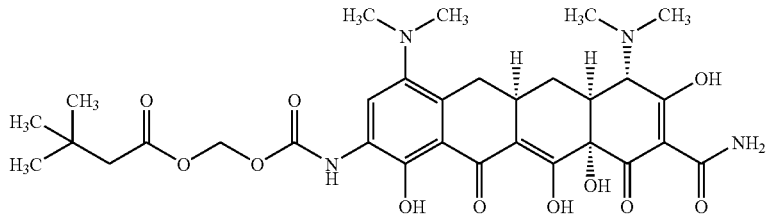

The title compound is prepared by the procedure of Example 42, using [(chlorocarbonyl)oxy]methyl 3,3-dimethylbutanoate in place of the Reference Compound 109 to give the product of the example.

MS (ESI) m/z 643.3 (M−H);

HRMS: calcd for $C_{31}H_{40}N_4O_{11} \cdot HCl$, 680.2460. found (ESI+), 645.27632;

Example 80

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 2,2-dimethylbutanoate

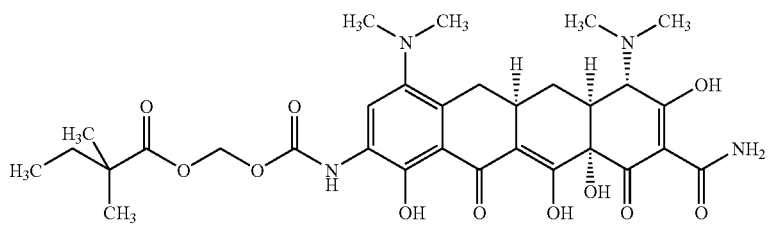

The title compound is prepared by the procedure of Example 42, using [(chlorocarbonyl)oxy]methyl 2,2-dimethylbutanoate in place of the Reference Compound 109 to give the product of the example.

MS (ESI) m/z 645.2 (M+H);
HRMS: calcd for $C_{31}H_{40}N_4O_{11}$·HCl, 680.2460. found (ESI+), 645.27637;

Example 81

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-naphthoate

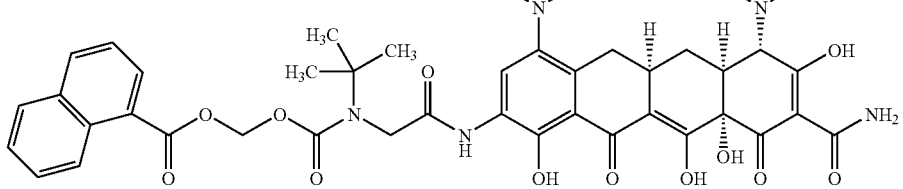

Reference Compound 85 is reacted under the conditions of Reference Compound 109 and the product of said reaction is further contacted with 9-aminominocycline using the conditions of Example 42 to give the product of the Example.

MS (ESI) m/z 812.5 (M–H);
HRMS: calcd for $C_{42}H_{47}N_5O_{12}$·HCl, 849.2988. found (ESI+), 814.33029;

Example 82

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-naphthoate

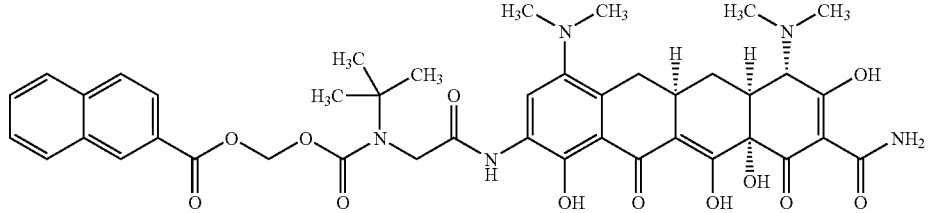

Reference Compound 86 is reacted under the conditions of Reference Compound 109 and the product of said reaction is further contacted with 9-aminominocycline using the conditions of Example 42 to give the product of the Example.

MS (ESI) m/z 812.5 (M–H);
HRMS: calcd for $C_{42}H_{47}N_5O_{12}$·HCl, 849.2988. found (ESI+), 814.33004;

Example 83

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-methyl-1H-indole-3-carboxylate

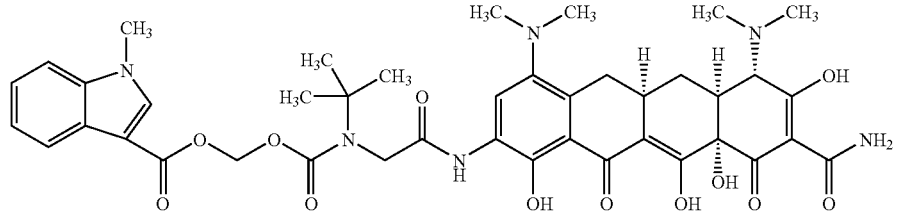

Reference Compound 87 is reacted under the conditions of Reference Compound 109 and the product of said reaction is further contacted with 9-aminominocycline using the conditions of Example 42 to give the product of the Example.
MS (ESI) m/z 815.5 (M−H);
HRMS: calcd for $C_{41}H_{48}N_6O_{12}$·HCl, 852.3097. found (ESI−), 815.32484;

Example 84

({[(2-{[[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl quinoline-2-carboxylate

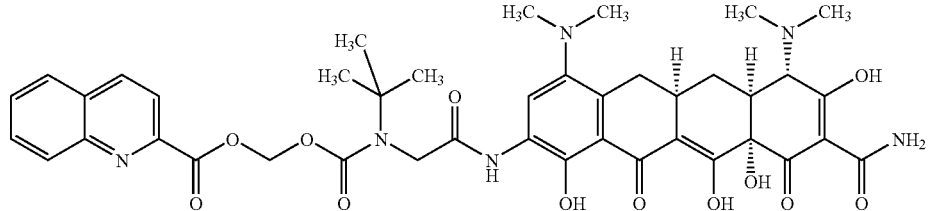

Reference Compound 88 is reacted under the conditions of Reference Compound 109 and the product of said reaction is further contacted with 9-aminominocycline using the conditions of Example 42 to give the product of the Example.
MS (ESI) m/z 813.5 (M−H);
HRMS: calcd for $C_{41}H_{46}N_6O_{12}$·HCl, 850.2941. found (ESI+), 815.32509;

Example 85

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 2-ethylbutanoate

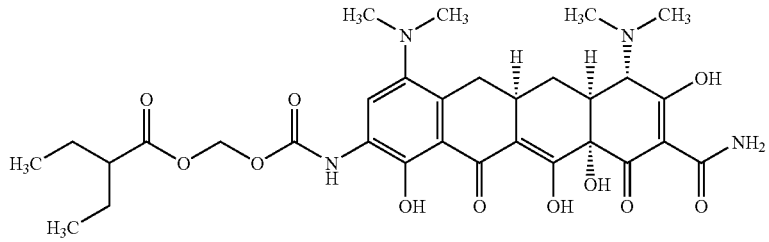

The title compound is prepared by the procedure of Example 42, using [(chlorocarbonyl)oxy]methyl 2-ethylbutanoate in place of the Reference Compound 109 to give the product of the example.
MS (ESI) m/z 643.4 (M−H);
MS (ESI) m/z 1287.7 (2M−H);
HRMS: calcd for $C_{31}H_{40}N_4O_{11}$·HCl, 680.2460. found (ESI+), 645.27618;

Example 86

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl cyclopentylacetate

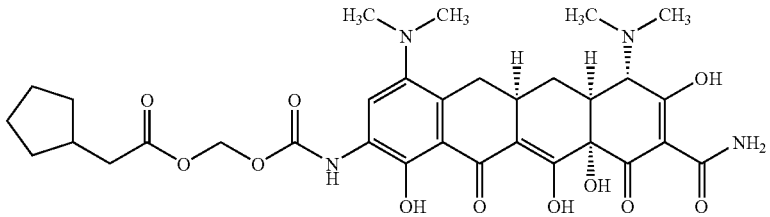

The title compound is prepared by the procedure of Example 42, using [(chlorocarbonyl)oxy]methyl cyclopentylacetate in place of the Reference Compound 109 to give the product of the example.

MS (ESI) m/z 655.3 (M−H);
MS (ESI) m/z 1311.7 (2M−H);
HRMS: calcd for $C_{32}H_{40}N_4O_{11}$·HCl, 692.2460. found (ESI+), 657.27572;

Example 87

Prepared According to Scheme 6

[({[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}carbonyl)oxy]methyl 4-tert-butylbenzoate

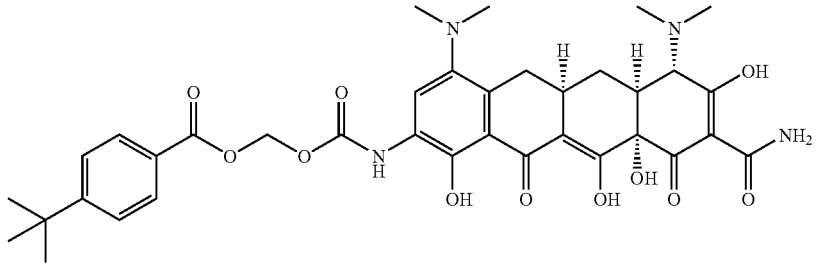

The title compound is prepared by the procedure of Example 42, using [(chlorocarbonyl)oxy]methyl 4-tert-butylbenzoate in place of the Reference Compound 109 to give the product of the example.

MS (ESI) m/z 705.1 (M−H);
MS (ESI) m/z 1410.9 (2M−H);
HRMS: calcd for $C_{36}H_{42}N_4O_{11}$·HCl, 742.2617. found (ESI+), 707.29336;

Example 88

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl nicotinate

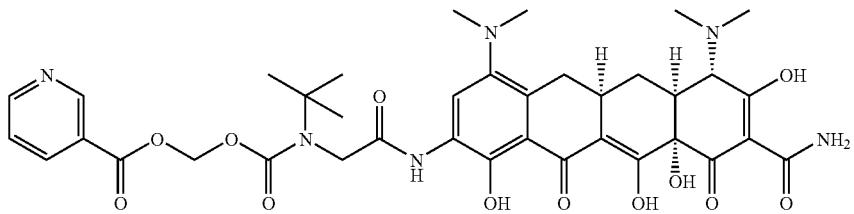

Reference Compound 89 is reacted under the conditions of Reference Compound 109 and the product of said reaction is further contacted with 9-aminominocycline using the conditions of Example 42 to give the product of the Example.

MS (ESI) m/z 763.5 (M−H);
HRMS: calcd for $C_{37}H_{44}N_6O_{12}$·HCl, 800.2784. found (ESI+), 765.30896;

Example 89

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl isonicotinate

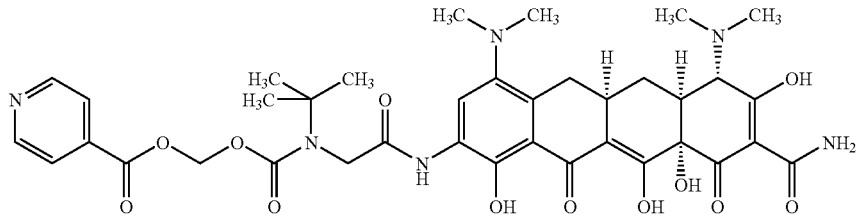

Reference Compound 90 is reacted under the conditions of Reference Compound 109 and the product of said reaction is further contacted with 9-aminominocycline using the conditions of Example 42 to give the product of the Example.

HRMS: calcd for $C_{37}H_{44}N_6O_{12}\cdot HCl$, 800.2784. found (ESI+), 765.3117;

Example 90

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 2,6-difluorobenzoate

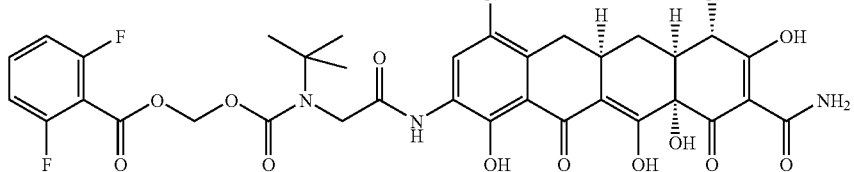

Reference Compound 91 is reacted under the conditions of Reference Compound 109 and the product of said reaction is further contacted with 9-aminominocycline using the conditions of Example 42 to give the product of the Example.

MS (ESI) m/z 798.2 (M−H);
HRMS: calcd for $C_{38}H_{43}F_2N_5O_{12}\cdot HCl$, 835.2643. found (ESI+), 800.29464;

Example 91

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 2-fluorobenzoate

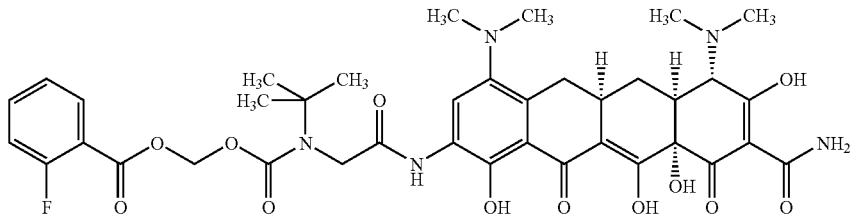

Reference Compound 92 is reacted under the conditions of Reference Compound 109 and the product of said reaction is further contacted with 9-aminominocycline using the conditions of Example 42 to give the product of the Example.

MS (ESI) m/z 780 (M−H);
HRMS: calcd for $C_{38}H_{44}FN_5O_{12}\cdot HCl$, 817.2737. found (ESI+), 782.30558;

Example 92

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 2-(trifluoromethyl)benzoate

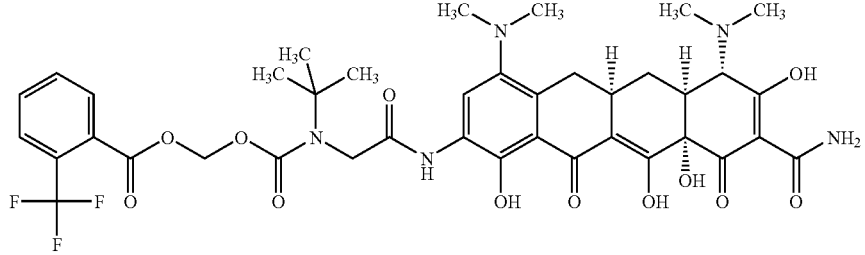

Reference Compound 93 is reacted under the conditions of Reference Compound 109 and the product of said reaction is further contacted with 9-aminominocycline using the conditions of Example 42 to give the product of the Example.

HRMS: calcd for $C_{39}H_{44}F_3N_5O_{12}$·HCl, 867.2705. found (ESI+), 832.30026;

Example 93

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-pyrrolidin-1-ylbenzoate

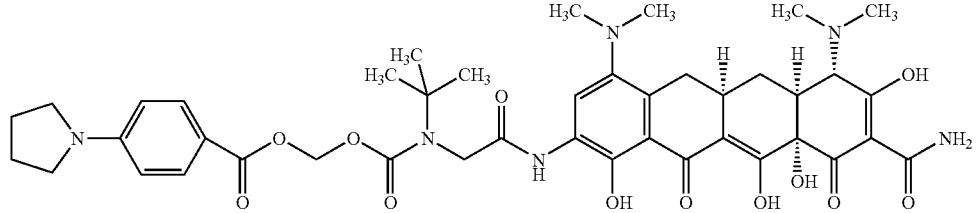

Reference Compound 94 is reacted under the conditions of Reference Compound 109 and the product of said reaction is further contacted with 9-aminominocycline using the conditions of Example 42 to give the product of the Example.

MS (ESI) m/z 833.4 (M+H);
HRMS: calcd for $C_{42}H_{52}N_6O_{12}$·HCl, 868.3410. found (ESI−), 831.3565;

Example 94

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1,1'-biphenyl-2-carboxylate

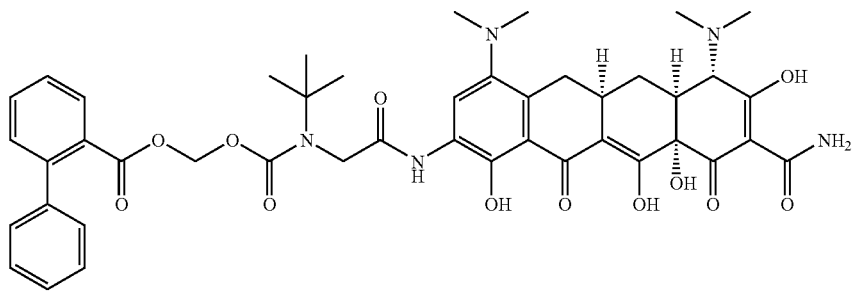

Reference Compound 95 is reacted under the conditions of Reference Compound 109 and the product of said reaction is further contacted with 9-aminominocycline using the conditions of Example 42 to give the product of the Example.

MS (ESI) m/z 838.4 (M−H);
HRMS: calcd for $C_{44}H_{49}N_5O_{12}$·HCl, 875.3145. found (ESI+), 840.34553;

Example 95

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,4,6-trimethylbenzoate

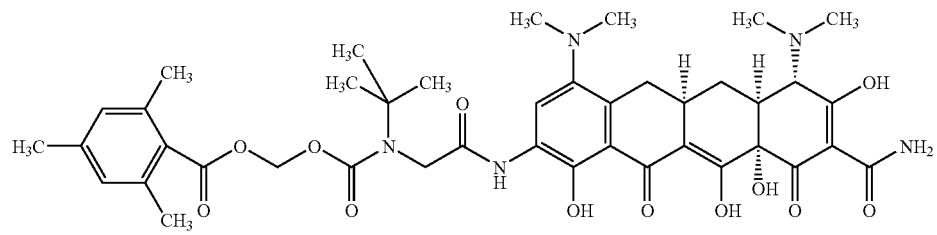

Reference Compound 96 is reacted under the conditions of Reference Compound 109 and the product of said reaction is further contacted with 9-aminominocycline using the conditions of Example 42 to give the product of the Example.
MS (ESI) m/z 804.5 (M−H);
HRMS: calcd for $C_{41}H_{51}N_5O_{12}$·HCl, 841.3301. found (ESI+), 806.36101;

Example 96

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 4-isopropoxybenzoate

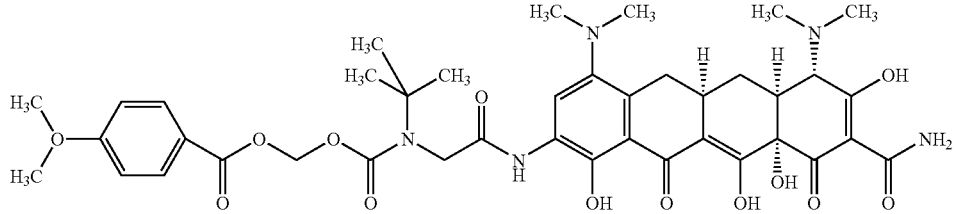

Reference Compound 97 is reacted under the conditions of Reference Compound 109 and the product of said reaction is further contacted with 9-aminominocycline using the conditions of Example 42 to give the product of the Example.
MS (ESI) m/z 820.2 (M−H);
HRMS: calcd for $C_{41}H_{51}N_5O_{13}$·HCl, 857.3250. found (ESI−), 820.34117;

Example 97

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 3,4,5-trimethoxybenzoate

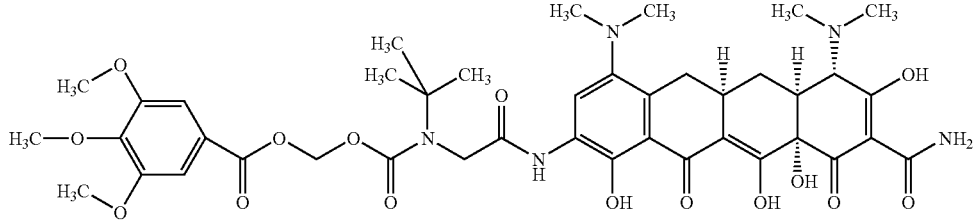

Reference Compound 98 is reacted under the conditions of Reference Compound 109 and the product of said reaction is further contacted with 9-aminominocycline using the conditions of Example 42 to give the product of the Example.
MS (ESI) m/z 852.2 (M−H);
HRMS: calcd for $C_{41}H_{51}N_5O_{15}$·HCl, 889.3148. found (ESI+), 854.34728;

Example 98

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 3,5-dimethoxybenzoate

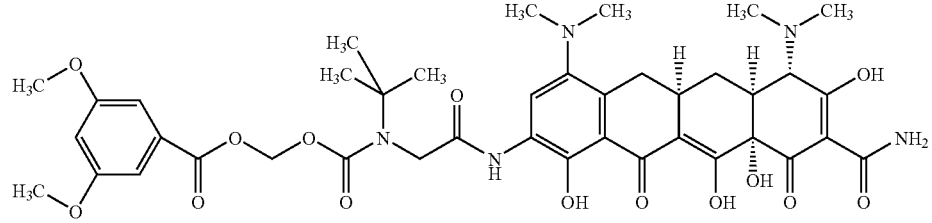

151

Reference Compound 99 is reacted under the conditions of Reference Compound 109 and the product of said reaction is further contacted with 9-aminominocycline using the conditions of Example 42 to give the product of the Example.

MS (ESI) m/z 822.1 (M–H);
HRMS: calcd for $C_{40}H_{49}N_5O_{14}$, 824.3349. found (ESI+), 824.3351;

152

Example 99

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl (2E)-3-phenylprop-2-enoate

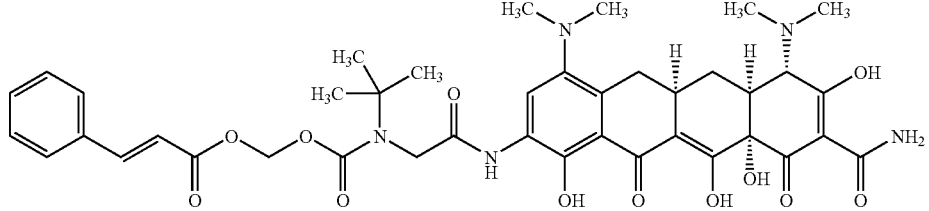

Reference Compound 100 is reacted under the conditions of Reference Compound 109 and the product of said reaction is further contacted with 9-aminominocycline using the conditions of Example 42 to give the product of the Example.

MS (ESI) m/z 788.3 (M–H);
HRMS: calcd for $C_{40}H_{47}N_5O_{12} \cdot HCl$, 825.2988. found (ESI+), 790.33068;

Example 100

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methyl-1-benzofuran-2-carboxylate

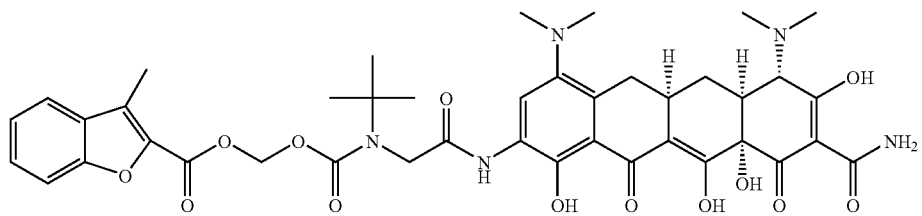

Reference Compound 101 is reacted under the conditions of Reference Compound 109 and the product of said reaction is further contacted with 9-aminominocycline using the conditions of Example 42 to give the product of the Example.

MS (ESI) m/z 816.5 (M–H);
HRMS: calcd for $C_{41}H_{47}N_5O_{13} \cdot HCl$, 853.2937. found (ESI+), 818.3234;

Example 101

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl[3,5-bis(trifluoromethyl)phenyl]acetate

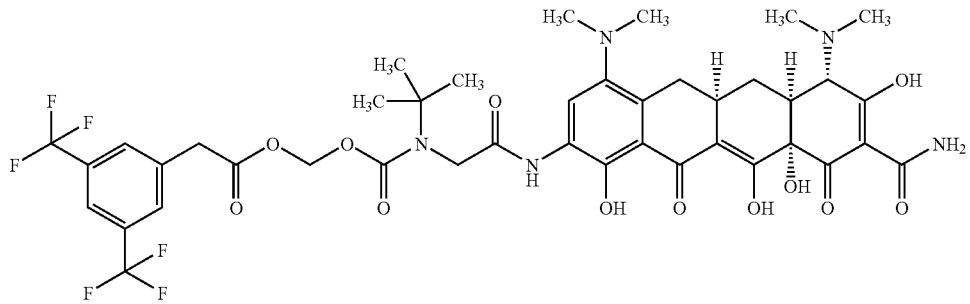

Reference Compound 102 is reacted under the conditions of Reference Compound 109 and the product of said reaction is further contacted with 9-aminominocycline using the conditions of Example 42 to give the product of the Example.
MS (ESI) m/z 912 (M−H);
HRMS: calcd for $C_{41}H_{45}F_6N_5O_{12}$·HCl, 949.2736. found (ESI+), 914.30367;

Example 102

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(heptyloxy)benzoate

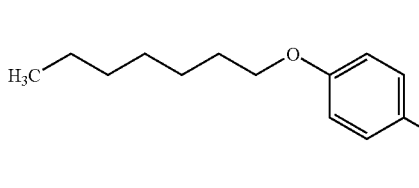

Reference Compound 103 is reacted under the conditions of Reference Compound 109 and the product of said reaction is further contacted with 9-aminominocycline using the conditions of Example 42 to give the product of the Example.
MS (ESI) m/z 876.1 (M−H);
HRMS: calcd for $C_{45}H_{59}N_5O_{13}$·HCl, 913.3876. found (ESI+), 878.41791;

Example 103

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-(2-phenylethyl)benzoate

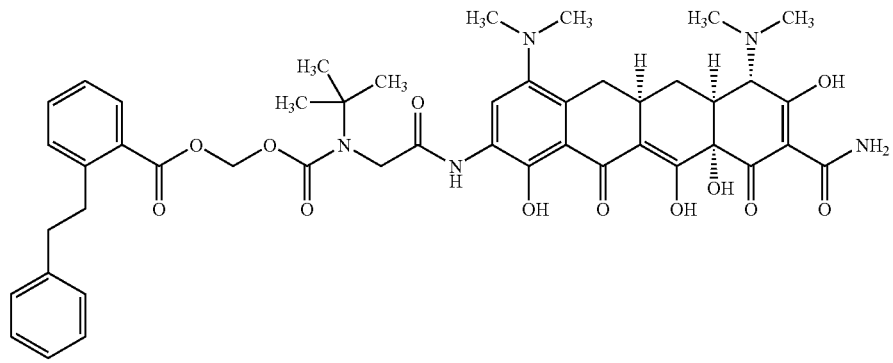

Reference Compound 104 is reacted under the conditions of Reference Compound 109 and the product of said reaction is further contacted with 9-aminominocycline using the conditions of Example 42 to give the product of the Example.
MS (ESI) m/z 866.5 (M−H);
HRMS: calcd for $C_{46}H_{53}N_5O_{12}$·HCl, 903.3458. found (ESI), 868.37357;

Example 104

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(dodecyloxy)benzoate

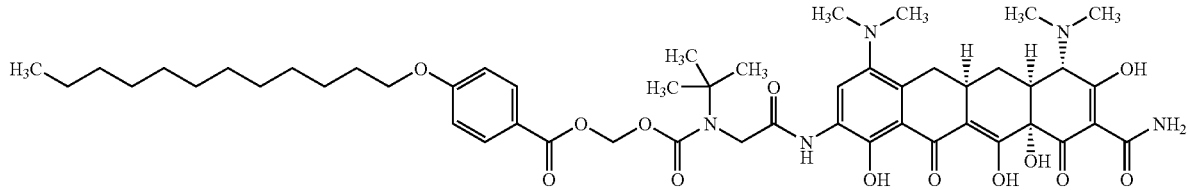

Reference Compound 105 is reacted under the conditions of Reference Compound 109 and the product of said reaction is further contacted with 9-aminominocycline using the conditions of Example 42 to give the product of the Example.

MS (ESI) m/z 946.7 (M–H);

HRMS: calcd for $C_{50}H_{69}N_5O_{13}$·HCl, 983.4659. found (ESI–), 946.48106;

Example 105

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 4-(acetylamino)benzoate

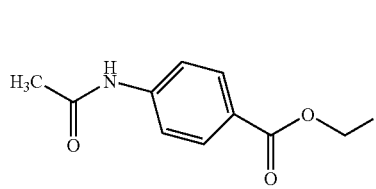
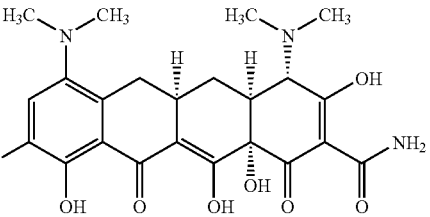

Reference Compound 106 is reacted under the conditions of Reference Compound 109 and the product of said reaction is further contacted with 9-aminominocycline using the conditions of Example 42 to give the product of the Example.

MS (ESI) m/z 819.1 (M–H);

HRMS: calcd for $C_{40}H_{48}N_6O_{13}$·HCl, 856.3046. found (ESI–), 819.32051;

Example 106

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl anthracene-9-carboxylate

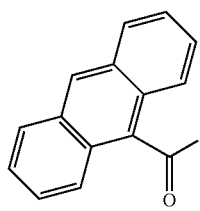
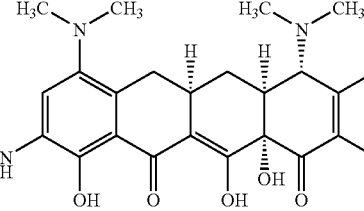

Reference Compound 107 is reacted under the conditions of Reference Compound 109 and the product of said reaction is further contacted with 9-aminominocycline using the conditions of Example 42 to give the product of the Example.

MS (ESI) m/z 864.3 (M+H);

HRMS: calcd for $C_{46}H_{49}N_5O_{12}$·HCl, 899.3145. found (ESI–), 862.32855;

Example 107

({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy) methyl 4-benzoylbenzoate

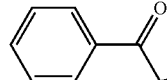
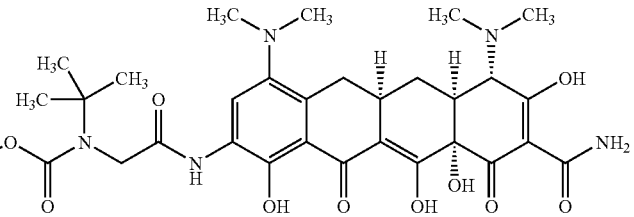

Reference Compound 108 is reacted under the conditions of Reference Compound 109 and the product of said reaction is further contacted with 9-aminominocycline using the conditions of Example 42 to give the product of the Example.

MS (ESI) m/z 866.3 (M−H);

HRMS: calcd for $C_{45}H_{49}N_5O_{13}$·HCl, 903.3094. found (ESI−), 866.32405;

Example 108

(5-methyl-2-oxo-1,3-dioxol-4-yl)methyl 2-{[(7S,10aR)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl (propyl)carbamate

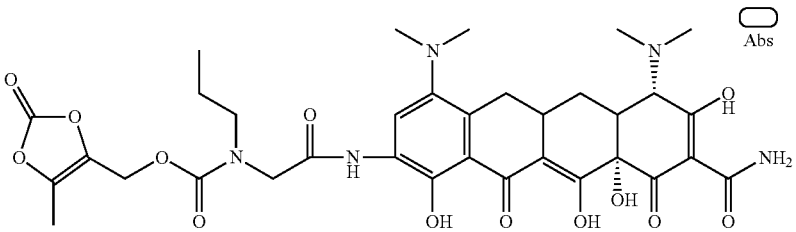

To a solution of 107 mg (0.166 mmol) of N-propyl-glycyl-cycline (N-prop-glycyl) in DMPU (2 ml) is added 5 equivalents of sodium carbonate (95 mg, 0.9 mmol) followed by 2 equivalents of (5-methyl-2-oxo-1,3-dioxol-4-yl)methyl 4-nitrophenyl carbonate (95 mg, 0.33 mmol) Reference Compound 121 and stirring for 2 hr at room temperature. The reaction mixture is filtered through diatomaceous earth and the filtrate added to a mixture of (1:4)(20 ml) ether:isopropyl alcohol and HCl (1M in ether) is added and the formed solid filtered, redissolved in water, the pH adjusted to about 2 and extracted with methylene chloride to give 15 mg of the product of the Example.

MS (ESI) m/z 728.5 (M+H);

MS (ESI) m/z 364.8 (M+2H);

HRMS: calcd for $C_{34}H_{41}N_5O_{13}$, 727.2701. found (ESI+), 728.27606;

Example 109

(5-methyl-2-oxo-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl (butyl)carbamate

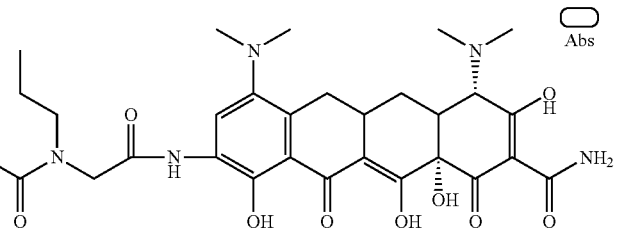

The title compound is prepared by the procedure of Example 108, using N-butyl-glycylcycline (N-bu-glycyl) and (5-methyl-2-oxo-1,3-dioxol-4-yl)methyl 4-nitrophenyl carbonate Reference Compound 121 to give the product of the Example.

MS (ESI) m/z 742.3 ((M+H)+);

Example 110

(2-oxo-5-phenyl-1,3-dioxol-4-yl)methyl 2-{[(7R,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate

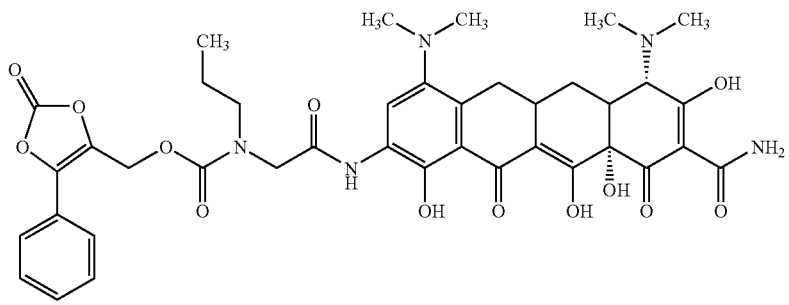

The title compound is prepared by the procedure of Example 108, using N-propyl-glycylcycline (N-prop-glycyl) and 4-nitrophenyl (2-oxo-5-phenyl-1,3-dioxol-4-yl)methyl carbonate Reference Compound 122 to give the product of the Example.

MS (ESI) m/z 790.3 ((M+H)+);

HRMS: calcd for $C_{39}H_{43}N_5O_{13}$, 789.2857. found (ESI+), 790.29243;

Example 111

[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate

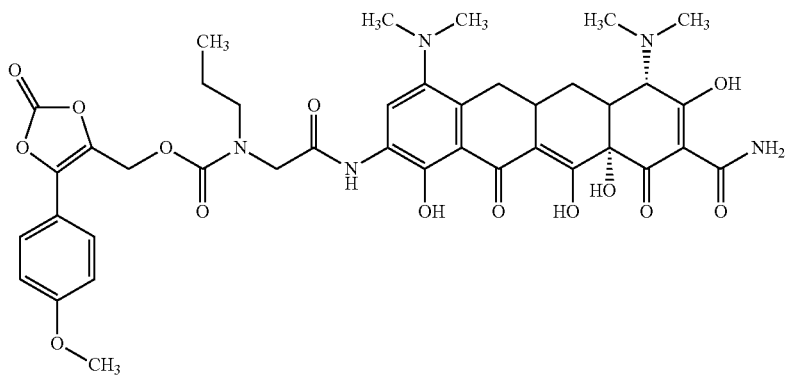

The title compound is prepared by the procedure of Example 108, using N-propyl-glycylcycline (N-prop-glycyl) and [5-(4-methoxyphenyl)-2-oxo-1,3-dioxol-4-yl]methyl 4-nitrophenyl carbonate Reference Compound 123 to give the product of the Example.

MS (ESI) m/z 820.3 ((M+H)+);

Example 112

(2-oxo-5-phenyl-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate

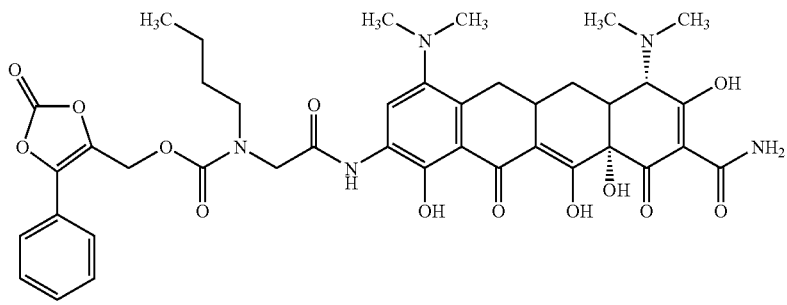

The title compound is prepared by the procedure of Example 108, using N-butyl-glycylcycline (N-bu-glycyl) and 4-nitrophenyl (2-oxo-5-phenyl-1,3-dioxol-4-yl)methyl carbonate Reference Compound 122 to give the product of the Example.
MS (ESI) m/z 804.12 (M+H);
MS (ESI) m/z 402.58 (M+2H);
HRMS: calcd for $C_{40}H_{45}N_5O_{13}$, 803.3014. found (ESI+), 804.30946;

Example 113

[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate

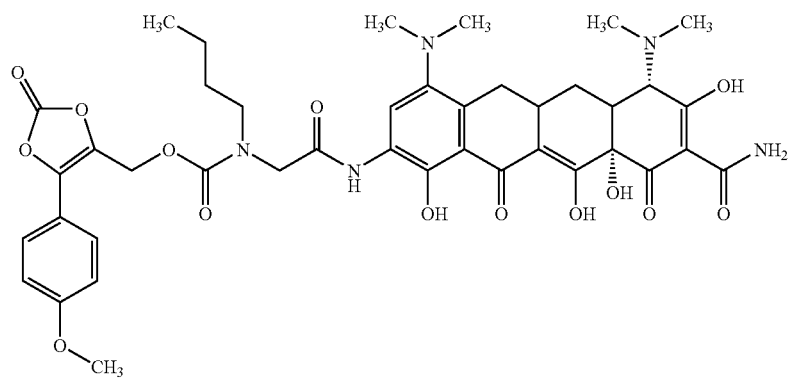

The title compound is prepared by the procedure of Example 108, using N-butyl-glycylcycline (N-bu-glycyl) and [5-(4-methoxyphenyl)-2-oxo-1,3-dioxol-4-yl]methyl 4-nitrophenyl carbonate Reference Compound 123 to give the product of the Example.

What is claimed is:
1. A compound represented by Formula (I);

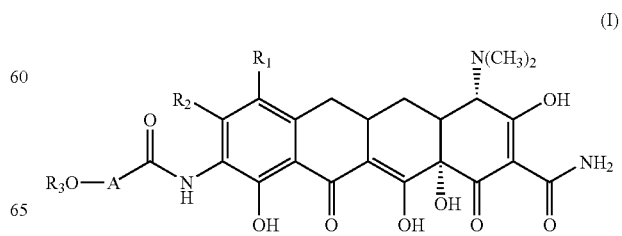

wherein:

A is a moiety $$\text{[structure: R}_4\text{-N-C(=O)- with ethylene linker]}$$

$R_1$ is selected from hydrogen, —OH, amino, —$NR_7R_8$, halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_2$ is selected from halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_3$ is selected from the moiety $$\text{[two structures with } R_5, R_6, R_{10} \text{ substituents]}$$

$R_4$ is selected from hydrogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkynyl of 2 to 12 carbon atoms optionally substituted with 1 to 3 substituents independently selected from the group halogen, amino, cyano, alkyl, hydroxyl, and alkoxy, aryl of 6, 10 or 14 carbon atoms said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, N-(alkyl of 1 to 12 carbon atoms)-aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl of 7 to 13 carbon atoms optionally substituted, $SR^3$, heteroaryl optionally substituted and heteroarylcarbonyl optionally substituted;

$R_5$ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, or 14 carbon atoms, aryloxy and N-(alkyl of 1 to 12 carbon atoms)-aryl, wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—

C(O)—NH—, aralkyl, aryloxy, heterocyclyl and phenyl, aralkyl of 7 to 16 carbon atoms optionally substituted, aroyl, —CH$_2$(CO)OCH$_2$aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, alkenyl of 2 to 12 carbon atoms optionally substituted, heteroaryl optionally substituted, aryl of 6, 10 or 14 carbon atoms optionally substituted, alkynyl of 2 to 12 carbon atoms optionally substituted, cycloalkyl 3 to 6 ring atoms, aryl-CH═CH—, cycloalkyl-alkyl; and adamantly;

R$_6$ is selected from hydrogen, alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, CH$_3$—C(O)—NH—, aralkyl, aryloxy, heterocyclyl and phenyl, and cycloalkyl of 3 to 6 carbon atoms;

R$_7$ and R$_8$ are each independently H or R$_7$ and R$_8$ when optionally taken together with the nitrogen atom to which each is attached form a 3 to 8 membered heterocyclyl ring;

R$_{10}$ is H or alkyl of 1 to 12 carbon atoms;

or a pharmaceutically acceptable salt thereof.

2. A compound according to claim 1, wherein R$_1$ is —NR$_7$R$_8$, R$_7$ is hydrogen, R$_8$ is methyl, ethyl, n-propyl, n-butyl, 1-methylethyl, 1-methylpropyl, 2-methylpropyl or 1,1-dimethylethyl or a pharmaceutically acceptable salt thereof.

3. A compound according to claim 1, wherein R$_1$ is —NR$_7$R$_8$, R$_7$ and R$_8$ are taken together with the nitrogen atom to which each is attached form a 3 to 8 membered heterocyclyl ring or a pharmaceutically acceptable salt thereof.

4. A compound according to claim 1, wherein R$_3$ is a moiety

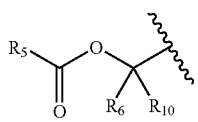

or a pharmaceutically acceptable salt thereof.

5. A compound according to claim 1, wherein R$_3$ is a moiety

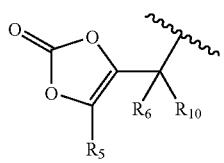

or a pharmaceutically acceptable salt thereof.

6. A compound according to claim 1, wherein R$_3$ is a moiety

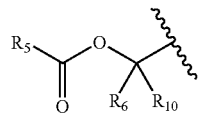

and R$_6$ and R$_{10}$ are H or a pharmaceutically acceptable salt thereof.

7. A compound according to claim 1, wherein R$_3$ is a moiety

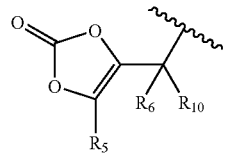

and R$_6$ and R$_{10}$ are H or a pharmaceutically acceptable salt thereof.

8. A compound according to claim 1, wherein A is the moiety,

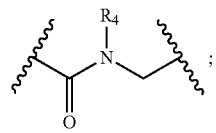

R$_3$ is the moiety

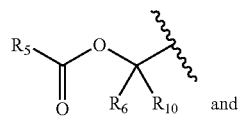 and

R$_5$ is aryl of 6 carbon atoms or a pharmaceutically acceptable salt thereof.

9. A compound according to claim 1, wherein A is the moiety

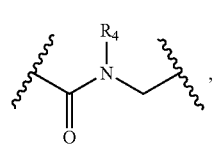

R$_3$ is the moiety,

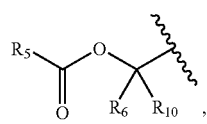

R$_4$ is 1,1-dimethylethyl and
R$_5$ is aryl of 6 carbon atoms or a pharmaceutically acceptable salt thereof.

10. A compound according to claim 1, wherein
A is a moiety

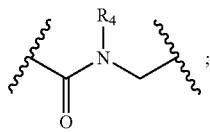

$R_1$ is —$NR_7R_8$;
$R_3$ is the moiety

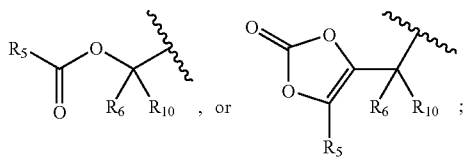

$R_4$ is selected from alkyl of 1 to 12 carbon atoms optionally substituted with 0.1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, and aryloxy wherein said aryl and aryloxy is optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl;
$R_5$ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, or 14 carbon atoms, and aryloxy wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl, —$CH_2$(CO)$OCH_2$aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, heteroaryl optionally substituted, aryl of 6, 10 or 14 carbon atoms optionally substituted, cycloalkyl 3 to 6 ring atoms, aryl-CH=CH—, cycloalkyl-alkyl; and adamantyl;
$R_8$ is hydrogen;
$R_7$ and $R_8$ are each independently H;
$R_{10}$ is H;
or a pharmaceutically acceptable salt thereof.
11. A compound according to claim 1, selected from the group or pharmaceutically acceptable salts thereof
({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 2-methylpropanoate, ({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methoxybenzoate, ({[(2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-methylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 4-fluorobenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-methoxybenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl cyclobutanecarboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 4-fluorobenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl pivalate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-methylpropanoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl phenylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl phenylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl pivalate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl heptanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl cyclobutanecarboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl)oxy) methyl heptanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl 4-tert-butylbenzoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl 1,1'-biphenyl-4-carboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl 3,5-dimethylbenzoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl 1,1'-biphenyl-4-carboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl 3,5-dimethylbenzoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl 4-tert-butylbenzoate, 1-({[(2-{[(7S,10aS)-9-(aminocarbonyl)-4,7-bis(dimethy-lamino)-1,8,10a,11-tetrahydroxy-10,12-dioxo-5,5a,6, 6a,7,10,10a,12-octahydrotetracen-2-yl]amino}-2-oxo-ethyl)(butyl)amino]carbonyl}oxy)ethyl acetate, ({[(2-{[(7S,10aS)-9-(aminocarbonyl)-4,7-bis(dimethy-lamino)-1,8,10a,11-tetrahydroxy-10,12-dioxo-5,5a,6, 6a,7,10,10a,12-octahydrotetracen-2-yl]amino}-2-oxo-ethyl)(propyl)amino]carbonyl}oxy)methyl cyclohexanecarboxylate, ({[(2-{[(7S,10aS)-9-(aminocarbonyl)-4,7-bis(dimethy-lamino)-1,8,10a,11-tetrahydroxy-10,12-dioxo-5,5a,6, 6a,7,10,10a,12-octahydrotetracen-2-yl]amino}-2-oxo-ethyl)(butyl)amino]carbonyl}oxy)methyl cyclohexanecarboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl 3,3-dimethylbutanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl 3,3-dimethylbutanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl 2,2-dimethylbutanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl cyclopentylacetate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(butyl)amino]carbonyl}oxy) methyl adamantane-1-carboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl cyclopentylacetate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(propyl)amino]carbonyl}oxy) methyl adamantane-1-carboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 3,3-dimethylbutanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 4-tert-butyl benzoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 2,2-dimethylbutanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 2-methylpropanoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl cyclopentanecarboxylate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 4-methylbenzoate, ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl heptanoate, and ({[(2-{[(5aR,6aS,7S,10aS)-9-(aminocarbonyl)-4,7-bis (dimethylamino)-1,8,10a,11-tetrahydroxy-10,12-di-oxo-5,5a,6,6a,7,10,10a,12-octahydrotetracen-2-yl] amino}-2-oxoethyl)(tert-butyl)amino]carbonyl}oxy) methyl 4-methoxybenzoate.

12. A compound according to claim 1 selected from the group

- benzyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate,
- ethyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate, and
- isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate, or pharmaceutically acceptable salts thereof.

13. A compound according to claim 1 selected from the group

- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-2-carboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-2-carboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl thiophene-3-carboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl thiophene-3-carboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(butyl)amino]carbonyl}oxy)methyl 2-furoate, and
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(propyl)amino]carbonyl}oxy)methyl 2-furoate, or pharmaceutically acceptable salts thereof.

14. A compound according to claim 1 selected from the group

- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl propionate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclohexanecarboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,5-dimethylbenzoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-fluorobenzoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methylbutanoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopentylacetate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(trifluoromethyl)benzoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclopropanecarboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl adamantine-1-carboxylate,
- butyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate,
- isobutyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate,
- methyl 2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(tert-butyl)carbamate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl pentanoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclobutanecarboxylate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-cyclohexylpropanoate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl (4-fluorophenoxy)acetate,
- ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl cyclohexylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,6-dimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl phenylacetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl pivalate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1,1'-biphenyl-4-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-naphthoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-naphthoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,6-difluorobenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-fluorobenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-(trifluoromethyl)benzoate, (([(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1,1'-biphenyl-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2,4,6-trimethylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-isopropoxybenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,4,5-trimethoxybenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3,5-dimethoxybenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl (2E)-3-phenylprop-2-enoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl[3,5-bis(trifluoromethyl)phenyl]acetate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(heptyloxy)benzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 2-(2-phenylethyl)benzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(dodecyloxy)benzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-(acetylamino)benzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl anthracene-9-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-benzoylbenzoate, and ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl diphenylacetate.

15. A compound according to claim 1 selected from the group ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1H-indole-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl nicotinate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl isonicotinate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 4-pyrrolidin-1-ylbenzoate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 3-methyl-1-benzofuran-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-methyl-1H-indole-3-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl quinoline-2-carboxylate, ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl 1-benzofuran-2-carboxylate, and ({[(2-{[(5aR,6aS,7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl)(tert-butyl)amino]carbonyl}oxy)methyl-1-methyl-1H-pyrrole-2-carboxylate or pharmaceutically acceptable salts thereof.

16. A compound according to claim 1 selected from the group (5-methyl-2-oxo-1,3-dioxol-4-yl)methyl 2-{[(7S,10aR)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate, (5-methyl-2-oxo-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate, (2-oxo-5-phenyl-1,3-dioxol-4-yl)methyl 2-{[(7R,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate,

[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(propyl)carbamate, (2-oxo-5-phenyl-1,3-dioxol-4-yl)methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate and

[5-(4-methoxyphenyl)-2-oxo-1,3-dioxol-4-yl]methyl 2-{[(7S,10aS)-9-(aminocarbonyl)-4,7-bis(dimethylamino)-1,8,10a,11-tetrahydroxy-10,12-dioxo-5,5a,6,6a,7,10,10a,12-octahydrotetracen-2-yl]amino}-2-oxoethyl(butyl)carbamate or pharmaceutically acceptable salts thereof.

17. A pharmaceutical composition comprising a compound according to claim 1, in association with a pharmaceutically acceptable carrier.

\* \* \* \* \*